US012570991B2

(12) United States Patent
Kang et al.

(10) Patent No.: US 12,570,991 B2
(45) Date of Patent: Mar. 10, 2026

(54) RECOMBINANT YEAST STRAIN HAVING STEROL PRODUCTIVITY, PREPARATION METHOD THEREFOR AND USE THEREOF

(71) Applicants: Daewoong Pharmaceutical Co., Ltd., Gyeonggi-do (KR); Chung Ang University Industry Academic Cooperation Foundation, Seoul (KR)

(72) Inventors: Hyun Ah Kang, Seoul (KR); Hye Yun Moon, Seoul (KR); Hui Jeong Jang, Gyeonggi-do (KR); Seon A Jung, Seoul (KR)

(73) Assignees: Daewoong Pharmaceutical Co., Ltd., Seoul (KR); Chung Ang University Industry Academic Cooperation Foundation, Seoul (KR)

( * ) Notice: Subject to any disclaimer, the term of this patent is extended or adjusted under 35 U.S.C. 154(b) by 1177 days.

(21) Appl. No.: 17/263,507

(22) PCT Filed: Jul. 26, 2019

(86) PCT No.: PCT/KR2019/009360
§ 371 (c)(1),
(2) Date: Feb. 26, 2021

(87) PCT Pub. No.: WO2020/022847
PCT Pub. Date: Jan. 30, 2020

(65) Prior Publication Data
US 2021/0171963 A1      Jun. 10, 2021

(30) Foreign Application Priority Data
Jul. 26, 2018      (KR) ........................ 10-2018-0087372

(51) Int. Cl.
*C12N 15/81*      (2006.01)
*C12N 15/69*      (2006.01)
*C12P 33/06*      (2006.01)

(52) U.S. Cl.
CPC ............. *C12N 15/81* (2013.01); *C12N 15/69* (2013.01); *C12P 33/06* (2013.01)

(58) Field of Classification Search
CPC ........ C12N 9/001; C12N 9/10; C12N 9/1007; C12N 15/52; C12N 15/69; C12N 15/81; C12N 15/90; C12P 33/06; C12R 2001/865; C12Y 103/01021; C12Y 103/01071; C12Y 103/01072; C12Y 114/19; C12Y 201/01041
See application file for complete search history.

(56) References Cited

U.S. PATENT DOCUMENTS

2004/0235088 A1* 11/2004 Weber ..................... C12P 5/007
435/254.2

FOREIGN PATENT DOCUMENTS

| CN | 106754993 | 5/2017 |
|----|-----------|--------|
| JP | 2012-024084 | 2/2012 |
| KR | 10-0418187 | 2/2004 |
| KR | 10-2016-0024353 | 3/2016 |
| KR | 10-2019-0080790 | 7/2019 |
| WO | WO 2006/014837 | 2/2006 |

OTHER PUBLICATIONS

Shivapurkar et al. "An efficient method for the production of isotopically enriched cholesterol for NMR", Journal of Lipid Research, 2011, vol. 52, Issue 5, pp. 1062-1065. (Year: 2011).*
Hirz et al. "A novel cholesterol-producing Pichia pastoris strain is an ideal host for functional expression of human Na,K-ATPase α3β1 isoform", Applied Microbiology and Biotechnology, 2013, vol. 97, pp. 9465-9478. (Year: 2013).*
Shivapurkar et al. "An efficient method for the production of isotopically enriched cholesterol for NMR", Journal of Lipid Research, 2011, vol. 52, No. 5, pp. 1062-1065. (Year: 2011).*
Gnugge et al. "A shuttle vector series for precise genetic engineering of *Saccharomyces cerevisiae*", Yeast, 2015, vol. 33, No. 3, pp. 83-98. (Year: 2015).*
Albertsen et al. "Diversion of Flux toward Sesquiterpene Production in *Saccharomyces cerevisiae* by Fusion of Host and Heterologous Enzymes", Applied and Environmental Microbiology, 2011, vol. 77, No. 3, pp. 1033-1040. (Year: 2011).*
Moon et al. "A new set of rDNA-NTS-based multiple integrative cassettes for the development of antibiotic-marker-free recombinant yeasts", Journal of Biotechnology, 2016, vol. 233, pp. 190-199. (Year: 2016).*
Hirz et al., "A novel cholesterol-producing Pichia pastoris strain is an ideal host for functional expression of human Na,K-ATPase α3β1 isoform," Appl Microbiol Biotechnol (2013) 97:9465-9478.
Entian et al., "25 Yeast Genetic Strain and Plasmid Collections," Methods in Microbiology (2007) 36:629-666.
GenBank Accession No. XM_014260434.1, retrieved on Oct. 16, 2019, ttps://www.ncbi.nlm.nih.gov/nucleotide/XM_014260434.1.
Guo et al.. "Metabolic engineering of *Saccharomyces cerevisiae* for 7-dehydrocholesterol overproduction," Biotechnol Biofuels (2018) 11:192.

(Continued)

*Primary Examiner* — Melenie L Gordon
*Assistant Examiner* — Deepa Mishra
(74) *Attorney, Agent, or Firm* — Myers Bigel, P.A.

(57) ABSTRACT

The present invention relates to a recombinant yeast strain having sterol productivity, a preparation method therefor and a use thereof, and more specifically, to a recombinant yeast strain capable of producing cholesterol and cholesterol precursors in a high yield through the deletion of ERG5 and ERG6 genes and the introduction of DHCR24 and DHCR7 genes by codon-optimizing same in multiple or with a codon context method; and a production method therefor and a use thereof. In addition, disclosed are: a method for producing a recombinant yeast strain with increased production yields of cholesterol and cholesterol precursors by the additional introduction of gene tHMG1, ERG2, ERG3, ERG27, or UPC2-1 in the prepared recombinant yeast strain; and a use thereof.

2 Claims, 32 Drawing Sheets
Specification includes a Sequence Listing.

(56)                References Cited

OTHER PUBLICATIONS

Hill et al., "Mouse small eye results from mutations in a paired-like homeobox-containing gene," Nature (1991) 354:522-525.

Moon et al., "A new set of rDNA-NTS-based multiple integrative cassettes for the development of antibiotic-marker-free recombinant yeasts," J Biotechnolgy (2016) http://dx.doi.org/10.1016/j.jbiotec.

Shivapurkar et al., "An efficient method for the production of isotopically enriched cholesterol for NMR," J Lipid Research (2011) 52:1062-1065.

Souza et al., "A stable yeast strain efficiently producing cholesterol instead of ergosterol is functional for tryptophan uptake, but not weak organic acid resistance," Metabolic Engineering (2011) 13:555-569.

Examination Report issued for Indian Patent Application No. 202147008029 (11 pages) (dated Nov. 6, 2025).

Hu, et al., "Recent Advances in Ergosterol Biosynthesis and Regulation Mechanisms in *Saccharomyces cerevisiae*", Indian J Microbiol, 53(7):270-277 (2017).

* cited by examiner

WT

*are2Δ*

$_{NTS}$D24D7/#19

*are2Δ/$_{NTS}$D24D7/#19*

RECOMBINANT YEAST STRAIN HAVING STEROL PRODUCTIVITY, PREPARATION METHOD THEREFOR AND USE THEREOF

CROSS REFERENCE TO RELATED APPLICATIONS

This application is a national stage application under 35 U.S.C. § 371 of International Application No. PCT/KR2019/009360, filed internationally on Jul. 26, 2019, which claims priority to and the benefit of Korean Patent Application No. 10-2018-0087372, filed on Jul. 26, 2018, the disclosures of which are incorporated herein by reference in their entirety.

INCORPORATION BY REFERENCE OF SEQUENCE LISTING

The present application is being filed along with a Sequence Listing in electronic format. The Sequence Listing is provided as a file entitled 717572003600SeqList.txt, created Feb. 25, 2021, which is 36.8 kilobytes in size. The information in the electronic format of the Sequence Listing is incorporated by reference in its entirety.

TECHNICAL FIELD

The present invention relates to a recombinant yeast strain having sterol productivity, a method of preparing the same and a use thereof, and more particularly, to a recombinant yeast strain that can produce cholesterol and cholesterol precursors in high yields through deletion of ERG5 and ERG6 genes and introduction of codon-optimized DHCR24 and DHCR7 genes by multiple integration or in a codon context method, a method of preparing the same, and a use thereof. Further, the present invention relates to a method of preparing a recombinant yeast strain with increased production yields of cholesterol and cholesterol precursors by additionally introducing tHMG1, ERG2, ERG5, ERG27 or UPC2-1 gene into the prepared recombinant yeast strain and a use thereof.

BACKGROUND ART

Yeasts are attracting attention as a host capable of introducing and expressing various secondary metabolite biosynthesis pathways. Secondary metabolites produced by various living organisms are a main source of high value-added chemical compounds, and have important medical properties. Particularly, plant metabolites are functional materials that prevent bacterial, viral or fungal infections due to an antioxidant or antibiotic function and are useful for human health, and highly useful as therapeutic agents, so that there is a high demand for mass production technology using microorganisms. Yeasts whose secondary metabolic biosynthesis pathways are self-limited do not interfere or compete with foreign metabolic pathways introduced by genetic engineering, and have the advantage of securing comprehensive information on the physiological state of a yeast host through transcriptome and metabolite analysis because a variety of omics analysis systems are well established. In addition, a detailed model for a metabolic process has been developed to construct in silico yeasts that can predict the behavior of a modified metabolic network, so it is easier to design and manufacture artificial cells using the yeasts. Further, as a single celled eukaryotic microorganism, a yeast is a host suitable for the expression of a foreign enzyme such as cytochrome P450 having activity even when being expressed in organelles such as the endoplasmic reticulum and mitochondria, and has post-translational modification ability essential for plant and animal-derived enzyme activity, compared to a prokaryotic microbial host. Meanwhile, cholesterol is a very important biomaterial in mammals, involved in the regulation of cell division, growth, development and differentiation, and known as a precursor of various types of essential metabolites (e.g., hormones, bile acids, etc.), and the precursor is known to play a significant role in the early stage of development and the aging process. Accordingly, the present invention is intended to provide a recombinant yeast strain that can produce cholesterol and precursors thereof in high yields.

PRIOR ART DOCUMENT

Patent Document

Korean Patent No. 10-0418187

DISCLOSURE

Technical Problem

The present invention is directed to providing a recombinant yeast strain having sterol (cholesterol and cholesterol precursors) productivity.

The present invention is also directed to providing a method of preparing a recombinant yeast strain having sterol (cholesterol and cholesterol precursors) productivity and a use thereof.

Technical Solution

The present invention provides a recombinant yeast strain having sterol productivity, in which ERG5 and ERG6 genes are deleted and into which DHCR24 and DHCR7 genes are introduced.

One or more copies of DHCR24 and DHCR7 genes may be introduced through multiple integration or one or more copies of codon-optimized DHCR24 and DHCR7 synthetic genes may be introduced. Here, when multiple copies of one or more of the DHCR24 and DHCR7 genes are introduced, the copy number of one or more of the DHCR24 and DHCR7 genes may be 2 to 10, and more preferably, 4 to 7. When the gene copy number is less than 2, it is difficult to achieve an expected effect, and if it exceeds 10, the change in effect is insignificant.

One or more selected from the group consisting of tHMG1, ERG3, ERG2, ERG27 and UPC2-1 genes may be additionally introduced into the recombinant yeast strain.

A synthetic gene encoding an ERG27-ERG2 fusion protein may be additionally introduced into the recombinant yeast strain.

The DHCR24 gene may be introduced into an ERG6 gene site, and the DHCR7 gene may be introduced into an ERG5 gene site. When the gene introduction sites are designed as above, cholesterol and cholesterol precursors may be produced in higher yields, and by-products such as ethanol and acetate are not accumulated.

The sterol may include one or more of cholesterol precursors and cholesterol.

The cholesterol precursors may include one or more selected from the group consisting of zymosterol, dehydrocholesterol, lathosterol, dehydrodesmosterol and desmosterol.

The recombinant strain may be prepared using a multiple gene integration cassette, which sequentially includes an N-terminal fragment gene of a *Saccharomyces cerevisiae* ribosomal DNA non-transcribed spacer (rDNA NTS), a target gene to be inserted, an auxotrophic selectable marker gene including a promoter region and a C-terminal fragment gene of the *Saccharomyces cerevisiae* rDNA NTS.

In the multiple gene integration cassette, the N-terminal fragment gene of the rDNA NTS may be represented by SEQ ID NO: 1 (cacaagaggt aggtcgaaac agaacatgaa agttggtcgg taggtgc), and the C-terminal fragment gene of the rDNA NTS gene may be represented by SEQ ID NO: 2 (ggttttgcac catatcttca taacctgtca ccttgaaact acctctggc).

The auxotrophic selectable marker gene may be URA3 gene having a promoter region represented by SEQ ID NO: 3 (gaaacgaaga taaatc), LEU2 gene having a promoter region represented by SEQ ID NO: 4 (ttacctttta catttcagca a), HIS3 gene having a promoter region represented by SEQ ID NO: 5 (cttcgaagaa tatactaaaa aatgagcagg caagataaac gaaggcaaag), or TRP1 gene having a promoter region represented by SEQ ID NO: 6 (tattgagcac gtgagtatac gtgattaagc acacaaaggc agcttggagt).

The DHCR24 and DHCR7 gene may be codon-optimized by a codon adaptation index or codon context method.

The DHCR7 gene codon-optimized by a codon adaptation index method may consist of SEQ ID NO: 9, and the DHCR24 gene codon-optimized by a codon adaptation index method may consist of SEQ ID NO: 10.

The DHCR24 gene codon-optimized by a codon context method may consist of SEQ ID NO: 17, and the DHCR7 gene codon-optimized by a codon context method may consist of SEQ ID NO: 18.

The recombinant yeast strain may further have tHMG1 gene.

In addition, the present invention provides a method of preparing a recombinant yeast strain having sterol productivity, which includes deleting ERG5 and ERG6 genes of a yeast strain and introducing DHCR24 and DHCR7 genes, into which multiple copies of one or more of the DHCR24 and DHCR7 genes may be introduced.

The yeast strain may be *Saccharomyces cerevisiae*.

The introduction of the DHCR24 and DHCR7 genes may be performed using a multiple gene integration cassette, which sequentially includes an N-terminal fragment gene of a *Saccharomyces cerevisiae* ribosomal DNA non-transcribed spacer (rDNA NTS), a target gene to be inserted, an auxotrophic selectable marker gene including a promoter region and a C-terminal fragment gene of the *Saccharomyces cerevisiae* rDNA NTS. Details are as described above.

In addition, the present invention provides a method of producing sterol by culturing the recombinant yeast strain in a medium.

The culture may be performed at 25 to 35° C. for 2 to 10 days.

[Advantageous Effects]

According to the present invention, cholesterol and precursors thereof may be produced in high yields by a recombinant strain in which ERG5 and ERG6 genes are deleted and multiple DHCR24 and DHCR7 genes are introduced, or a recombinant strain in which ERG5 and ERG6 genes are deleted and DHCR24 and DHCR7 genes codon-optimized by a codon context method are introduced. Further, the present invention relates to a method of preparing a recombinant yeast strain having increased production yields of cholesterol and cholesterol precursors by additionally introducing tHMG1, ERG2, ERG5, ERG27 or UPC2-1 gene into the prepared recombinant yeast strain and a use thereof.

DESCRIPTION OF DRAWINGS

FIG. 2A is a schematic diagram of preparing recombinant yeast strains #19 (erg5::D24/erg6::D7) and #S1 (erg6::D24/erg5::D7), and recombinant yeast strains into which multiple copies of DHCR24 are additionally integrated; and FIG. 2B is a schematic diagram of producing recombinant yeast strains by additional multiple DHCR24 and DHCR7 integration or overexpression, and additional introduction of ERG3, ERG2, ERG27-2 fusion and UPC2-1 into the recombinant yeast strains #19 (erg5::D24/erg6::D7) and #S1 (erg6::D24/erg5::D7).

FIG. 3A is a schematic diagram of producing a recombinant yeast strain by introducing DHCR24 and multiple DHCR7 integration into a wild-type *Saccharomyces cerevisiae* strain, a recombinant yeast strain into which ERG3, ERG2, ERG27-2 fusion and UPC2-1—are additionally introduced, and a recombinant yeast strain in which erg6 deletion and multiple DHCR24 integration are introduced; and FIG. 3B is a schematic diagram of producing recombinant yeast strains #cc19 (erg5::ccD24/erg6::ccD7) and #ccS1 (erg6::ccD24/erg5::ccD7) using DHCR24 (cc) and DHCR7(cc) codon-optimized by a codon context method and recombinant yeast strains into which the multiple integration of tHMG1 from which the N-terminus partially removed is additionally introduced.

FIG. 7A is the result (qPCR) of analyzing recombinant strain $_{NTS}$D24D7/#19 ($_{NTS}$D24D7/erg5::D24/erg6::D7) according to the number of integration cassettes; FIG. 7B is the result (HPLC-UV/Vis chromatogram) of analyzing the production amounts of cholesterol and precursors thereof of recombinant strains #19 and $_{NTS}$D24D7/#19; and FIG. 7C is the result (HPLC-UV/Vis chromatogram) of analyzing the productivity of cholesterol and precursors thereof of recombinant strain $_{2u}$D24D7/#S1 (DD: dehydrodesmosterol, D: desmosterol, Z: zymosterol, C: cholesterol).

Figure 9:
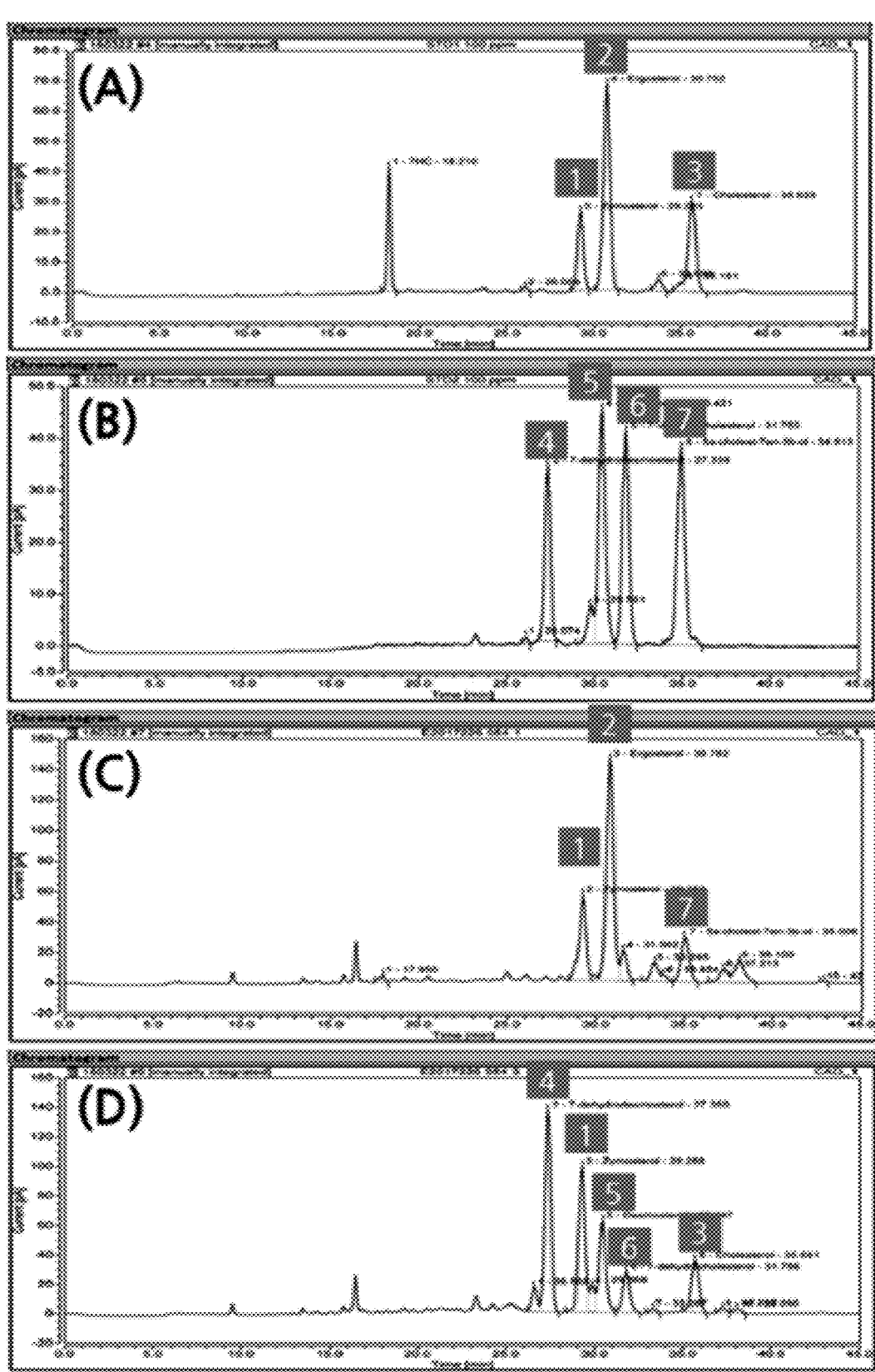

FIG. 9 shows newly constructed HPLC-CAD-based LC chromatograms, analyzing the production amounts of cholesterol and precursors thereof of recombinant yeast strains according to one embodiment of the present invention: FIG. 9(A) shows the LC chromatogram for three types of reference standards (1: zymosterol, 2: ergosterol, 3: cholesterol); FIG. 9(B) shows the LC chromatogram for four types of reference standards (4: 7-dehydrodesmosterol, 5: desmosterol, 6: 7-dehydrocholesterol, 7: lathosterol); FIG. 9(C) shows a wild-type strain (CEN.PK); and FIG. 9(D) shows recombinant strain #19 (erg5::D24/erg6::D7).

Figure 10A:
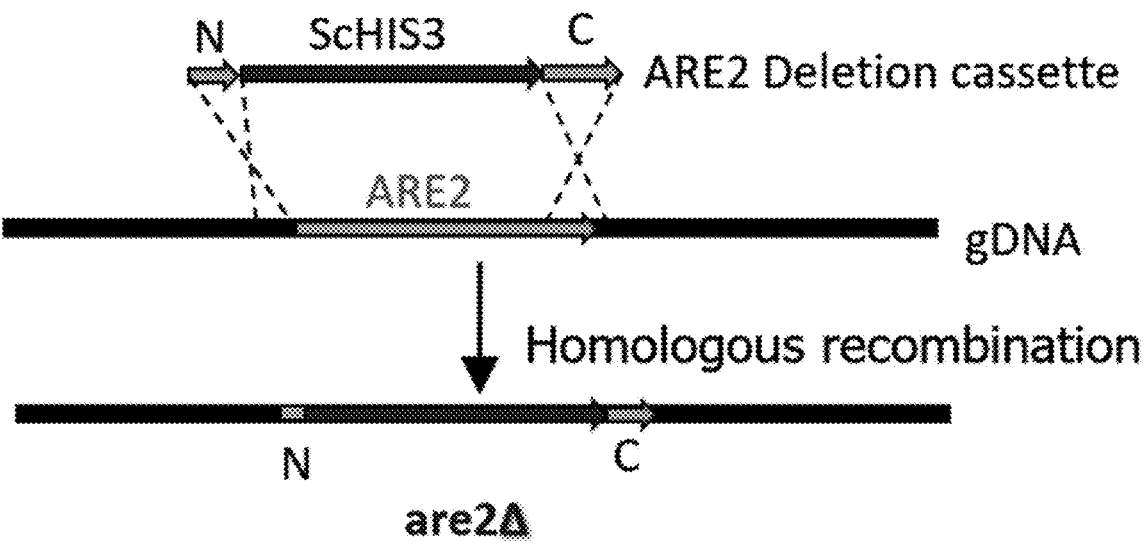
Figure 10B:
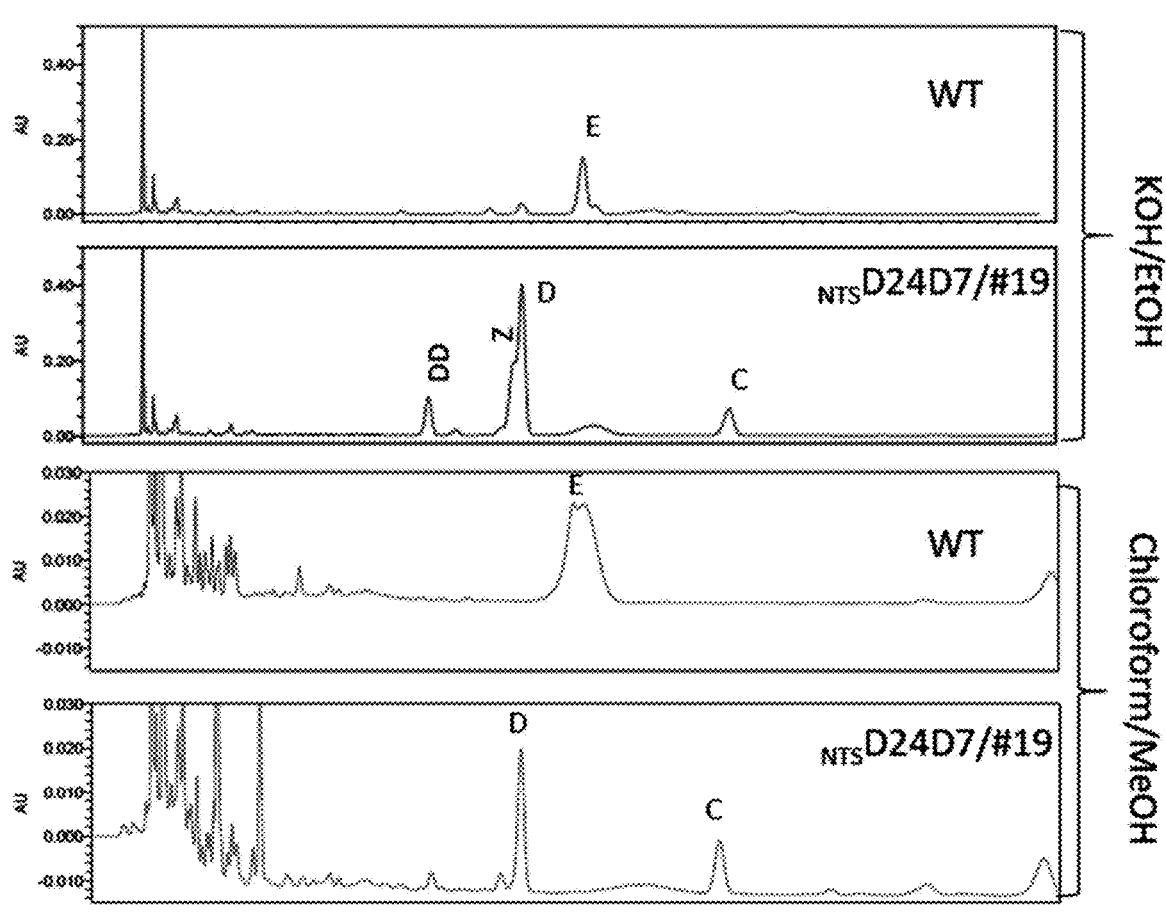
Figure 10C:
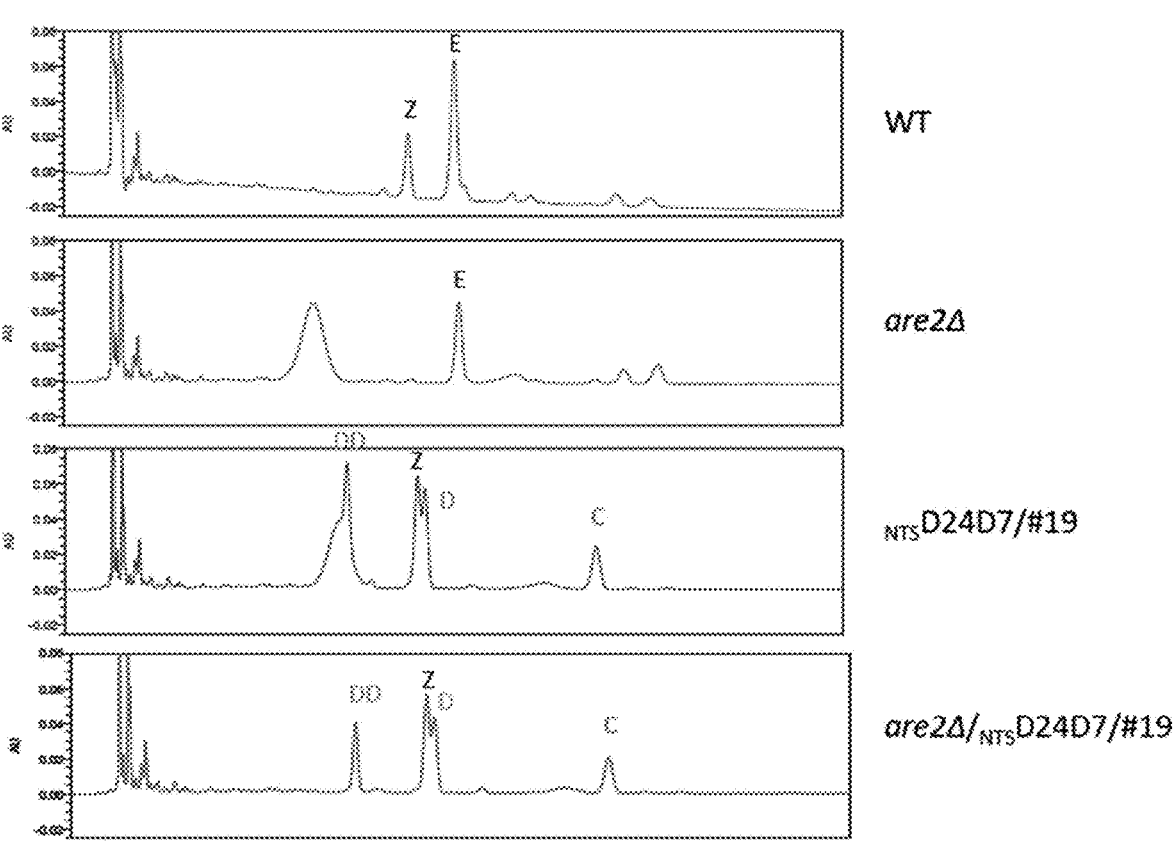

FIGS. 10A to 10C shows the result of analyzing sterol profiles of ARE2-deleted strains prepared according to one embodiment of the present invention: FIG. 10A is the schematic diagram of preparation of a homologous recombination-based ARE2-deleted strain; FIG. 10B shows the chromatograms of total sterols (KOH/EtOH) and free sterols (Chloroform/MeOH) obtained by a different HPLC-UV/Vis-based sterol extraction method; and FIG. 10C shows the HPLC-UV/Vis-based total sterol chromatogram of recombinant strain are2/N-rsD24D7/#19. (DD: dehydrodesmosterol, D: desmosterol, Z: zymosterol, C: cholesterol).

Figure 11A:
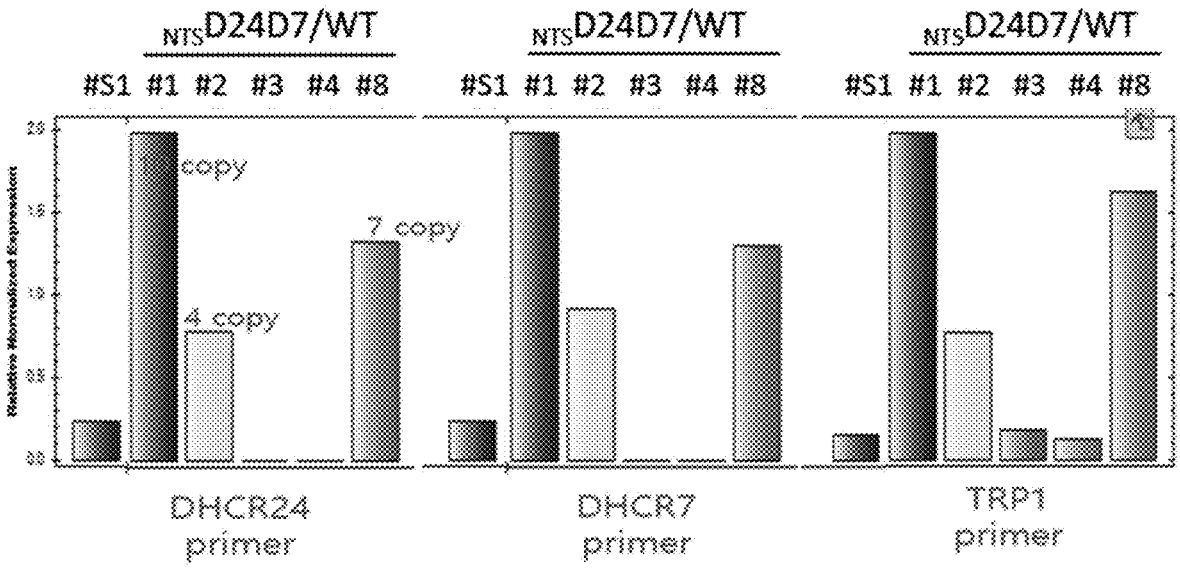
Figure 11B:
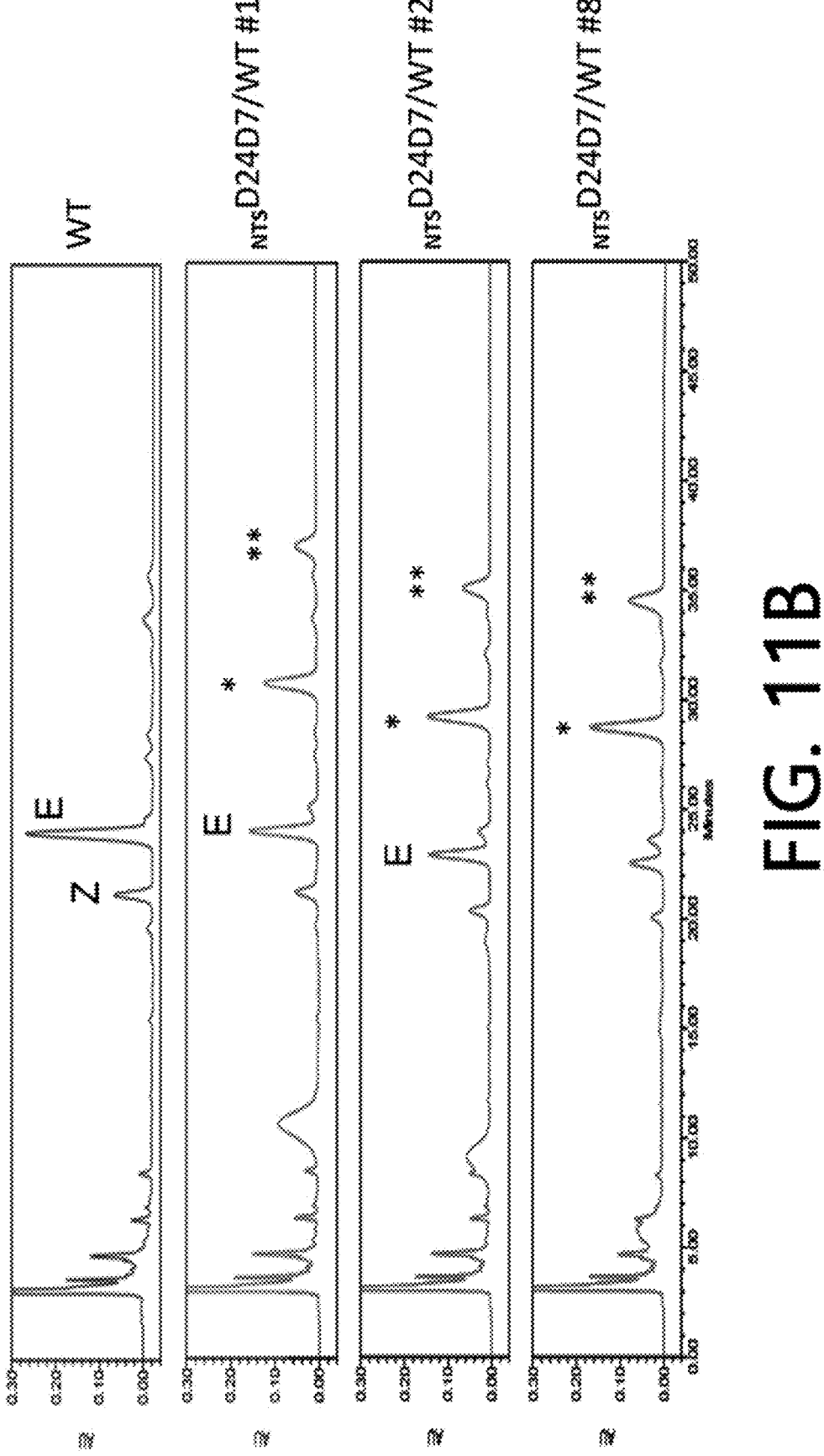
Figure 11C:
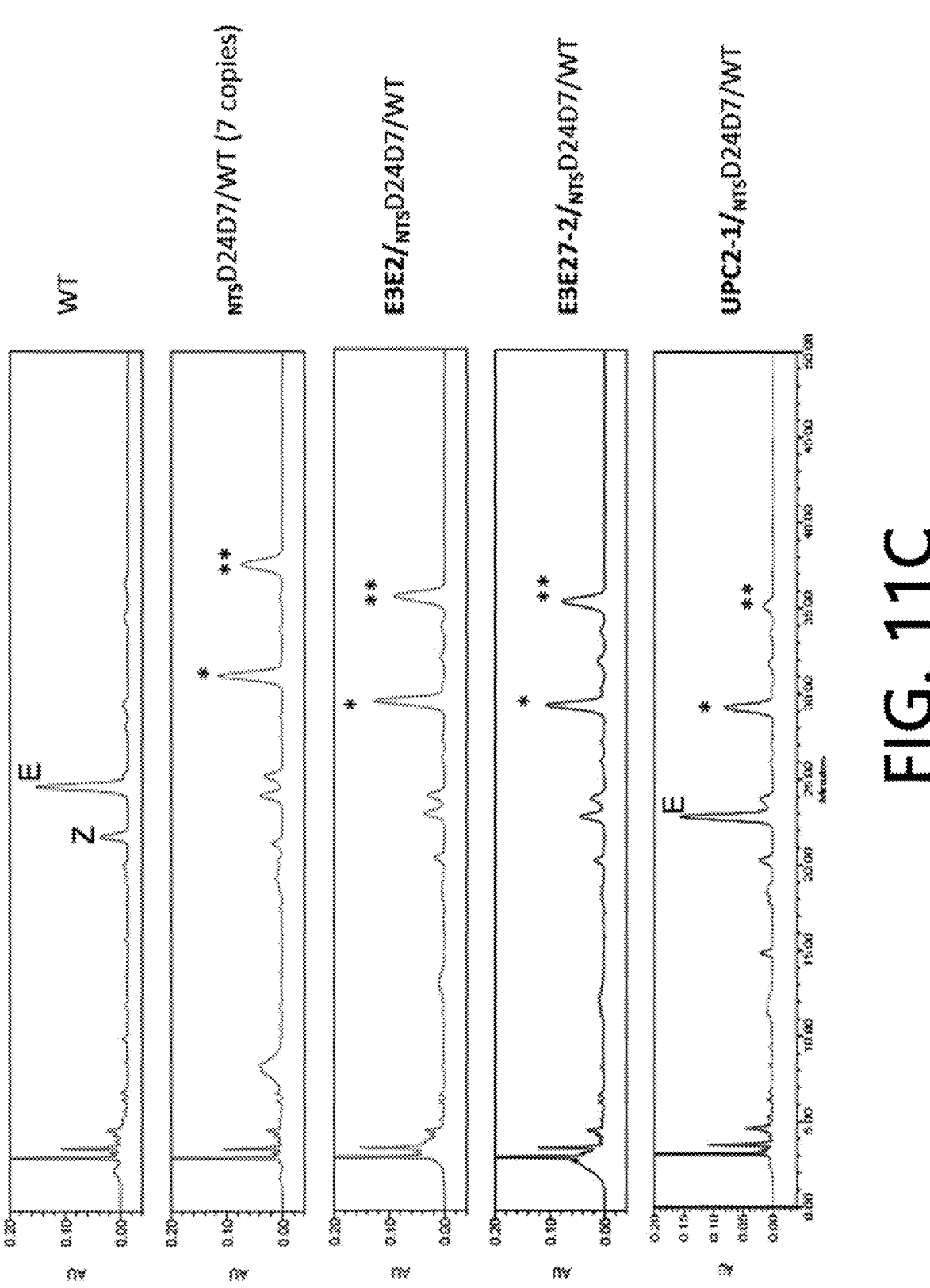
Figure 11D:
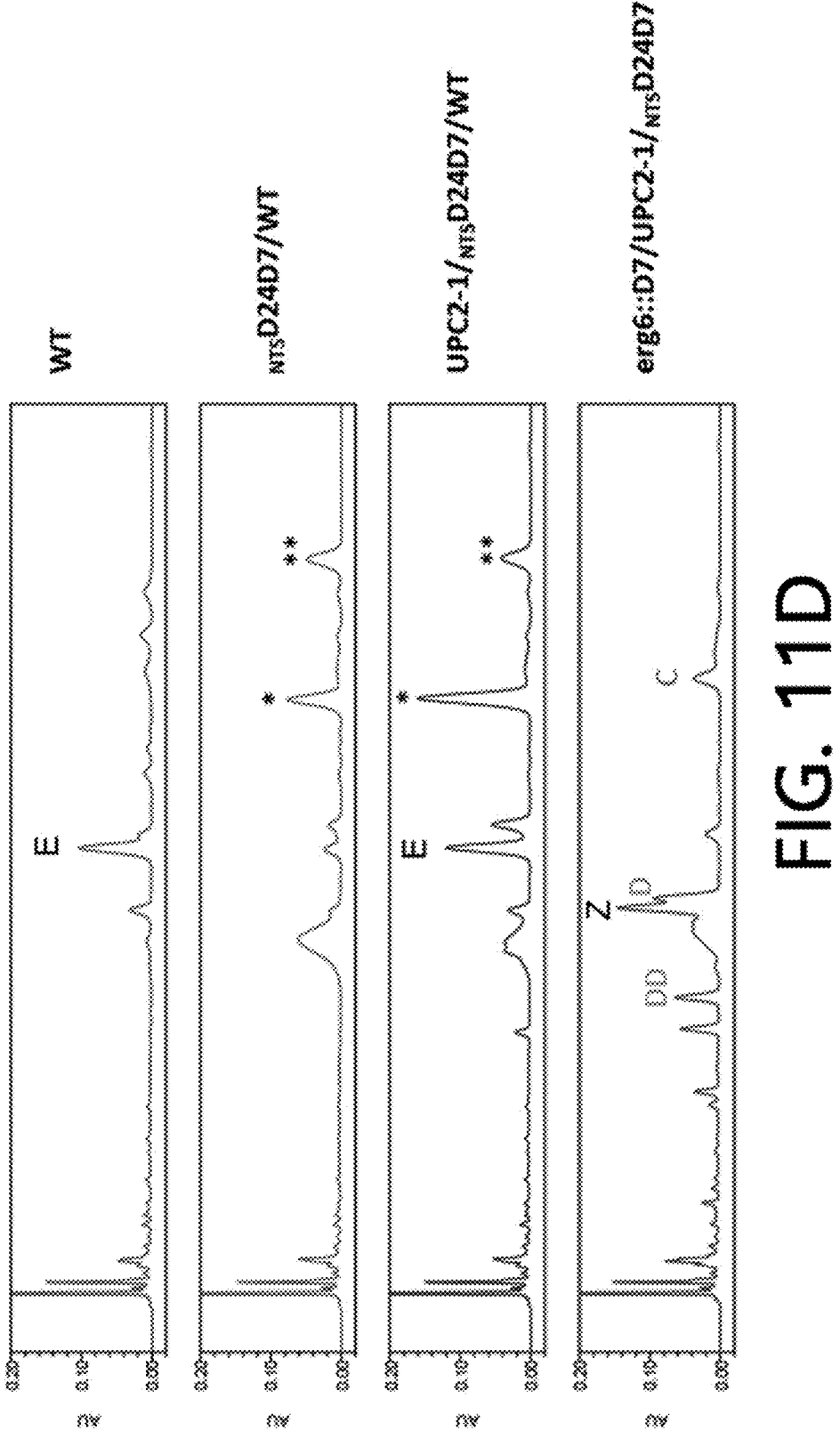

FIGS. 11A to 11C are the result of analyzing the relationship between the copy number and a sterol production amount of recombinant yeast strains prepared according to one embodiment of the present invention, and FIG. 11D is the result of HPLC-UV/Vis analysis showing the sterol profile of erg6::D7/UPC2-1/NTS D24D7 strain (*: unknown peak, DD: dehydrodesmosterol, D: desmosterol, Z: zymosterol, C: cholesterol).

Figure 12A:
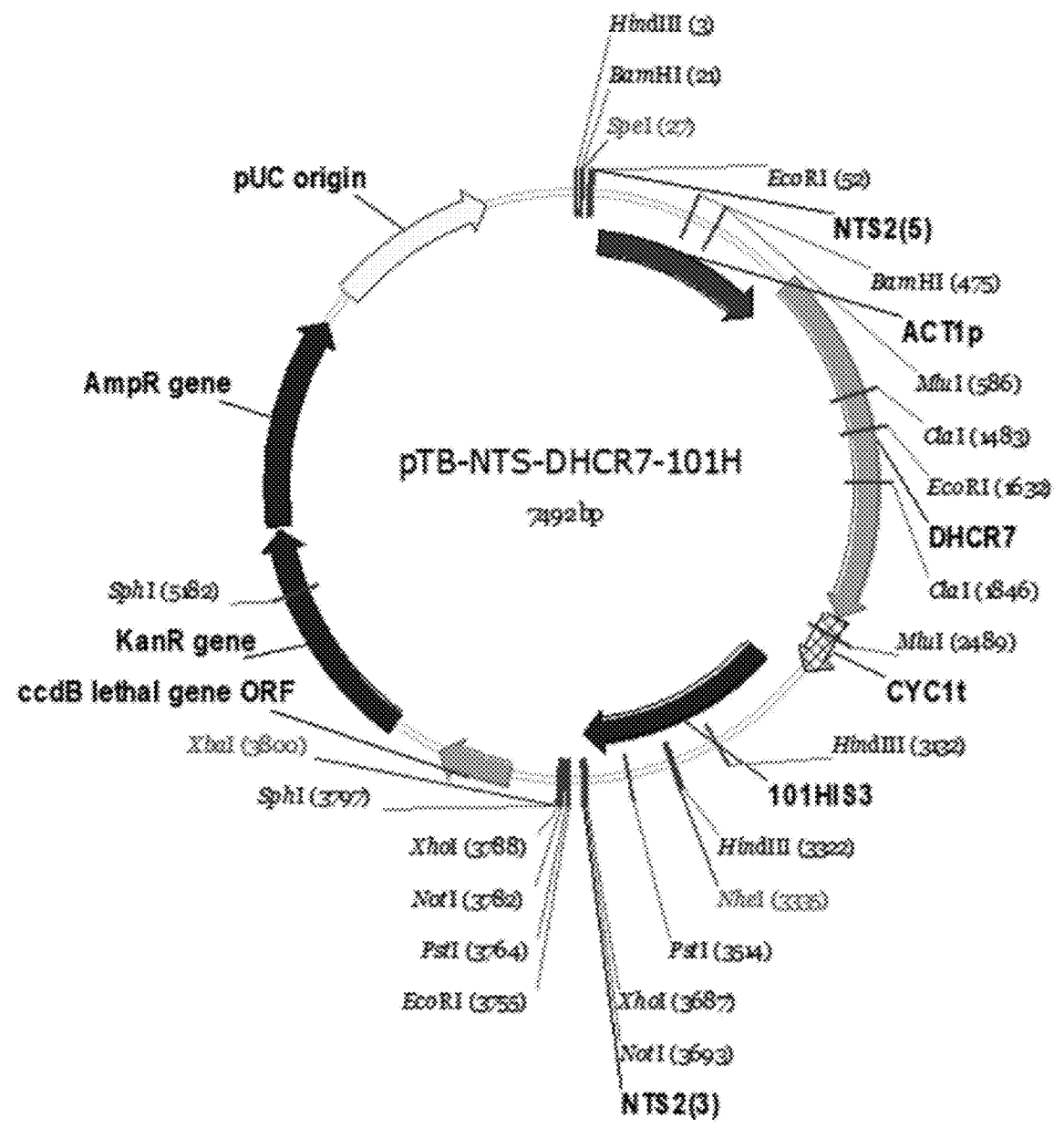
Figure 12B:
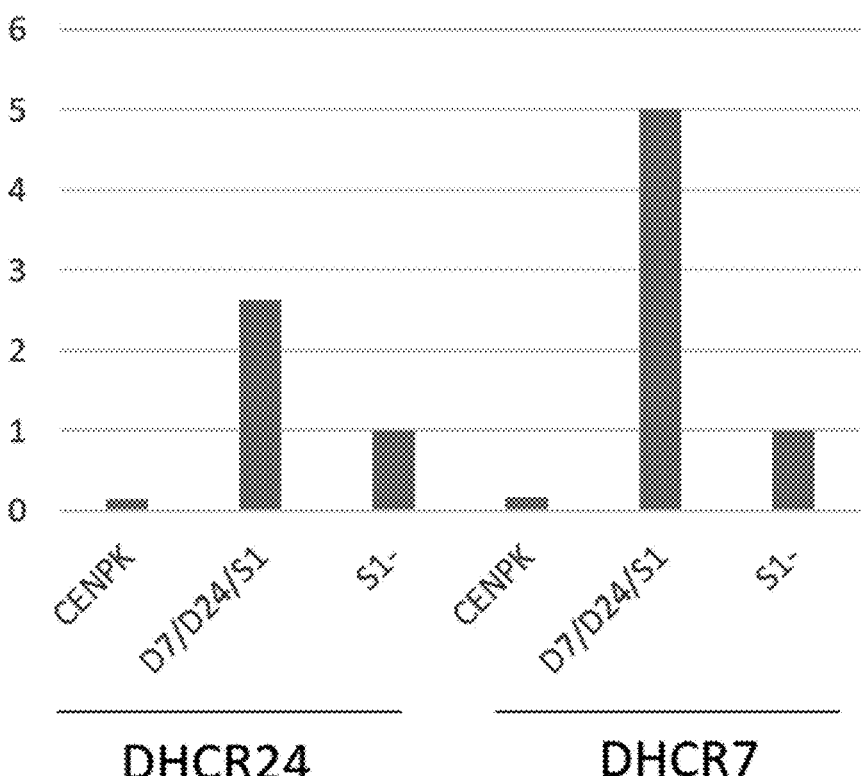
Figure 12C:
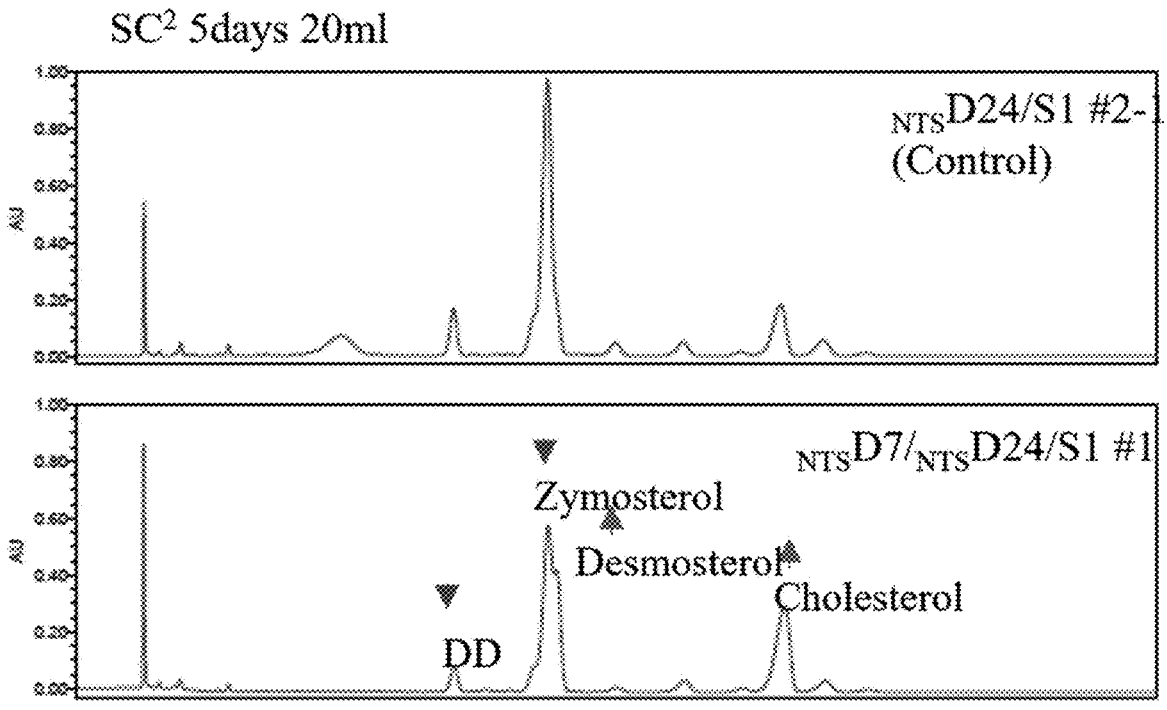

FIGS. 12A to 12C are the result of comparative analysis of characteristics of recombinant yeast strains according to one embodiment of the present invention: FIG. 12A shows a vector including a cassette used in the production of recombinant strain $_{NTS}$D7/$_{NTS}$D24/#S1; FIG. 12B shows an analysis result (qPCR analysis) according to the number of integration cassettes of recombinant strain $_{NTS}$D7/$_{NTS}$D24/#S1; and FIG. 12C shows the analysis result (HPLC-UV/Vis chromatogram) for the production amounts of cholesterol and precursors thereof of recombinant strain $_{NTS}$D7/$_{NTS}$D24/#S1.

Figure 13A:
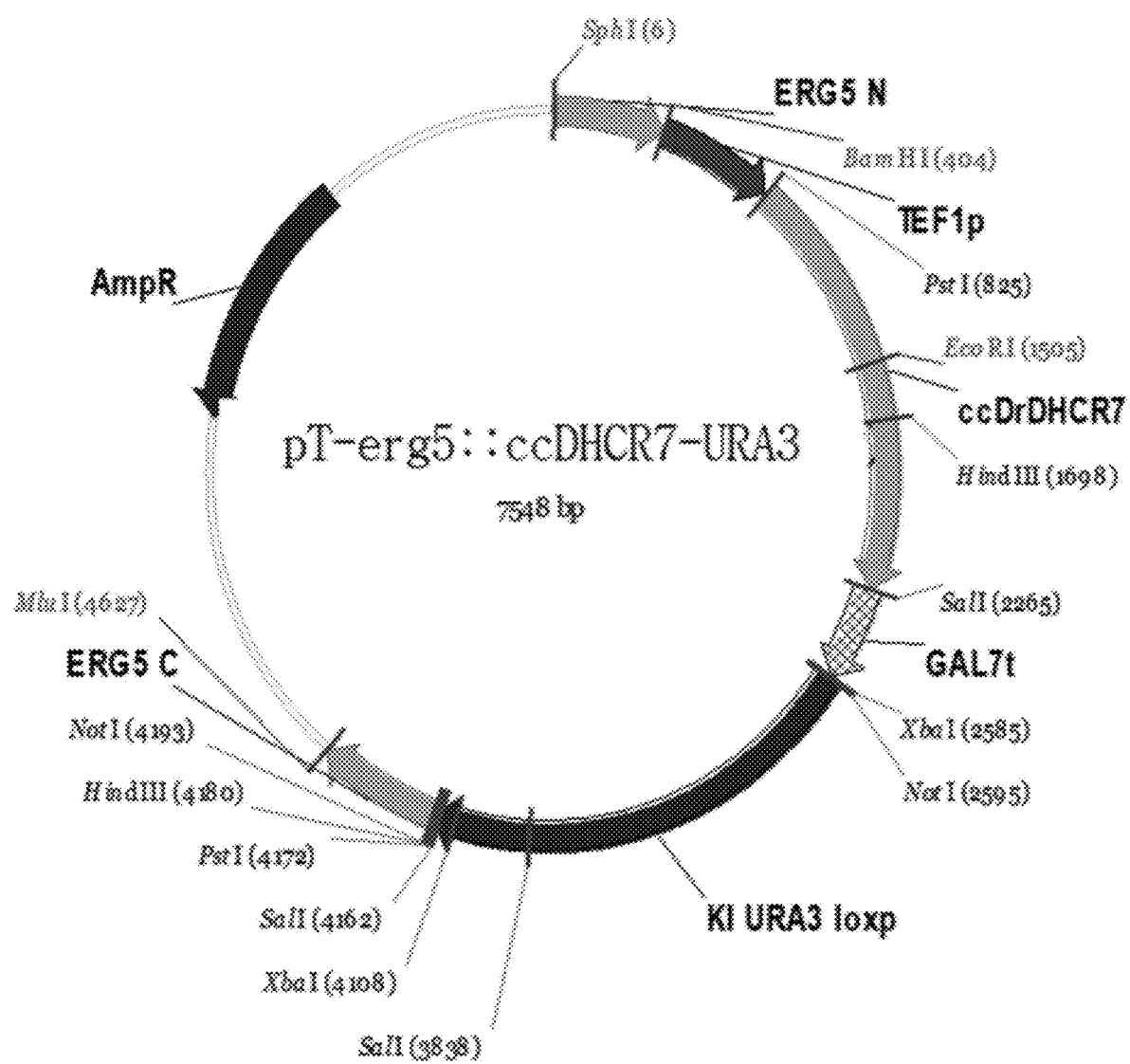
Figure 13B:
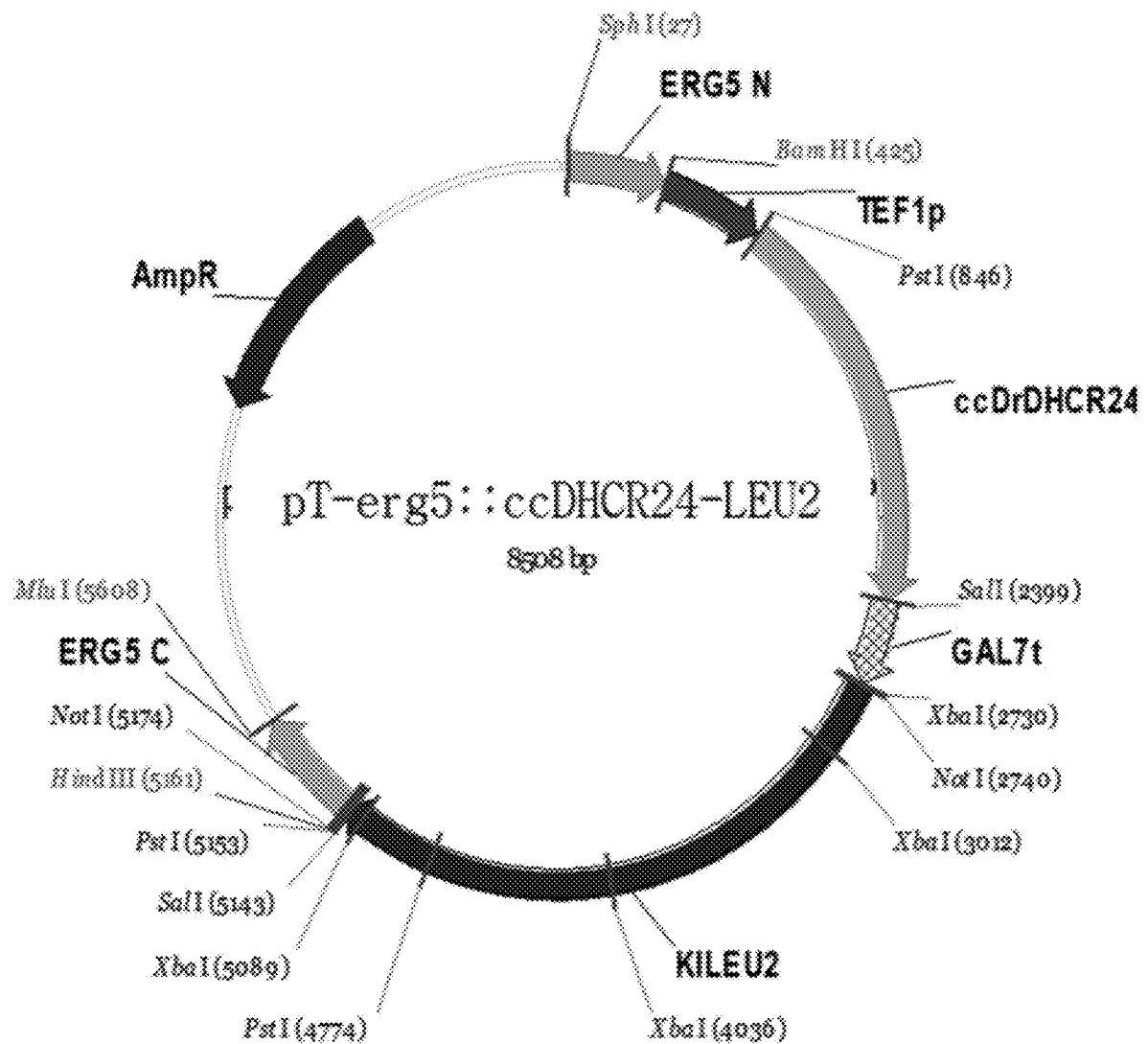
Figure 13C:
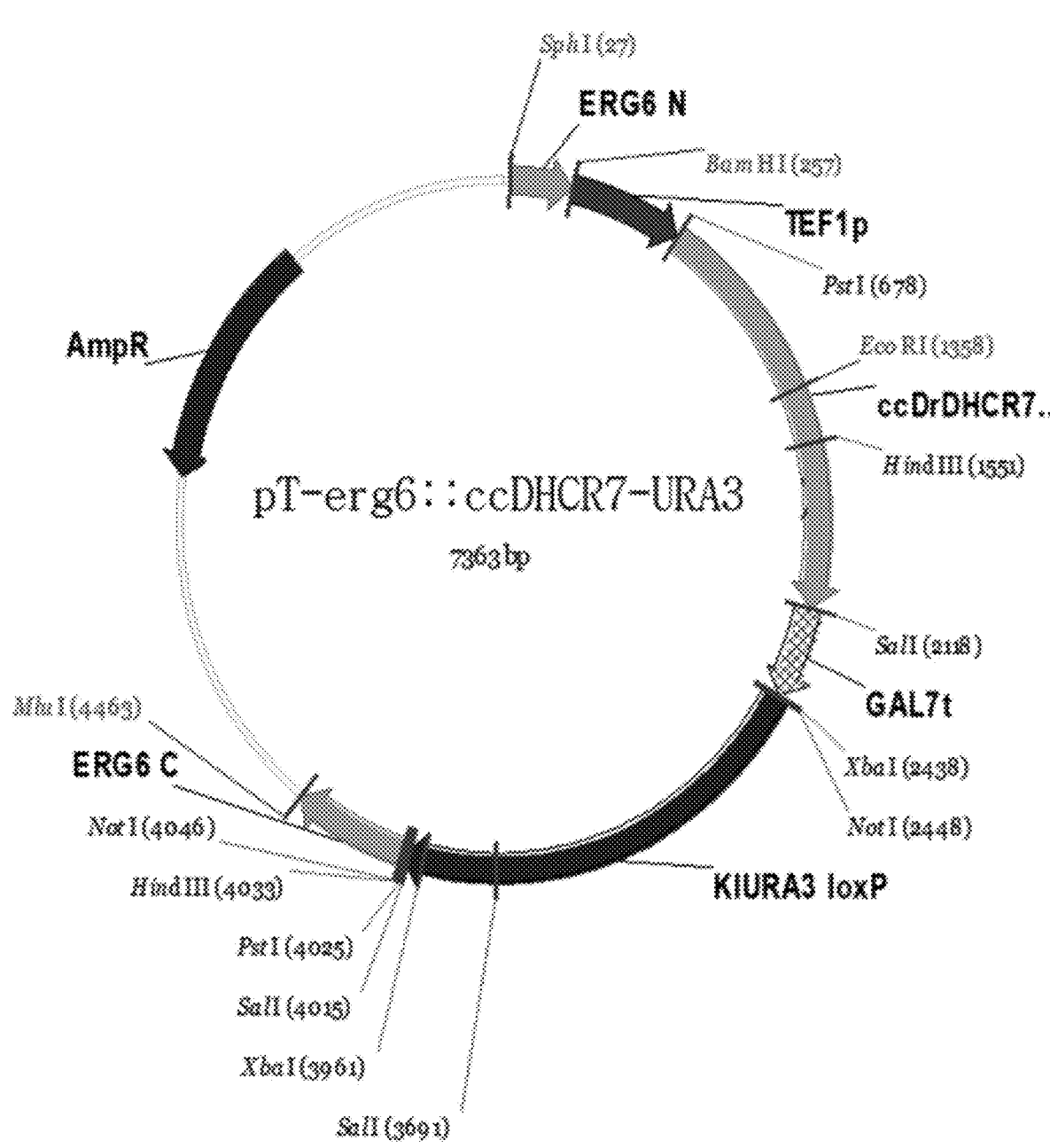
Figure 13D:
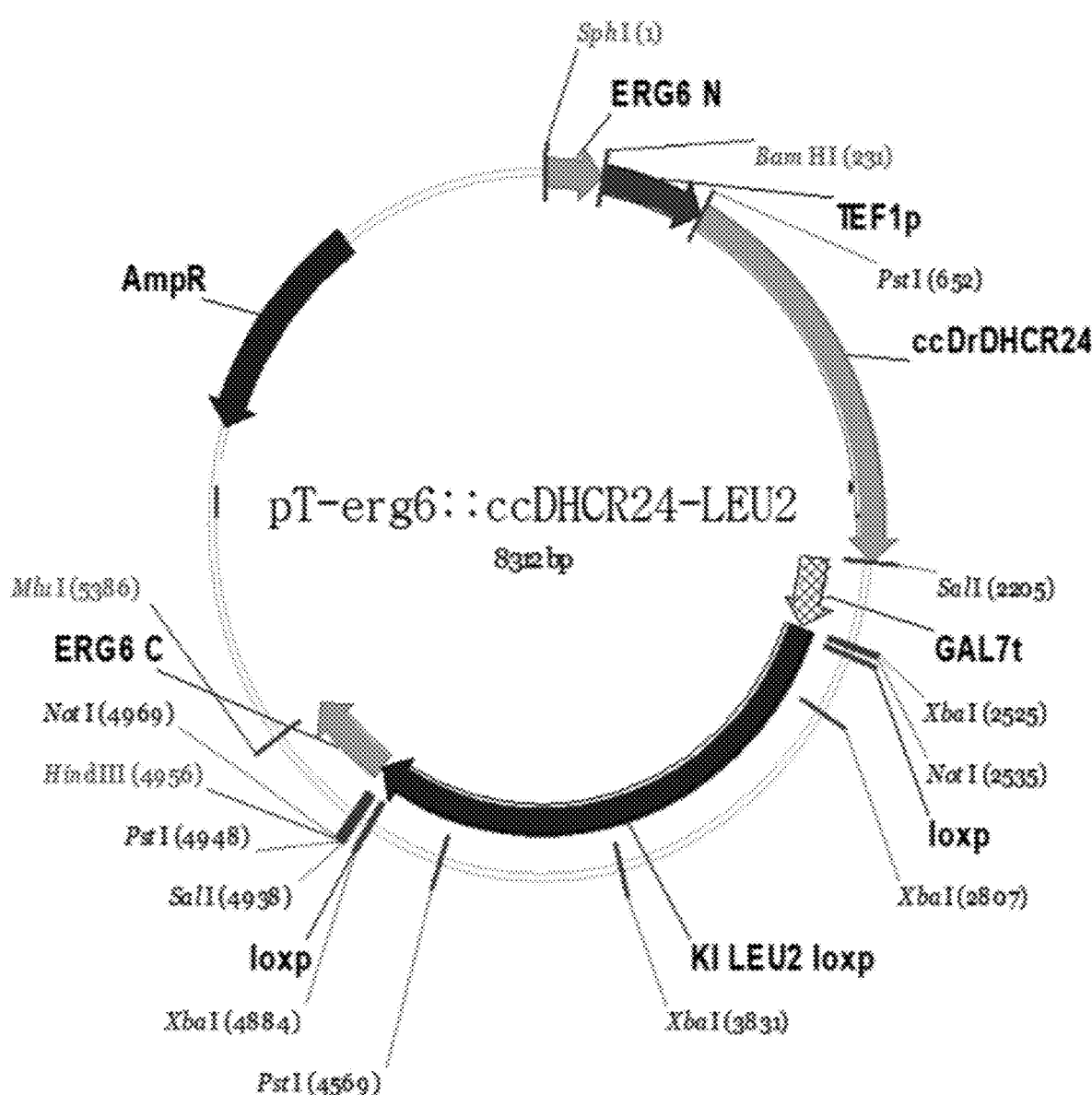
Figure 13E:
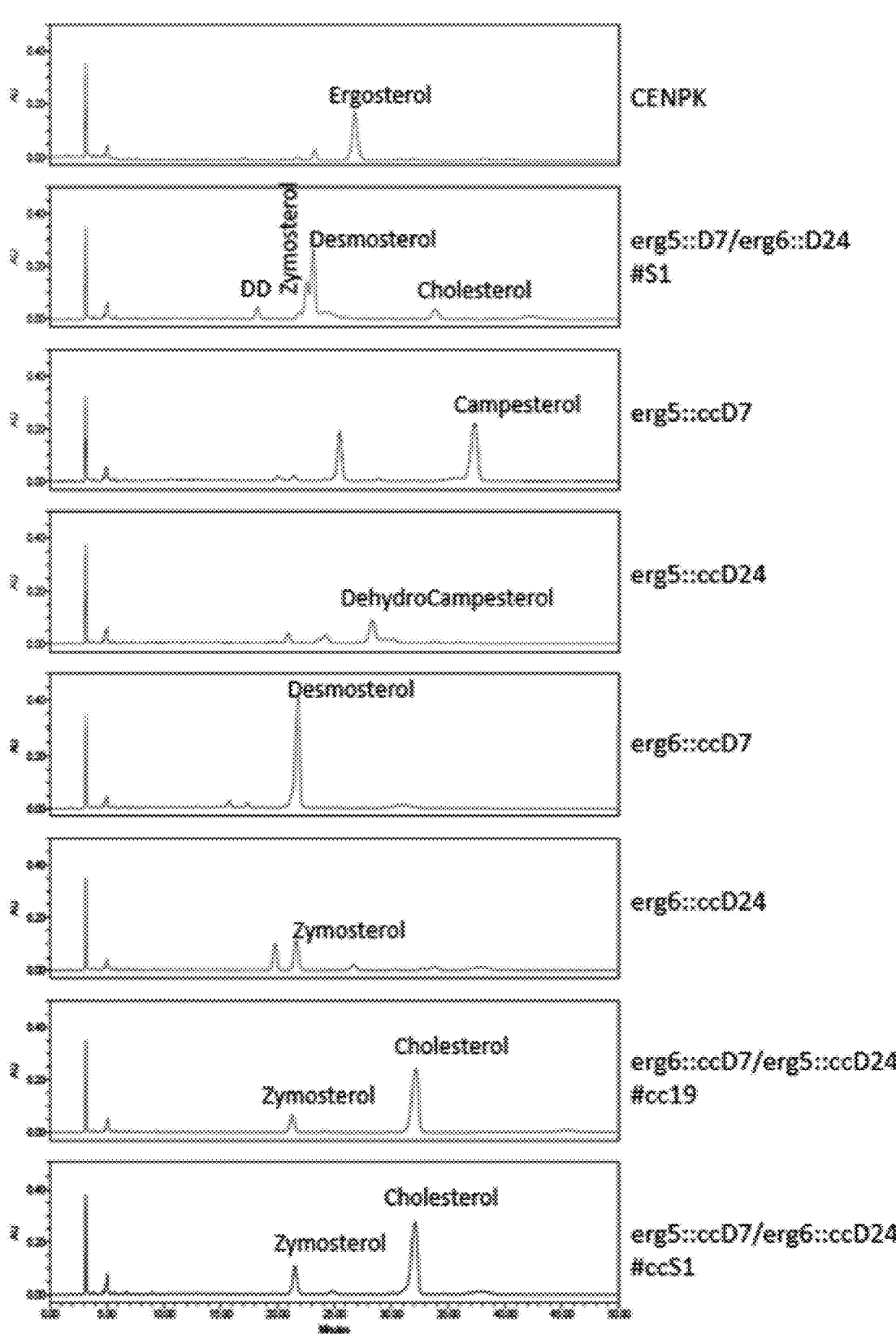

FIGS. 13A to 13E shows the result of comparative analysis of recombinant yeast strains according to one embodiment of the present invention: FIGS. 13A to 13D are vectors including a cassette used in the production of recombinant strains #cc19 and #ccS1; and FIG. 13E is the result of analyzing the production amounts of cholesterol and precursors thereof of recombinant strains #cc19 and #ccS1.

Figure 4A:
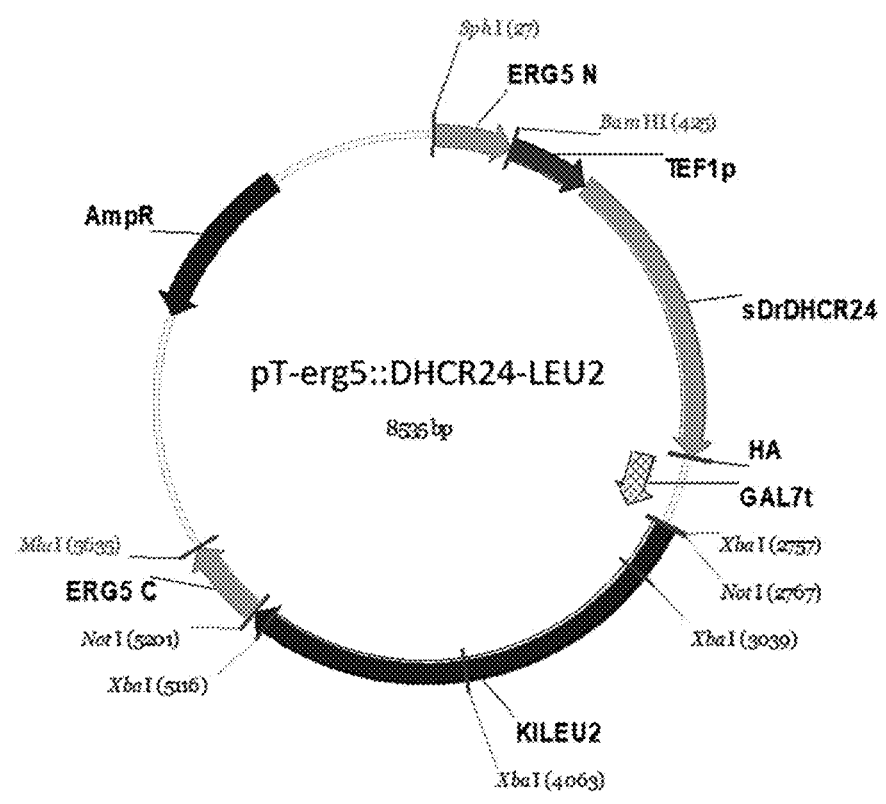
FIGS. 4A to 4J shows vectors used in preparation of recombinant yeast strains according to one embodiment of the present invention.
Figure 4B:
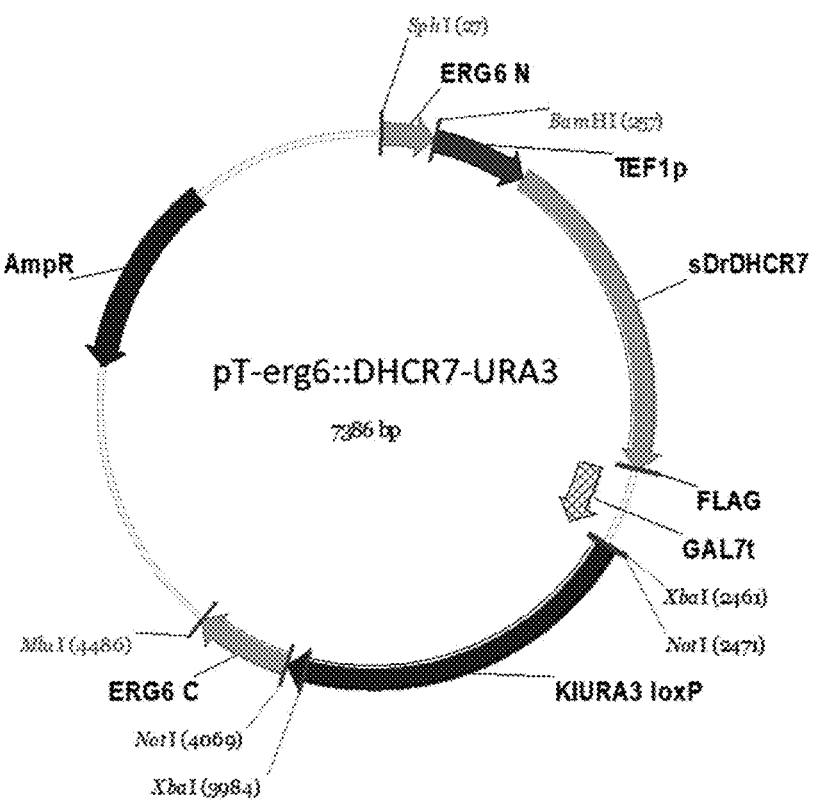
Figures 4C, 4D:
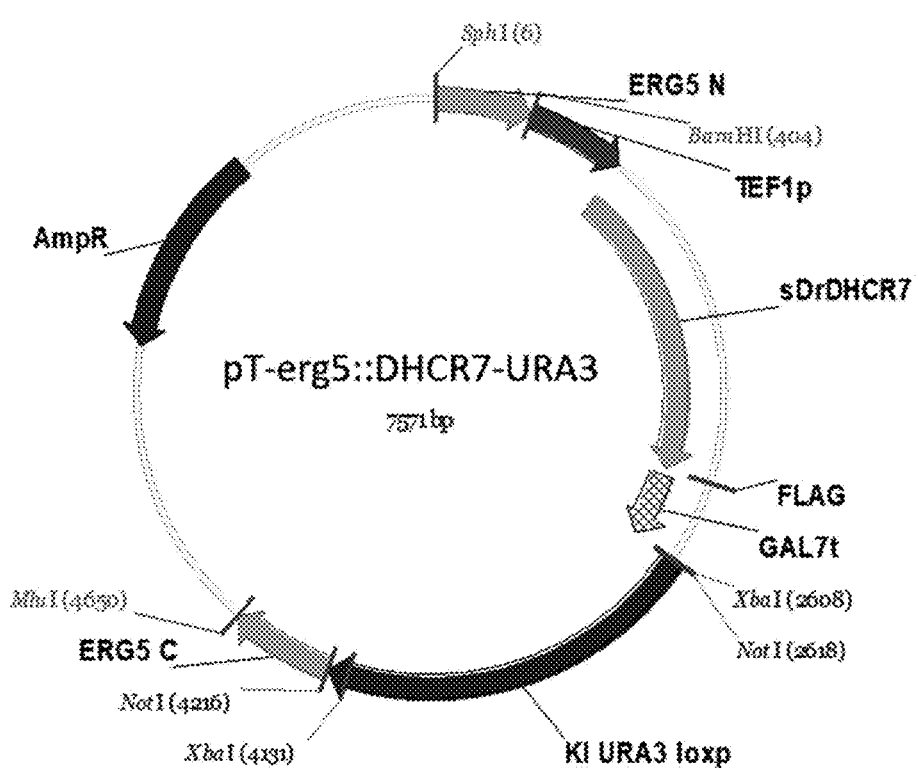
Figure 4E:
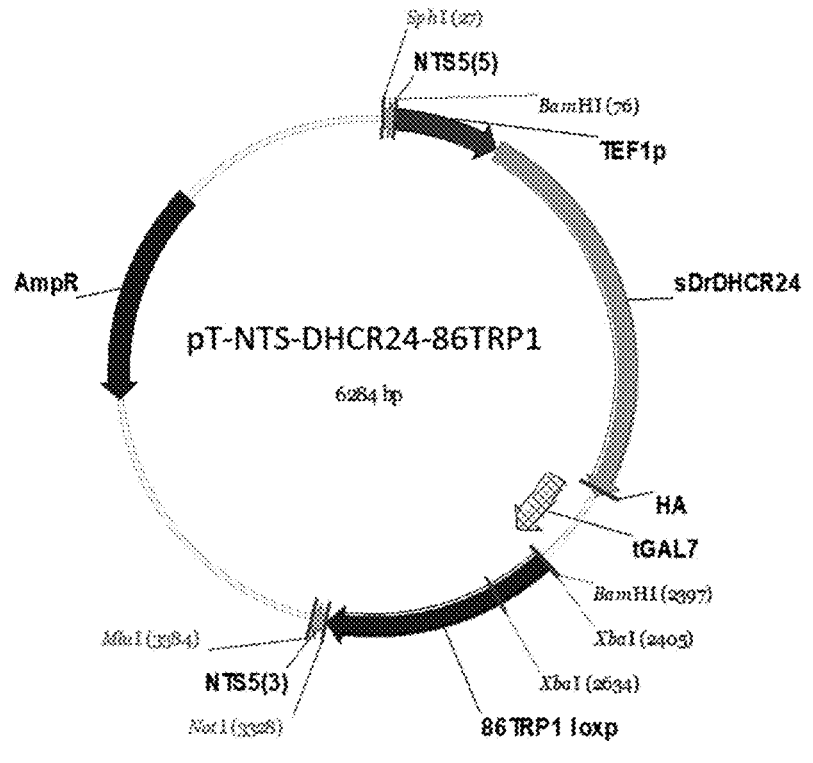
Figure 4F:
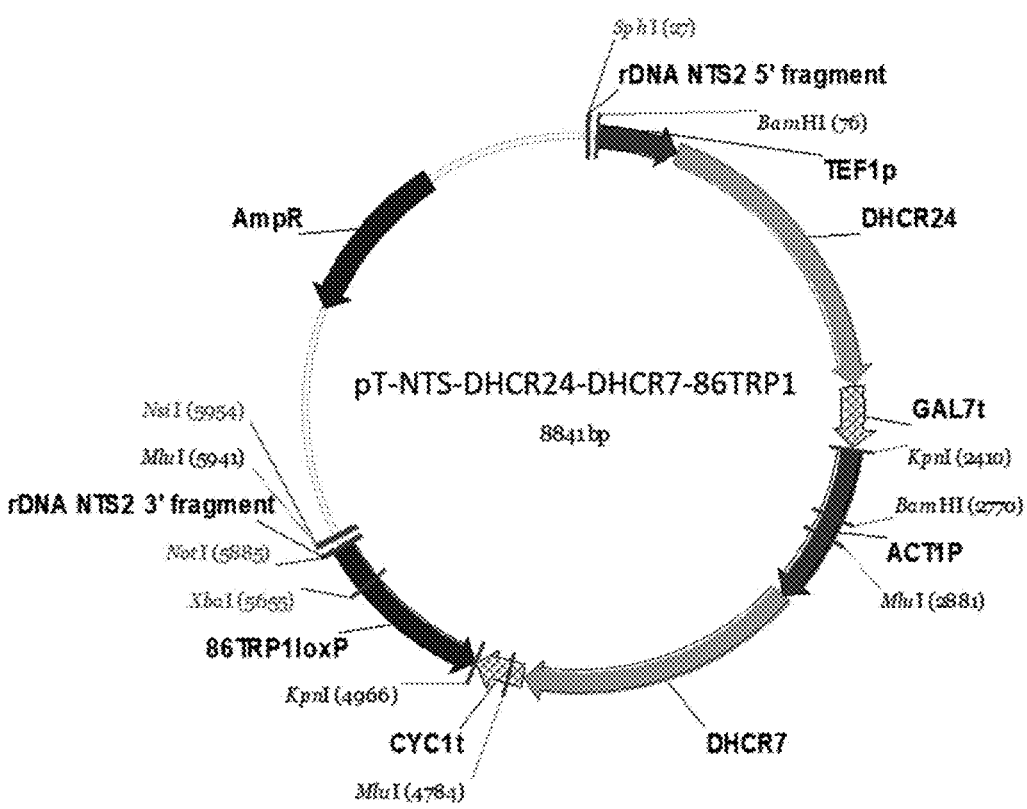
Figure 4G:
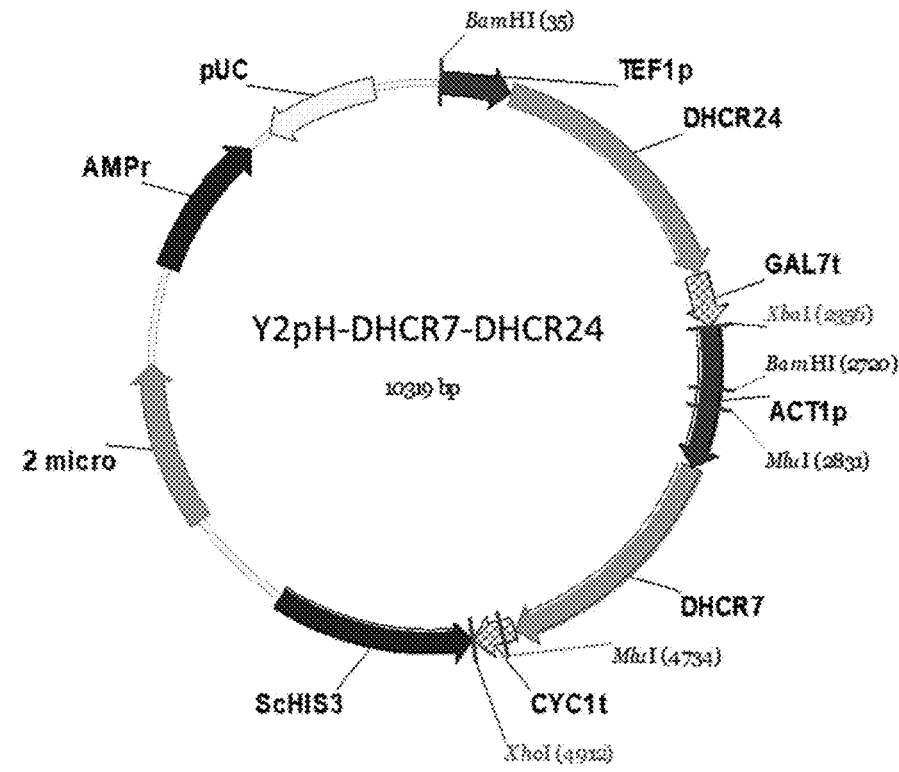
Figure 4H:
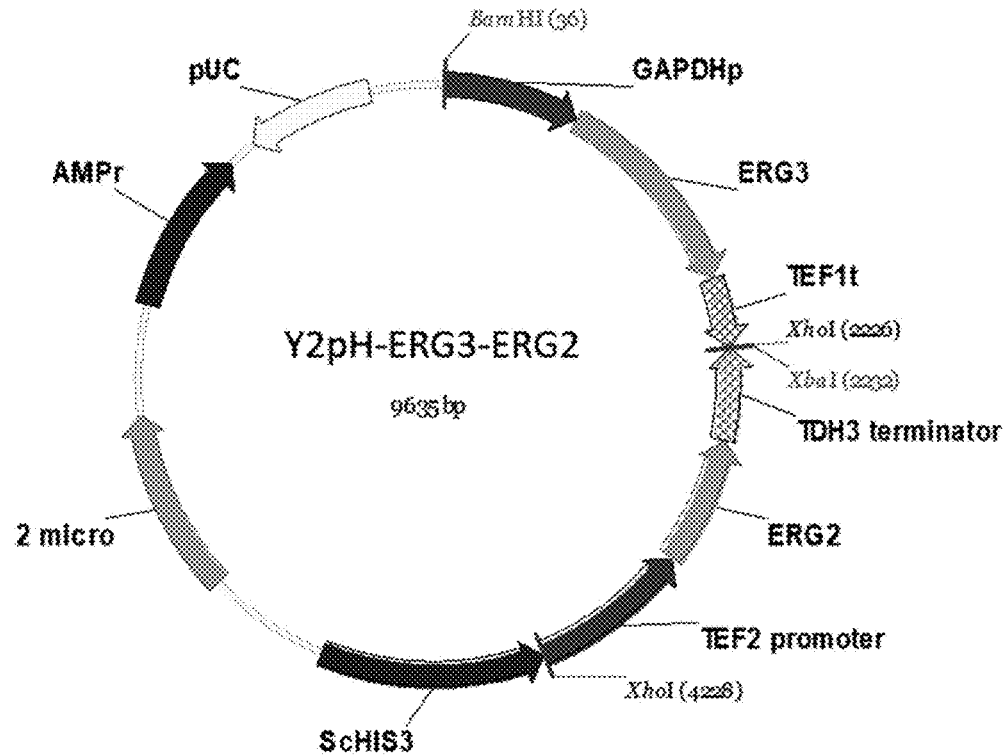
Figure 4I:
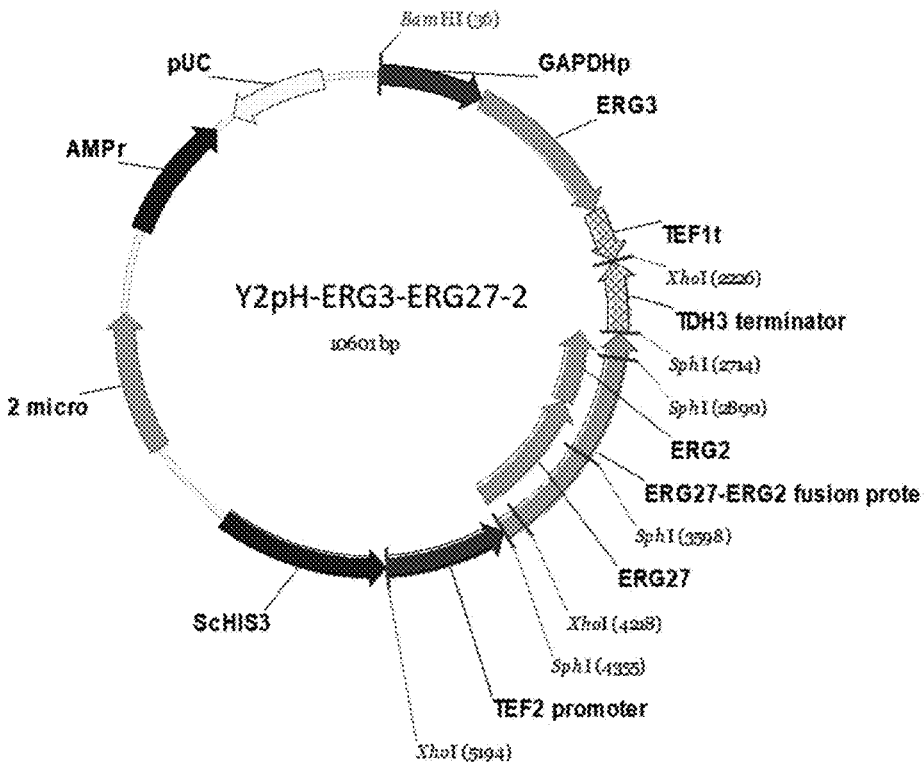
Figure 4J:
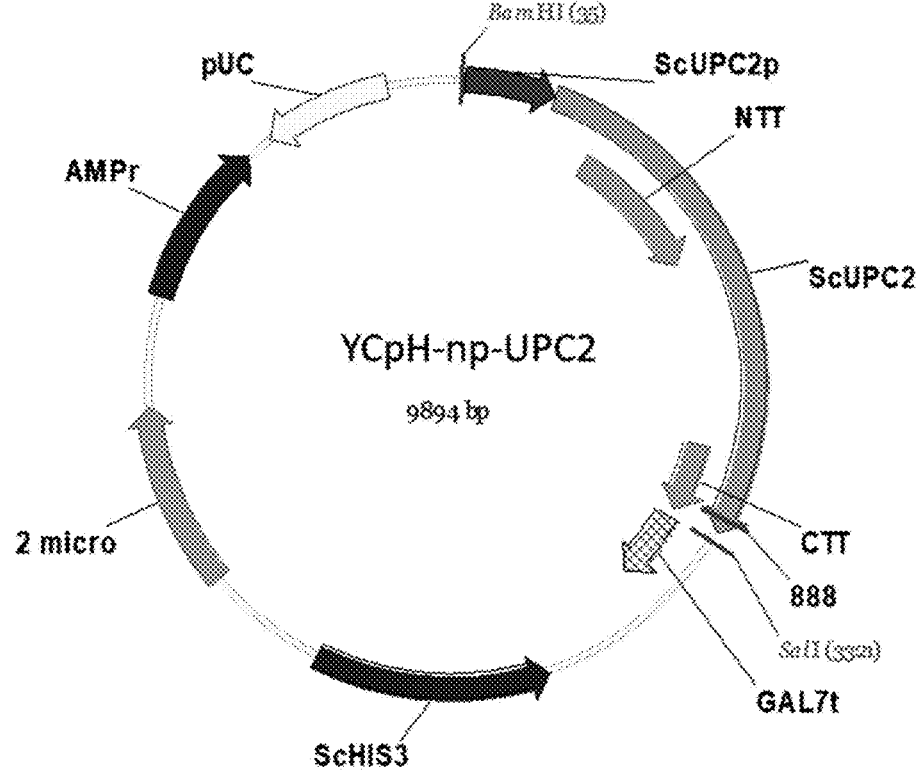
Figure 14A:
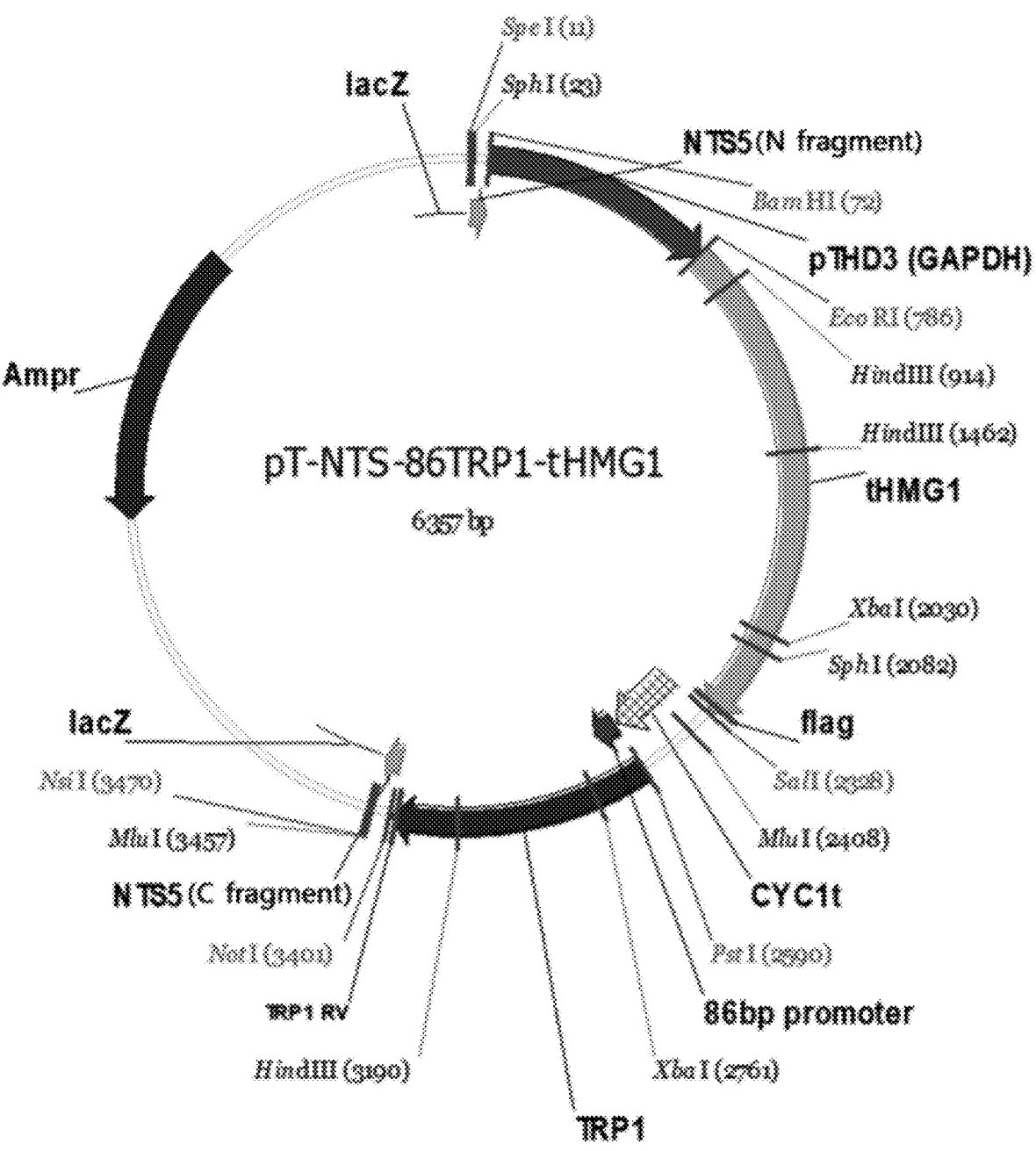
Figure 14B:
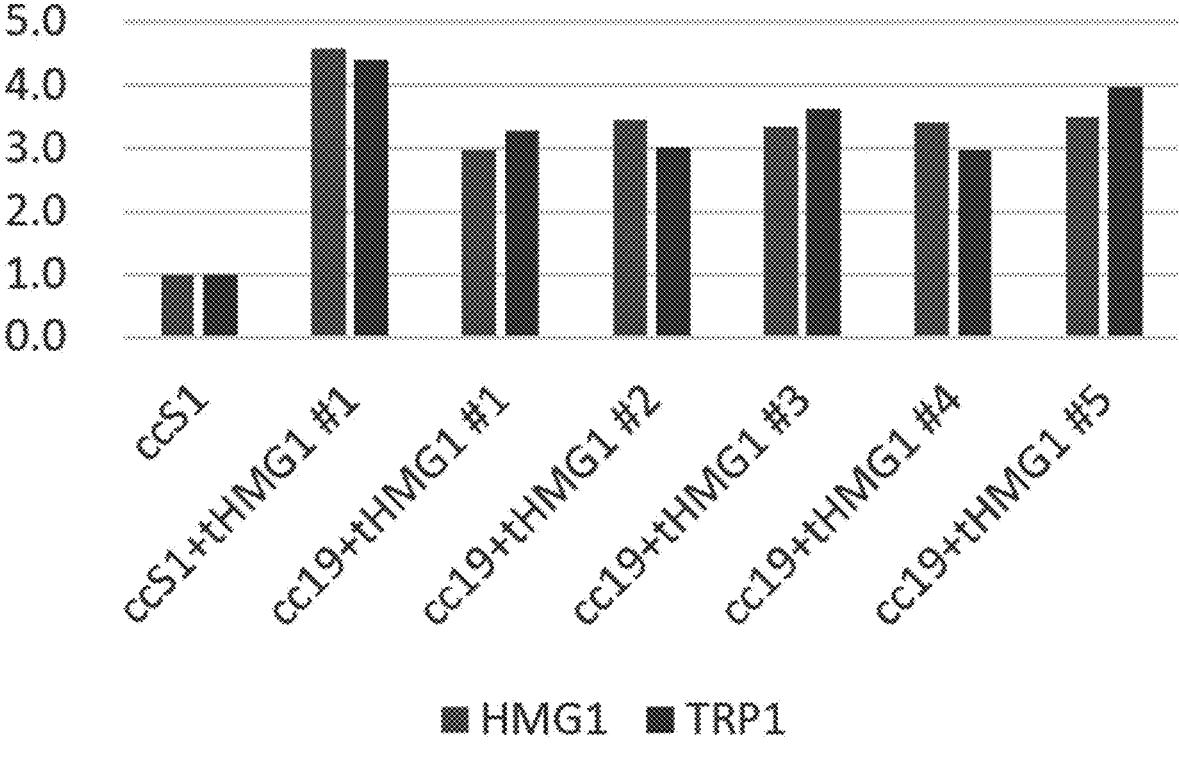
Figure 14C:
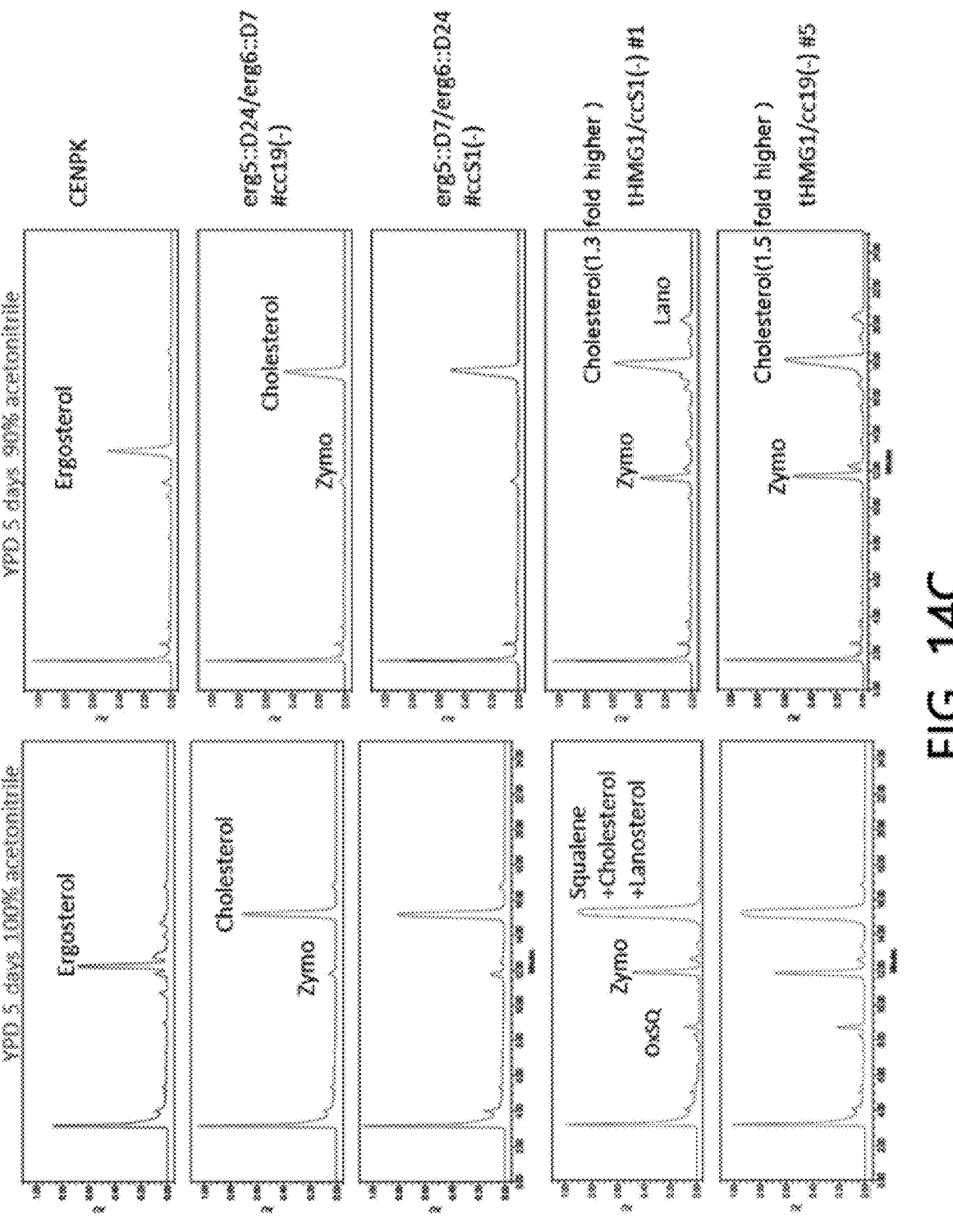

FIGS. 14A to 14C shows the result of comparative analysis of the characteristics of recombinant yeast strains according to one embodiment of the present invention: FIG. 14A shows a vector including a multiple tHMG1 integration cassette used in the production of recombinant strains tHMG1/#cc19 and tHMG1/#ccS1; FIG. 4B shows the analysis result (qPCR) according to the number of multiple tHMG1 integration cassettes of recombinant strains tHMG1/#cc19 and tHMG1/#ccS1; and FIG. 4C shows the analysis result (HPLC-UV/Vis chromatogram) for the production amounts of cholesterol and precursors thereof of recombinant strains tHMG1/#cc19 and tHMG1/#ccS1.

MODES OF THE INVENTION

Hereinafter, the present invention will be described in further detail with reference to exemplary embodiments.

The objects, features and advantages of the present invention are easily understood through the following exemplary embodiments. The present invention is not limited to the exemplary embodiments to be described below, but may be embodied in other forms. The exemplary embodiments presented herein are provided such that the idea of the present invention can be fully conveyed to those of ordinary skill in the art to which the present invention belongs. Therefore, the present invention should not be limited by the following exemplary embodiments.

Figure 1:
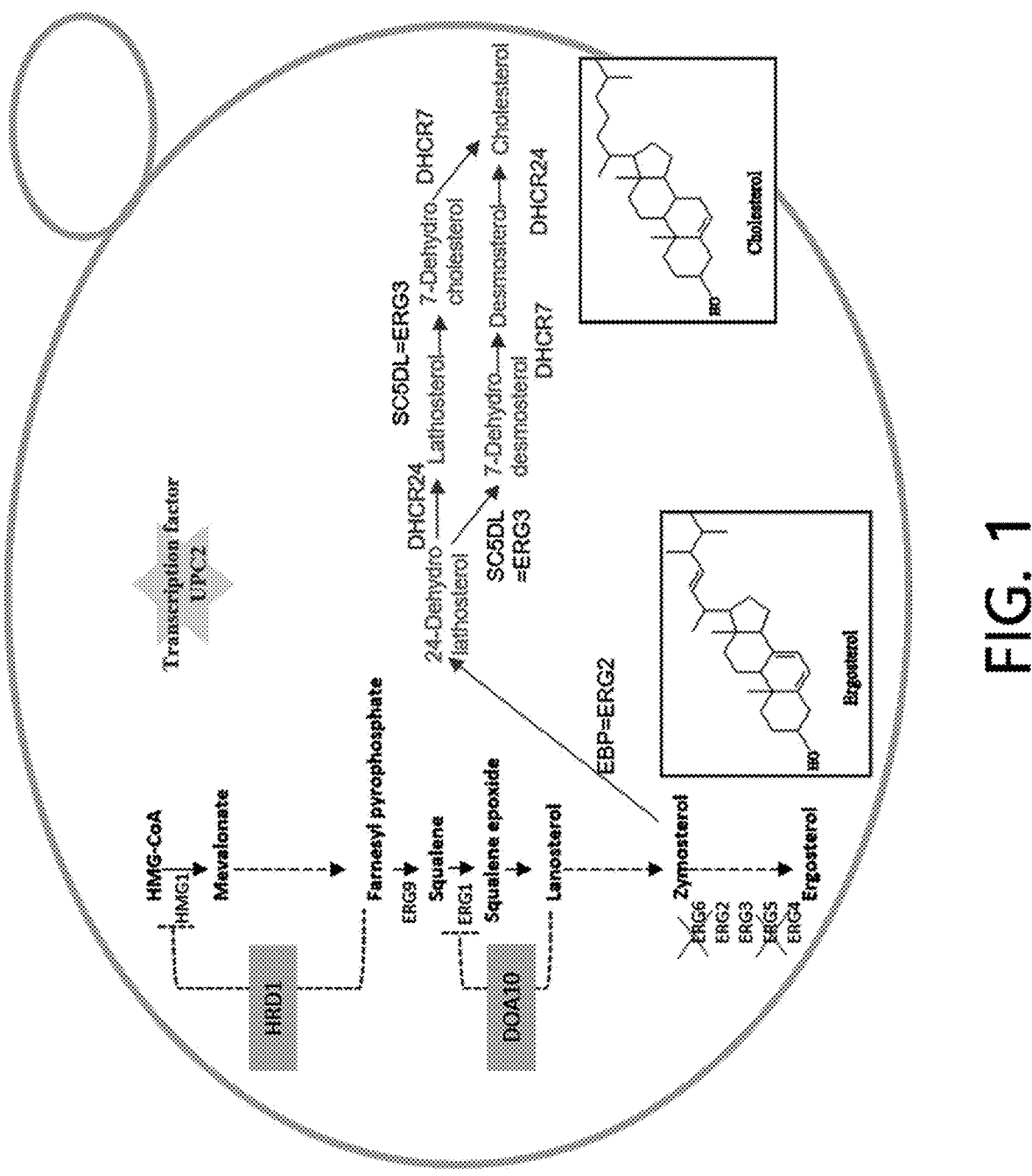
FIG. 1 shows the cholesterol biosynthesis pathway of a recombinant yeast strain according to one embodiment of the present invention.
Figure 2A:
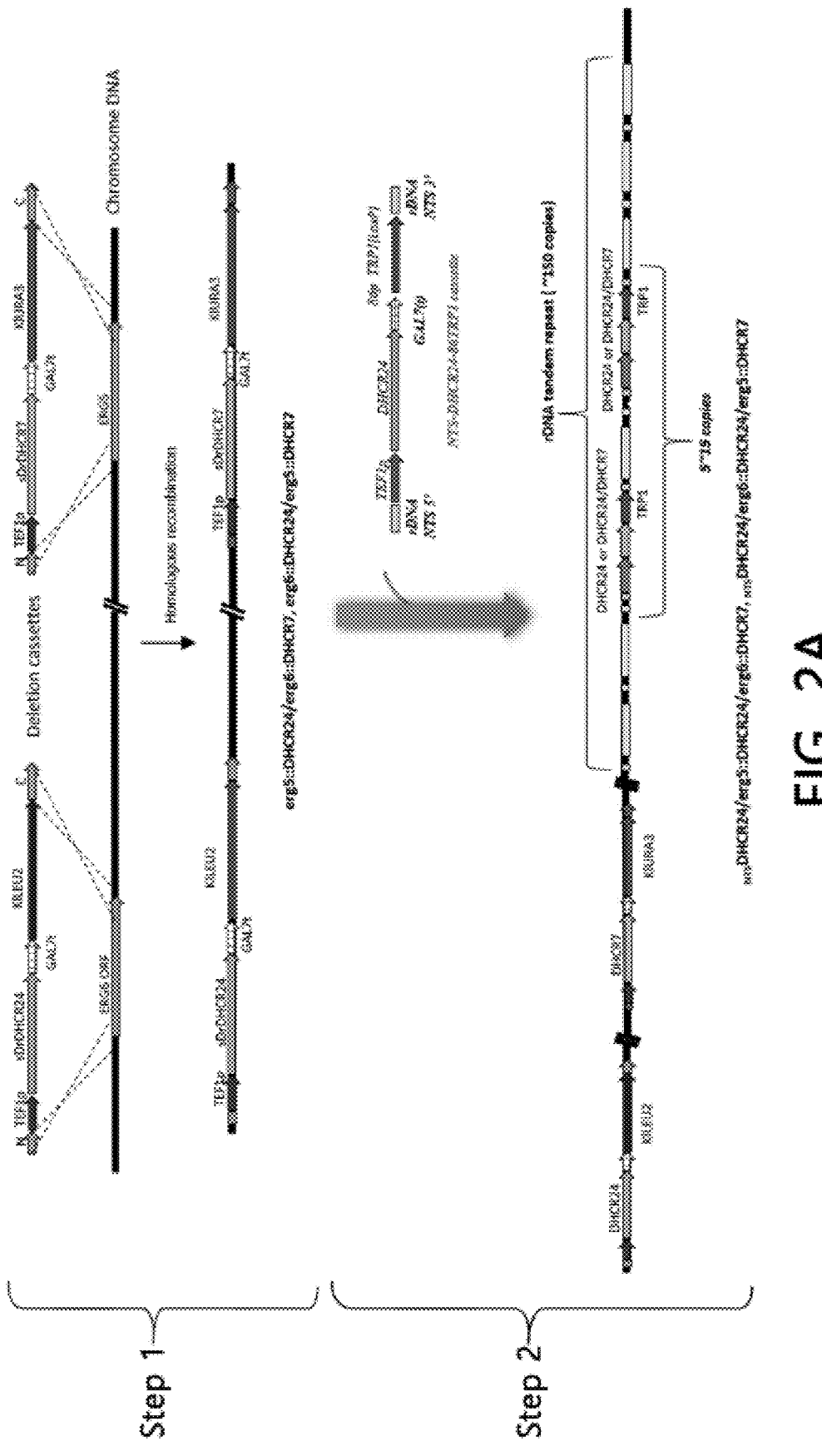
FIGS. 2A and 2B shows a process of preparing a recombinant yeast strain according to one embodiment of the present invention.
Figure 2B:
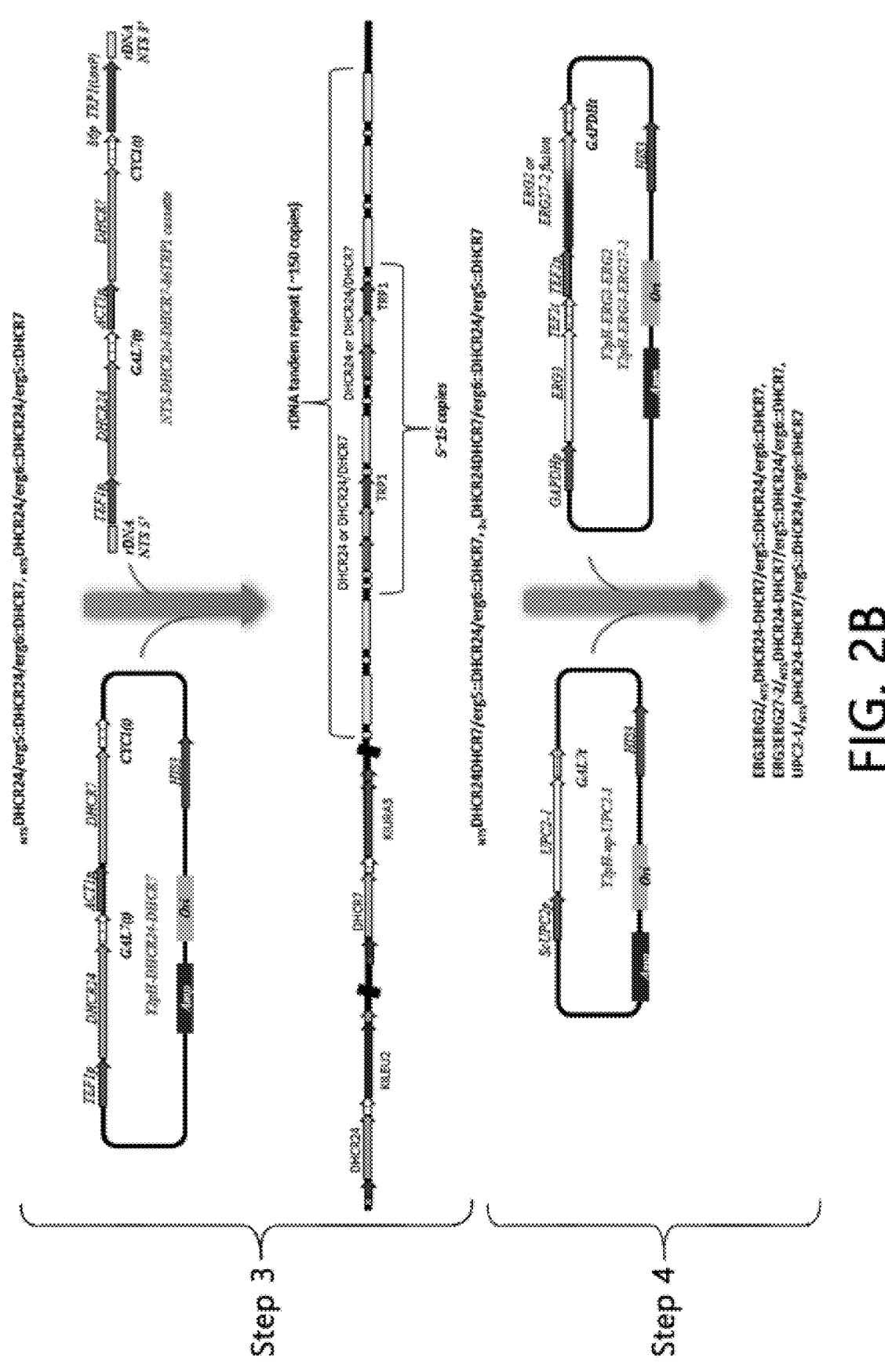
Figure 3A:
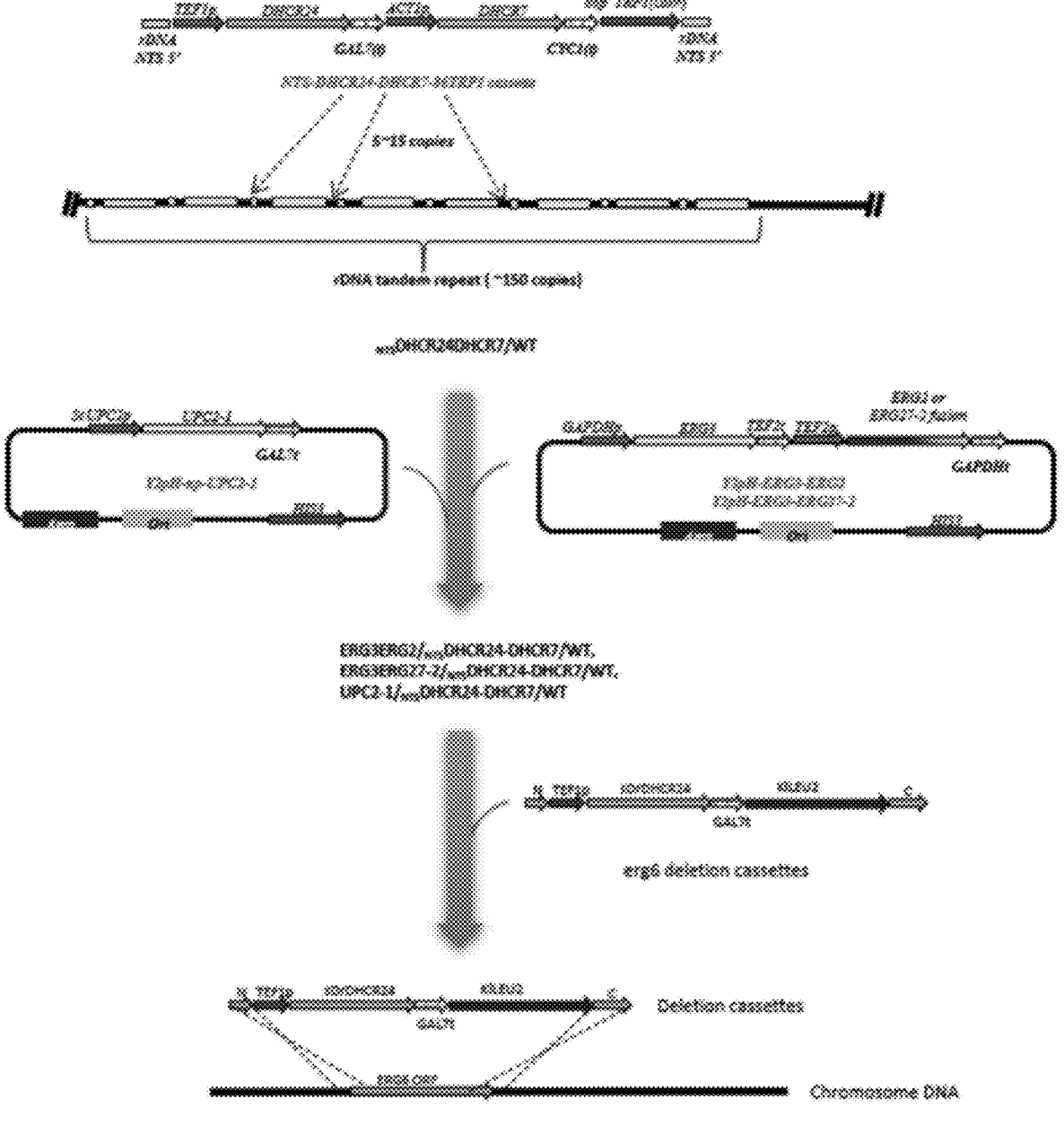
FIGS. 3A and 3B shows a process of producing a recombinant yeast strain according to one embodiment of the present invention.
Figure 3B:
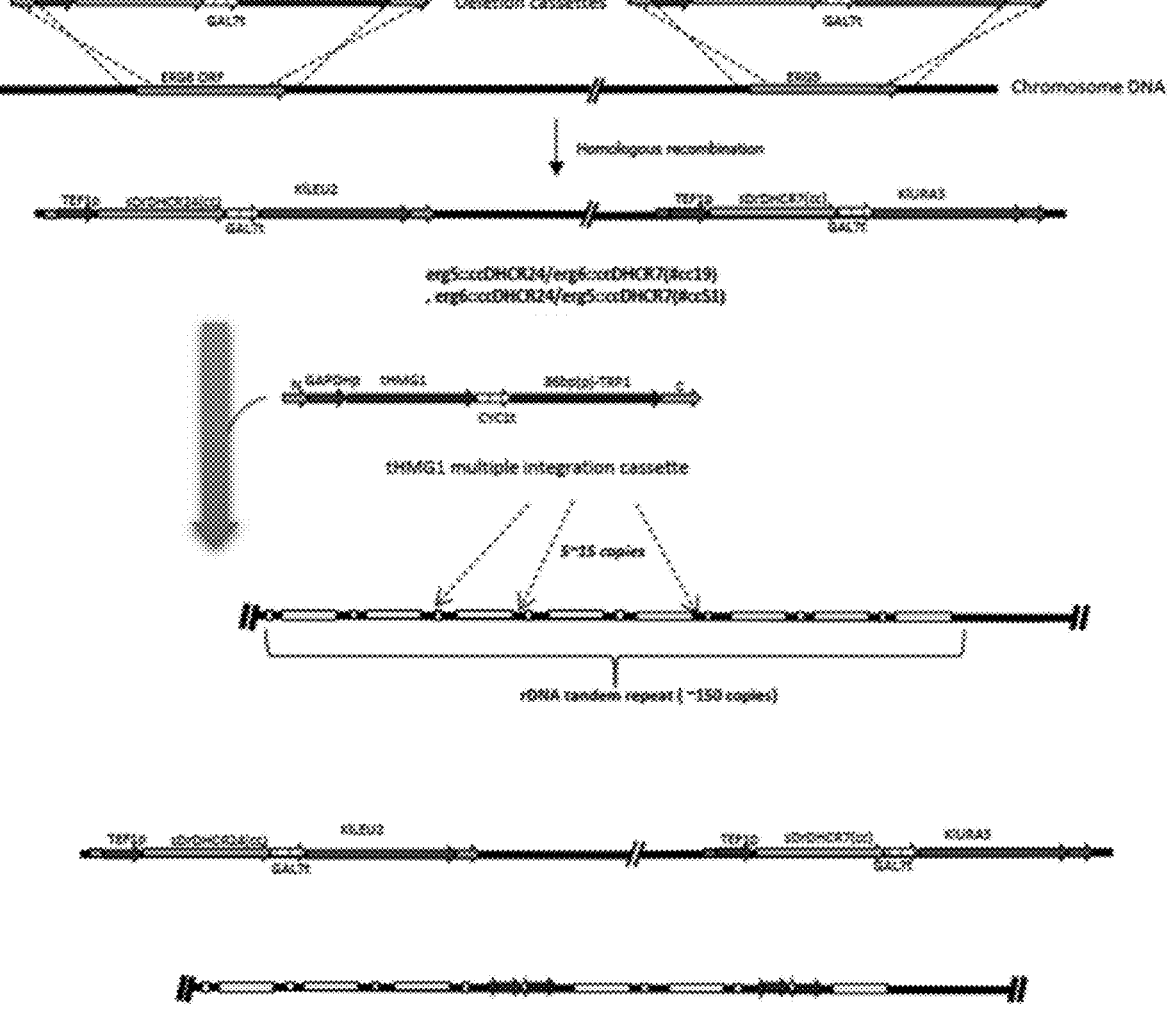

This embodiment was carried out to prepare a recombinant yeast strain that produces cholesterol and precursors thereof of an animal cell, instead of ergosterol, which is a yeast-specific sterol. To this end, a recombinant yeast strain having a cholesterol biosynthesis pathway was prepared by blocking the final ergosterol biosynthesis step for traditional baking yeast *Saccharomyces cerevisiae* and introducing a cholesterol biosynthesis-related foreign gene (FIG. 1). As a specific strategy of this embodiment, recombinant *Saccharomyces cerevisiae* (*S. cerevisiae*) strains were prepared by disrupting C22 sterol desaturase gene ERG5 involved in the formation of a 22-carbon double bond, which is an ergosterol-specific structure, and delta(24)-sterol C-methyl transferase gene ERG6 involved in 24carbon methylation, and introducing 7-dehydrocholesterol reductase gene DHCR7 and 24-dehydrocholesterol reductase gene DHCR24, which are derived from animal cells required for cholesterol production, into yeast hosts in various forms (FIG. 2A). In addition, further, in order to more effectively convert an ergosterol biosynthesis pathway into a cholesterol precursor biosynthesis pathway, it was attempted to prepare recombinant strains into which delta(7)-sterol 5(6)-desaturase (ERG3), C8 sterol isomerase (ERG2) and 3-keto-steroid reductase (ERG27), and uptake control protein 2-1 (UPC2-1), which is a transcription factor for regulating an ergosterol biosynthesis pathway, are additionally introduced (FIG. 2B). As another method, cholesterol-producing strains were prepared by first integrating multiple copies of DHCR7 and DHCR24 genes into a wild-type strain background, additionally introducing ERG3, ERG2, ERG27, and UPC2-1, which is a transcription factor for regulating an ergosterol biosynthesis pathway, and disrupting ERG6 (FIG. 3A). Furthermore, to amplify a mevalonate biosynthesis pathway, which is a precursor biosynthesis pathway of an ergosterol biosynthesis pathway, multiple copies of a tHMG1 gene were additionally introduced onto a host chromosome (FIG. 3B).

The ERG5, ERG6, DHCR7, DHCR24, ERG3, ERG2, ERG27, ARE2, ERG27-ERG2, UPC2-1 and tHMG1 may consist of sequences represented by SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 19, respectively.

```
ERG27-ERG2 fusion gene sequence
(SEQ ID NO: 15, underlined: ERG2 region)
ttaaaactaaaaccccccatt ccaaccaattacatgttcgat ccaaaaactttgaacgaaatatgtaactcggtgattagcaa acacaacgcagcagaaggtttatccactgaagacctgttac aggatgtcagagacgcacttgcctctcattacggggacgaa tacatcaacaggtacgtcaaagaagaatgggtcttcaacaa tgctggtggtgcgatgggccaaatgatcatcctacacgctt
```

7

-continued

*ccgtatccgagtacttaattctattcggaaccgctgttggt*

*actgaagggcacacaggtgttcactttgctgacgactattt*

*taccatcttacatggtacgcaaatcgcagcattgccatatg*

*ccactgaagccgaagtttacactcctggtatgactcatcac*

*ttgaagaagggatacgccaagcaatacagcatgccaggtgg*

*ttcctttgcccttgaattggctcaaggctggattccatgta*

*tgttgccattcgggtttttggacactttctccagtactctt*

*gatttatacactctatatagaactgtctacctgactgccag*

*ggacatgggtaagaacttgttgcaaaacaaaaagttctaa*

UPC2-1 sequence (SEQ ID NO: 16, underlined
capital letters: G888D point mutation
site (GGT to GAT)

attattaagagaagctgttttagaaatatctgagaataaca ccgatgcgctagttgccagcgccctgatactaatcatggac tcgttagcaaatgctagtggtaacggcactgtaggaaacca aagtttgaatagcatgtcaccaagcgcttggatctttcatg tcaaaggtgctgcaacaattttaaccgctgtgtggcctttg agtgaaagatctaaatttcataacattatatctgttgatct tagcgatttaggcgatgtcattaaccctgatgttggaacaa ttactgaattggtatgtgttttgatgaaagtattgccgatttg tatcctgtcggcttagattcgccatatttgataacactagc ttatttagataaattgcaccgtgaaaaaaaccagggtgatt ttattctgcgggtatttacatttccagcattgctagacaag acattcctggcattactgatgacaggtgatttaggtgcaat gagaattatgagatcatattataaactacttcgaggatttg ccacagaggtcaaggataaagtctggtttctcgaaggagtc acgcaggtgctgcctcaagatgttgacgaatacagtggagg tggtGATatgcatatgatgctagatttcctcggtggcggat taccatcgatgacaacaacaaatttctctgatttttcgtta Hereinafter, the present invention will be described in further detail with reference to specific examples.

EXAMPLES

Materials

Primers, expression vectors and yeast strains used in the examples are listed in Tables 1 to 3. The expression vectors constructed in the examples are listed in the diagram in FIG. 4, and media and reagents used are as follows.

Synthetic Complete medium (SC medium): 0.67% yeast nitrogen base without amino acids) (BD, 291940), 2% glucose (JUNSEI, 64220S0650), and 0.77 g/L of a drop-out amino acid mixture supplemented with all required amino acids (CLONTECH, 630425)

In-fusion cloning kit (TAKARA 121416)

KOH (JUNSEI, 39040-0350/Sigma, P1767)

Ethanol (MERCK, 1.00983.1011)

Methanol (B&J, AH230-4)

Heptane (SIGMA, 246654)

Petroleum ether (B&J, 317-4)

8

Pyrogallol (TCI, P0570)

Acetone (SIGMA, 650501)

Cosmosil C18-PAQ (4.6 mm*250 mm) column

HPLC acetonitrile (FISHER, A998-4)

HPLC water (FISHER, W5-4)

Standard cholesterol precursor for HPLC

Lanosterol (SIGMA, L5768)

Ergosterol (SIGMA, 45480-10g-f)

Zymosterol (AVANTI, 700068P)

Desmosterol (SIGMA, D6513)

Cholesterol (SIGMA, C8667)

Lathosterol (SIGMA, C3652)

7-Dehydrodesmosterol (AVANTI, 700138P)

7-Dehydrocholesterol (SIGMA, 30800)

Glucose Bio (Roche, 06343732001)

Acetate V2 Bio (COWIE, 7395442001)

Ethanol Bio (Roche, 8055645001)

Apparatus

HPLC (Waters Separations Module 2695, Waters Dual λ Absorbance Detector 2487)

PCR cycler (Eppendorf, AG 22331)

Bead beater (BERTIN TECHNOLOGY, PrecellysR24)

Water bath (TAITEC, SDN-B)

Centrifuge (Eppendorf, 5424R)

Rotational vacuum concentrator (CHRIST, RVC 2-25 CD plus)

HPLC-CAD system (Thermo Scientific, Dionex Ultimate 3000-Corona Veo RS)

Bioprocess analyzer (Roche, Cedex Bio)

[TABLE 1]

| Primers used in this experiment | |
| --- | --- |
| Primer | Sequence (5'->3') |
| erg5 dN fw | ACATGCATGCCGCTATTG AAGAGAGCTCATG (SEQ ID NO: 20) |
| erg5 dN rv | GCGGCCGCGGGTCTAGAG GGGGATCCCCAGGATACT GAAGGCAGTAG (SEQ ID NO: 21) |
| erg5 dC fw | GGATCCCCCTCTAGACCC GCGGCCGC CATGATTAC CTTCGCCGCTTTG (SEQ ID NO: 22) |
| erg5 dC rv | CGACGCGT GCTGGCAGG GTGAGTATTTG (SEQ ID NO: 23) |
| erg6 dN fw | ACGTGCATGCGCTGTTGC CGATAACTTCTTC (SEQ ID NO: 24) |
| erg6 dN rv | GCGGCCGCGGGTCTAGAG GGCTCGAGGGGGGATCC CTCAATTCTGTTTCACT CATC (SEQ ID NO: 25) |
| erg6 dC fw | GGATCCCCCCTCGAGCCC TCTAGACCCGCGGCCGCC CTCCCAAACTTCCCAAG (SEQ ID NO: 26) |
| erg6 dC rv | CGACGCGTCTTGCCGCTG TAGACAATAG (SEQ ID NO: 27) |

[TABLE 1]-continued

Primers used in this experiment

| Primer | Sequence (5'->3') |
|--------|-------------------|
| DHCR7 fw | AACTGCAGATGATGGCCT CCGATAGAGTTAG (SEQ ID NO: 28) |
| DHCR7 rv | GCGTCGACTTACTTGTC GTCATCGTCTTTGTAGT CAAAGATGTTTGGCAAT AATCTATAGG (SEQ ID NO: 29) |
| DHCR24 fw | AACTGCAGATGGACCCT TTGTTGTATTTGGG (SEQ ID NO: 30) |
| DHCR24 rv | GCGTCGACTTACGCATA GTCAGGAACATCGTATG GGTAGTGTCTGGCGGAT TTACAG (SEQ ID NO: 31) |
| TEF1p fw | CCG CTCGAG AGCTC ATAGCTTCAAAATGTT TC (SEQ ID NO: 32) |
| TEF1p rv | GC TCTAGA GGGGAA ACTTAAAGAAATTC (SEQ ID NO: 33) |
| GAL7t fw | ACGC GTCGAC TTGA ACGAAACTTGAACGGA G (SEQ ID NO: 34) |
| GAL7t rv | GC TCTAGA GGGGAA ACTTAAAGAAATTC (SEQ ID NO: 35) |
| ACT1p fw | CGAAGTTATTAGGGCGGCCGC TTTGGACTCCACCAACGTC (SEQ ID NO: 36) |
| ACT1p rv | ATCGGAGGCCATCATTGTTA ATTCAGTAAATTTTCGATCT TGGG (SEQ ID NO: 37) |
| DHCR7 fw2 | TGAATTAACAATGATGGCCT CCGATAGAGTTAG (SEQ ID NO: 38) |
| DHCR7 rv2 | CTTTAATTTGCGGCCTTACT TGTCGTCATCGTCTTTG (SEQ ID NO: 39) |
| CYC1t fw | GATGACGACAAGTAAGGCCG CAAATTAAAGCCTTC (SEQ ID NO: 40) |
| CYC1t rv | ACCTCTGGCGCGGCCTCATG TAATTAGTTATGTCACGC (SEQ ID NO: 41) |
| TDH3p fw | CGCGGATCCGTAGAATCATT TTGAATAAAAAACACGC (SEQ ID NO: 42) |
| TDH3p rv | ACTTCTAAGACCAAATCCATGA ATTCTGTTTATGTGTGTTTAT T CGAAAC (SEQ ID NO: 43) |
| ERG3 fw | ACTTCTAAGACCAAATCCATGA ATTCTGTTTATGTGTGTTTT T CGAAAC (SEQ ID NO: 44) |

[TABLE 1]-continued

Primers used in this experiment

| Primer | Sequence (5'->3') |
|--------|-------------------|
| ERG3 rv | AGAAAGTCTTATCAATCTCCG TCGACTCAGTTGTTCTTCTT G GTATTTG (SEQ ID NO: 45) |
| TEF1t fw | CAAATACCAAGAAGAACAACT GAGTCGACGGAGATTGATAA G ACTTTTCT (SEQ ID NO: 46) |
| TEF1t rv | CCGCTCGAGGTAAAAAATAC GCCCGTAACGATG (SEQ ID NO: 47) |
| TEF2p fw | CCGCTCGAGTGCCATTAAAG GCGAATTTTTG (SEQ ID NO: 48) |
| TEF2p rv | AAGGAGTGGGAAAAACTTCAT GCATGCGTTTAGTTAATTAT A GTTCGTTG (SEQ ID NO: 49) |
| ERG2 fw | CAACGAACTATAATTAACTA AACGCATGCATGAAGTTTTT CCC ACTCCTT (SEQ ID NO: 50) |
| ERG2 rv | AGATTTAAAGTAAATTCACG CATGCTTAGAACTTTTTGT TTTG CAACAAG (SEQ ID NO: 51) |
| TDH3t fw | CTTGTTGCAAAACAAAAAGTTC TAAGCATGCGTGAATTTACT T TAAATCT (SEQ ID NO: 52) |
| TDH3t rv | CCGCTCGAGTCTAGATATATGT TATCTTATCTTGG (SEQ ID NO: 53) |
| ERG27-2 fw1 | CGAACATGTAATTGGTTGGAAT GGGGGTTCTAGTTTCAACA AT TTG (SEQ ID NO: 54) |
| ERG27-2 rv1 | CTATAATTAACTAAACGCATG CATGAACAGGAAAGTAGCTA T CGTAAC (SEQ ID NO: 55) |
| ERG27-2 fw2 | AAGATTTAAAGTAAATTCACG CATGCTTAGAACTTTTTGTTT TGCAACAAGTTC (SEQ ID NO: 56) |
| ERG27-2 rv2 | GTTGAAACTAGAACCCCATT CCAACCAATTACATGTTCGAT C C (SEQ ID NO: 57) |
| ARE2dN fw1 | ACAT GCATGCCAAGTCGTA AACCTCGTCGG (SEQ ID NO: 58) |
| ARE2dN rv1 | GATATCGCGCTCGAGGTTCT CCAGTAGATCCTTCTTC (SEQ ID NO: 59) |
| ARE2dN fw2 | CTCGAGCGCGATATCGGACC AAGTGTCATGTGTACG (SEQ ID NO: 60) |

[TABLE 1]-continued

| Primers used in this experiment | |
|---|---|
| Primer | Sequence (5'->3') |
| ARE2 dN rv2 | CCG ACGCGTGGCAAATAGATT GGTTAAATCTGAAG (SEQ ID NO: 61) |
| 101HIS fw | GCTATACGAAGTTATTAGGCCC GGGGATTGGCATTATCACATA ATGAATTATAC (SEQ ID NO: 62) |
| 101HIS rv | CACCTTGAAACTACCTCTGGCG CGGCCGCTCGAGTTCAAGAGA AAAAAAAGAAAAAGCAAAA AG (SEQ ID NO: 63) |
| ccD7 fw | CTAATCTAAGTTTTCTAGCTG CAGATGATGGCCTCTGACAG AGTC (SEQ ID NO: 64) |

[TABLE 1]-continued

| Primers used in this experiment | |
|---|---|
| Primer | Sequence (5'->3') |
| ccD7 rv | GTCACTCCGTTCAAGTCGACT TAGAAAATGTTTGGTAGCAA TCTGTAAG (SEQ ID NO: 65) |
| ccD24 fw | CTAAGTTTTCTAACTGCAGA TGGACCCATTGCTATACTTA GGTG (SEQ ID NO: 66) |
| ccD24 rv | CAAGTTTCGTTCAAGTCGACC TAATGTCTGGCAGATTTGCA AATCTTG (SEQ ID NO: 67) |
| tHMG1-fw | GGAATTCATGCCAGTTTTAA CCAATAA (SEQ ID NO: 68) |
| tHMG1-rv | GCGTCGACTTACGCATAGTC AGGAACATCGTATGGGTAG GATTTAATGCAGGTGACGG (SEQ ID NO: 69) |

TABLE 2

| Plasmids used in this experiment | | |
|---|---|---|
| Plasmid | Description | Reference |
| pT-ERG5dNC | pGEM-Teasy vector containing ERG5 N and C partial fragments | this study |
| pT-ERG6dNC | pGEM-Teasy vector containing ERG6 N and C partial fragments | this study |
| pMKRQ-DrDHCR24 | pMKRQ containing S. cerevisiae-codon optimized zebrafish DHCR7 | Daewoong |
| pMKRQ-DrDHCR7 | pMKRQ containing S. cerevisiae-codon optimized zebrafish DHCR24 | Daewoong |
| pUG72 | loxP-pKlURA3-KlURA3-tKlURA3-loxP | Euroscarf |
| pUG73 | loxP-pKlLEU2-KlLEU2-tKlLEU2-loxP | Euroscarf |
| pT-DHCR24 | pGEM-Teasy-pTEF1-DHCR24-GAL7t | this study |
| pT-DHCR7 | pGEM-Teasy-pACT1-DHCR7-CYC1t | this study |
| pT-erg5::DHCR24-LEU 2 | pGEM-Teasy-ERG5(N)-pTEF1-DHCR24-GAL 7t-KlLEU2-ERG5(C) | this study |
| pT-erg6::DHCR7-URA3 | pGEM-Teasy-ERG6(N)-pACT1-DHCR7-CYC1 t-KlURA3-ERG6(C) | this study |
| pT-erg6::DHCR24-LEU 2 | pGEM-Teasy-ERG6(N)-pTEF1-DHCR24-GAL 7t-KlLEU2-ERG6(C) | this study |
| pT-erg5::DHCR7-URA3 | pGEM-Teasy-ERG5(N)-pACT1-DHCR7-CYC1 t-KlURA3-ERG5(C) | this study |
| pT-NTS-86TRP1 | pGEM-Teasy-5NTS2-TRP1 with 86bp promoter-3NTS2 | Moon et. al., 2016 |
| pT-NTS-DHCR24-86TR P1 | pT-NTS-86TRP1 containing the DHCR24 expression cassette pTEF1-DHCR24-GAL7t | this study |
| pT-NTS-DHCR24-DHC R7-86TRP1 | pT-NTS-DHCR24-86TRP1 containing the DHCR7 expression cassette pACT1-DHCR7-CYC1t | this study |
| Y2pH | 2μ-based YEp351 derivative, containing the GAL10 promoter and GAL7 terminator and the HIS3 marker | this study |
| Y2pH-DHCR7-DHCR24 | Y2pH containing pTEF1-DHCR24-GAL7t and pACT1-DHCR7-CYC1t | this study |
| Y2pH-ERG3-ERG2 | Y2pH containing TDH3p-ERG3-TEF1t and TEF2p-ERG2-TDH3t | this study |
| Y2pH-ERG3-ERG27-2 | Y2pH containing TDH3p-ERG3-TEF1t and TEF2p-ERG27-ERG2 fusion-TDH3t | this study |
| YCpH-Tp | CEN-based pRE316 derivative containing the TEF1 promoter, the GAL7 terminator and the HIS3 marker | Application: 10-2017-0182422 |
| YCpH-np-UPC2 | YCpH derivative expressing UPC2-1 under the control of its own promoter | Application: 10-2017-0182422 |

TABLE 2-continued

| | | |
|---|---|---|
| | Plasmids used in this experiment | |
| Plasmid | Description | Reference |
| pT-ARE2dNC-HIS | pGEM-Teasy vector containing the ARE2 deletion cassette ARE2::HIS3 | this study |
| pT-NTS-101HIS3-DHC R7 | pT-NTS-101HIS3 containing the DHCR7 expression cassette pACT1-DHCR7-CYC1t | this study |
| pMKRQ-sDrDHCRc7(cc) | pMKRQ containing S. cerevisiae-codon context optimized DHCR7 gene from Danio rerio | this study |
| pMKRQ-sDrDHCRc24(cc) | pMKRQ containing S. cerevisiae-codon context optimized DHCR24 gene from Danio rerio | this study |
| pT-ERG5dNC-ccDHCR 7 | pGEM-Teasy-ERG5(N)-pACT1-ccDHCR7-CY C1t-ERG5(C) | this study |
| pT-ERG5dNC-ccDHCR 24 | pGEM-Teasy-ERG5(N)-pTEF1-ccDHCR24-GA L7t-KlLEU2-ERG5(C) | this study |
| pT-ERG6dNC-ccDHCR 7 | pGEM-Teasy-ERG6(N)-pACT1-ccDHCR7-CY C1t-ERG6(C) | this study |
| pT-ERG6dNC-ccDHCR 24 | pGEM-Teasy-ERG6(N)-pTEF1-ccDHCR24-GA L7t-KlLEU2-ERG6(C) | this study |
| pT-erg6::ccDHCR7-UR A3 | pGEM-Teasy-ERG6(N)-pACT1-ccDHCR7-CY C1t-KlURA3-ERG6(C) | this study |
| pT-erg6::ccDHCR24-LE U2 | pGEM-Teasy-ERG6(N)-pTEF1-ccDHCR24-GA L7t-KlLEU2-ERG6(C) | this study |
| pT-erg5::ccDHCR-UR A3 | pGEM-Teasy-ERG5(N)-pACT1-ccDHCR7-CYC1t-KlURA3-ERG5(C) | this study |
| pT-NTS-86TRP1-tHMG 1 | pT-NTS-86TRP1 containing the N-truncated HMG1 expression cassette pTEF1-tHMG1-GAL7t | this study |

TABLE 3

| | | | |
|---|---|---|---|
| | | Yeast strains used in this experiment | |
| | Strain | Genotype | Reference |
| 1 | CEN.PK (WT) | MATa ura3-52 trp1-289 leu2-3,112 his3-D1 MAL2-8C SUC2 | Entian and Kotter (2007) |
| 2 | erg5::D24 | MATa ura3-52 trp1-289 leu2-3,112 his3-D1 MAL2-8C SUC2 erg5Δ::KlLEU2-TEF1p-sDrDHCR24 | this study |
| 3 | erg6::D7 | MATa ura3-52 trp1-289 leu2-3,112 his3-D1 MAL2-8C SUC2 erg6Δ::KlURA3-TEF1p-sDrDHCR7 | this study |
| 4 | erg6::D24 | MATa ura3-52 trp1-289 leu2-3,112 his3-D1 MAL2-8C SUC2 erg6Δ::KlLEU2-TEF1p-sDrDHCR24 | this study |
| 5 | erg5::D7 | MATa ura3-52 trp1-289 leu2-3,112 his3-D1 MAL2-8C SUC2 erg5Δ::KlURA3-TEF1p-sDrDHCR7 | this study |
| 6 | erg5::D24/erg6::D 7 (#19) | MATa ura3-52 trp1-289 leu2-3,112 his3-D1 MAL2-8C SUC2 erg5Δ::KlLEU2-TEF1p-sDrDHCR24, erg6Δ::KlURA3-TEF1p-sDrDHCR7 | this study |
| 7 | erg6::D24/erg5::D 7(#S1) | MATa ura3-52 trp1-289 leu2-3,112 his3-D1 MAL2-8C SUC2 erg5Δ::KlLEU2-TEF1p-sDrDHCR7, erg6Δ::KlURA3-TEF1p-sDrDHCR24 | this study |
| 8 | $_{NTS}$D24/erg5::D24/erg6::D7($_{NTS}$D24/#19) | MATa ura3-52 trp1-289 leu2-3,112 his3-D1 MAL2-8C SUC2 erg5Δ::KlLEU2-TEF1p-sDrDHCR24, erg6Δ::KlURA3-TEF1p-sDrDHCR7, NTS-DHCR24-TRP1 | this study |
| 9 | $_{NTS}$D24/erg6::D24/erg5::D7($_{NTS}$D24/#S1) | MATa ura3-52 trp1-289 leu2-3,112 his3-D1 MAL2-8C SUC2 erg5Δ::KlLEU2-TEF1p-sDrDHCR7, erg6Δ::KlURA3-TEF1p-sDrDHCR24, NTS-DHCR24-TRP1 | this study |
| 10 | $_{NTS}$D24D7/erg5::D24/erg6::D7($_{NTS}$D24D7/#19) | MATa ura3-52 trp1-289 leu2-3,112 his3-D1 MAL2-8C SUC2 erg5Δ::KlLEU2-TEF1p-sDrDHCR24, erg6Δ::KlURA3-TEF1p-sDrDHCR7, NTS-DHCR24-DHCR7-TRP1 | this study |
| 11 | $_{2\mu}$D24D7/erg6::D24/erg5::D7($_{2\mu}$D24 D7/#S1) | MATa ura3-52 trp1-289 leu2-3,112 his3-D1 MAL2-8C SUC2 erg5Δ::KlLEU2-TEF1p-sDrDHCR7, ergΔ::KlURA3-TEF1p-sDrDHCR24/Y2pH-DH CR24-DHCR7 | this study |

TABLE 3-continued

| | | Yeast strains used in this experiment | |
|---|---|---|---|
| | Strain | Genotype | Reference |
| 12 | E3E2/$_{NTS}$D24D7/erg5:: D24/erg6::D7 | MATa ura3-52 trp1-289 leu2-3,112 his3-D1 MAL2-8C SUC2 ergΔ::KlLEU2-TEF1p-sDrDHCR24, erg6Δ::KlURA3-TEF1p-sDrDHCR7, NTS-DHCR24-DHCR7-TRP1/Y2pH-ERG3-ERG2 | this study |
| 13 | E3E27-2/$_{NTS}$D24D7/erg5:: D24/erg6:: D7 | MATa ura3-52 trp1-289 leu2-3,112 his3-D1 MAL2-8C SUC2 erg5Δ::KlLEU2-TEF1p-sDrDHCR24, erg6Δ::KlURA3-TEF1p-sDrDHCR7, NTS-DHCR24-DHCR7-TRP1/Y2pH-ERG3-ERG27-2 | this study |
| 14 | UPC2-1/$_{NTS}$D24D7/erg5::D24/ erg6::D7 | MATa ura3-52 trp1-289 leu2-3,112 his3-D1 MAL2-8C SUC2 erg5Δ::KlLEU2-TEF1p-sDrDHCR24, erg6Δ::KlURA3-TEF1p-sDrDHCR7, NTS-DHCR24-DHCR7-TRP1/Y2pH-ERG3-ERG2 | this study |
| 15 | $_{NTS}$D24D7/WT | MATa ura3-52 trp1-289 leu2-3,112 his3-D1 MAL2-8C SUC2 NTS-DHCR24-DHCR7-TRP1 | this study |
| 16 | E3E2/$_{NTS}$D24D7/WT | MATa ura3-52 trp1-289 leu2-3,112 his3-D1 MAL2-8C SUC2 NTS-DHCR24-DHCR7-TRP1/Y2pH-ERG3-ERG2 | this study |
| 17 | E3E27-2/$_{NTS}$D24D7/ WT | MATa ura3-52 trp1-289 leu2-3,112 his3-D1 MAL2-8C SUC2 NTS-DHCR24-DHCR7-TRP1/Y2pH-ERG3 ERG27ERG2 fusion | this study |
| 18 | UPC2-1/$_{NTS}$D24D7/ WT | MATa ura3-52 trp1-289 leu2-3,112 his3-D1 MAL2-8C SUC2 NTS-DHCR24-DHCR7-TRP1/Y2pH-ERG3 ERG27ERG2 fusion | this study |
| 19 | erg6::D7/UPC2-1/ $_{NTS}$D24D7 | MATa ura3-52 trp1-289 leu2-3,112 his3-D1 MAL2-8C SUC2 NTS-DHCR24-DHCR7-TRP1/Y2pH-ERG3-ERG27ERG2 fusion/erg6Δ::KlURA3-TEF1p-sDrDHCR7 | this study |
| 20 | are2Δ | MATa ura3-52 trp1-289 leu2-3,112 his3-D1 MAL2-8C SUC2 are2Δ::HIS3 | this study |
| 21 | are2Δ/$_{NTS}$D24D7/ erg5::D24/erg6::D7 | MATa ura3-52 trp1-289 leu2-3,112 his3-D1 MAL2-8C SUC2 erg5Δ::KlLEU2-TEF1p-sDrDHCR24, erg6Δ::KlURA3-TEF1p-sDrDHCR7, NTS-DHCR24-DHCR7-TRP1 are2Δ::HIS3 | this study |
| 22 | $_{NTS}$D7/$_{NTS}$D24/#S1 | MATa ura3-52 trp1-289 leu2-3,112 his3-D1 MAL2-8C SUC2 erg5Δ:: KlLEU2 TEF1p-sDrDHCR7, ergΔ::KlURA3-TEF1p-sDrDHCR24, NTS-DHC R24-TRP1/NTS-DHCR7-HIS3 | this study |
| 23 | erg5::ccD24 | MATa ura3-52 trp1-289 leu2-3,112 his3-D1 MAL2-8C SUC2 erg5Δ::KlLEU2-TEF1p-sDrDHCR24(cc) | this study |
| 24 | erg6::ccD7 | MATa ura3-52 trp1-289 leu2-3,112 his3-D1 MAL2-8C SUC2 erg6Δ::KlURA3-TEF1p-sDrDHCR7(cc) | this study |
| 25 | erg6::ccD24 | MATa ura3-52 trp1-289 leu2-3,112 his3-D1 MAL2-8C SUC2 erg6Δ::KlLEU2-TEF1p-sDrDHCR24(cc) | this study |
| 26 | erg5::ccD7 | MATa ura3-52 trp1-289 leu2-3,112 his3-D1 MAL2-8C SUC2 erg5Δ::KlURA3-TEF1p-sDrDHCR7(cc) | this study |
| 27 | erg5::ccD24/erg6::ccD7 (#cc19) | MATa ura3-52 trp1-289 leu2-3,112 his3-D1 MAL2-8C SUC2 erg5Δ::KlLEU2-TEF1p-sDrDHCR24 (cc), erg6Δ::KlURA3-TEF1p-sDrDHCR7 (cc) | |
| 28 | erg6::ccD24/erg5::ccD7 (#ccS1) | MATa ura3-52 trp1-289 leu2-3,112 his3-D1 MAL2-8C SUC2 erg5Δ::KlLEU2-TEF1p-sDrDHCR7(cc), erg6Δ::KlURA3-TEF1p-sDrDHCR24(cc) | |
| 29 | tHMG1/#cc19 | MATa ura3-52 trp1-289 leu2-3,112 his3-D1 MAL2-8C SUC2 erg5Δ::KlLEU2-TEF1p-sDrDHCR24(cc), erg6Δ::KlURA3-TEF1p-sDrDHCR7(cc)/NTS-t HMG1-TRP1 | this study |
| 30 | tHMG1/#ccS1 | MATa ura3-52 trp1-289 leu2-3,112 his3-D1 MAL2-8C SUC2 erg5Δ::KlLEU2-TEF1p-sDrDHCR7(cc), erg6Δ::KlURA3-TEF1p-sDrDHCR24(cc)/NTS-t HMG1-TRP1 | this study |

Yeast Transformation (LiAc/PEG Method)

To perform transformation using the prepared vectors or cassettes, a strain precultured in a YPD (2% (w/v) bacto-peptone, 1% (w/v) bacto-yeast extract, and 2% (w/v) D-glucose) liquid medium was grown in a 500 mL baffled flask to an initial $OD_{600}$ of 0.2, and 50 mL of the medium was cultured in a rotary shaker at 30° C. and 180 rpm. After 6 to 7 hours, the cells were cultured until $OD_{600}$ reached 1.0, and centrifuged at 4° C. and 4,000 rpm for 10 minutes. After removing a supernatant, 1 mL of a LiAc/TE buffer solution (0.01 M Tris-HCl, 1 mM EDTA, 0.1 M LiAc, pH 7.5) was added to the pellet, and the pellet was suspended by pipetting and then centrifuged at 13,000 rpm for 1 minute, thereby obtaining a pellet. The pellet was resuspended in 500 µL of a LiAc/TE buffer solution, thereby preparing competent cells. The resulting cells were divided into five tubes at 100 µL each, and 2 µL of a recombinant vector or cassette, 10 µL of salmon sperm DNA and 600 µL of a PEG/LiAc buffer solution (50% polyethylene glycol), 0.01 M Tris-HCl, 1 mM EDTA, 0.1 M LiAc, pH 7.5) were mixed in each tube, followed by gentle pipetting 3 to 4 times. After the tube was left at 30° C. for 30 minutes, 70 µL of DMSO was added and mixed by pipetting, followed by thermal treatment at 42° C. for 15 minutes. The tube was left on ice for 3 minutes, and centrifuged at 13,000 rpm for 1 minute, thereby obtaining a pellet, and the pellet was suspended with sterilized distilled water, and plated on a specific amino acid (LEU or TRP or HIS) or base (URA)-deleted SC synthesis-based selective medium SC-LEU, SC-URA, SC-LUE-URA-TRP or SC-LUE-URA-TRP-HIS (0.67% yeast nitrogen base without amino acids, 2% glucose, 0.77 g/L drop-out amino acid mixture supplemented without leucine, tryptophan, histidine, or uracil in combination) to culture the cells at 30° C. for 48 hours, thereby obtaining a transformant (Hill J et. al. 1991).

Example 1: Preparation of Sterol-Producing Strains Through ERG5 and ERG6 Deletion and Co-Insertion of DHCR24 and DHCR7

First, for ERG5 and ERG6 deletion, two PCR fragments, such as N- and C-fragments at which homologous recombination would occur, were obtained using an erg5 dN fw, erg5 dN rv, erg5 dC fw, erg5 dC rv, erg6 dN fw, erg6 dN rv, erg6 dC fw or erg6 dC ry primer shown in Table 1, and then subjected to fusion PCR, thereby obtaining pT-ERG5dNC or pT-ERG6dNC. DNA fragments of DHCR7 and DHCR24 were recovered from pMKRQ-DrDHCR24 and pMKRQ-DrDHCR7 in which codon-optimized zebrafish-derived DHCR24 and DHCR7 genes were cloned by a codon adaptation index method for yeast through PCR, and ligated with 411 bp TEF1 promoter and 314 bp GALT terminator, which were obtained by PCR, thereby constructing vectors pT-DHCR24 and pT-DHCR7. Subsequently, TEF1p-DHCR7-GAL7t and TEF1p-DHCR24-GAL7t fragments obtained from these vectors were inserted into BamHI/XbaI sites in the N- and C-fragments of the vectors pT-ERG5dNC and pT-ERG6dNC, and K1URA3 and K1LEU2 were obtained from vectors pUG73 and pUG72 and inserted into NotI sites, thereby obtaining final vectors pT-erg5::DHCR24-LEU2, pT-erg6::DHCR7-URA3, pT-erg6::DHCR24-LEU2, and pT-erg5::DHCR7-URA3 (FIGS. 4A, 4B, 4C and 4D). The final vectors were treated with SphI/MluI to recover erg5::DHCR24-LEU2, erg6::DHCR7-URA3, erg6::DHCR24-LEU2 and erg5::DHCR7-URA3 cassettes and transformed into a CENPK strain by a LiAc/PEG method, and then transformants were selected from SC-LEU, SC-URA and SC-LEU-URA media, thereby preparing recombinant strains erg5::D24, erg6::D7, erg6::D24, erg5::D7, erg5::24/erg6::D7 and erg6::D24/erg5::D7 (FIG. 2, Step 1, and Table 3).

Example 2: Preparation of Multiple DHCR24 Integration Cassette and Selection of Recombinant Yeast For multiple integration of cholesterol biosynthetic genes, an NTS-DHCR24-86TRP1 cassette was constructed using the rDNA-NTS-based multiple integration cassette system (Moon et al., 2016) developed by the inventors. The NTS-DHCR24-86TRP1 cassette was recovered by treating pT-NTS-DHCR24-86TRP1, which was constructed by inserting TEF1p-DHCR24-GALt7 fragment derived from pT-erg6::DHCR24-LEU2 into pT-NTS-86TRP1 vector at a BamHI site (FIG. 4E), with SphI/NsiI, and then introduced into recombinant strains erg5::D24/erg6::D7 (#19, Accession No. KCTC 13889BP) and erg6::D24/erg5::D7 (#S1, Accession No. KCTC 13888BP), respectively. Transformants were selected from a SC-LEU-URA-TRP medium, thereby preparing recombinant strains NThD24/#19 or NTS D24/#S1 (FIG. 2, Step 2).

Example 3: Construction of Multiple DHCR24/DHCR7 Integration Cassette and Selection of Recombinant Yeast Vector pT-NTS-DHCR24-DHCR7-86TRP1 (FIG. 4F) having both of DCHR24 and DHCR7 expression cassettes was constructed by amplifying each of 837-bp ScACT1 promoter using ACT1p fw and ACT1p ry primers, 1458-bp DHCR7 gene using DHCR7 fw2 and DHCR7 rv2 primers, and 252-bp CYC1 terminator using CYClt fw and CYClt ry primers, making these amplified products a single fragment through fusion PCR, and inserting the fragment into the conventional vector pT-NTS-DHCR24-86TRP1 at a KpnI site. The constructed pT-NTS-DHCR24-DHCR7-86TRP1 was treated with SphI/NsiI to recover a NTS-DHCR24-DHCR7-86TRP1 cassette, transformed into recombinant strain erg5::D24/erg6::D7 (#19), and selected in a SC-LEU-URA-TRP medium, thereby manufacturing recombinant strain NTS D24D7/#19 (Accession No. KCTC 13884BP) (FIG. 2, Step 3, right panel).

In addition, vector pT-NTS-86TRP1-DHCR7 was constructed by treating vector pT-NTS-86TRP1-DHCR24-DHCR7 with BamHI to remove DHCR24. Afterward, pT-NTS-101HIS3-DHCR7 was constructed by removing 86TRP1 by treating the vector pT-NTS-86TRP1-DHCR7 with SmaI/NotI and inserting HIS3 fragment having a 101-bp promoter obtained by PCR using primers 101HIS3 fw and 101HIS3 ry (FIG. 12A). After a pT-NTS-101HIS3-DHCR7 cassette was obtained by treatment with SpeI/XbaI, the cassette was transformed into NTS D24/#S1 strain by a LiAc/PEG method and selected from a SC-HIS medium, thereby obtaining $_{NTS}D7/_{NTS}D24/\#S1$ strain (Accession No. KCTC 13885BP). To confirm the number of cassettes introduced onto the chromosome of the prepared $_{NTS}D7/_{NTS}D24/\#S1$ strain, the number of the introduced copies was analyzed through qPCR performed on the corresponding strain. It was confirmed that approximately 4 DHCR7 genes and approximately 2 DHCR24 genes were introduced into the chromosome (FIG. 12B).

Example 4: Construction of Episomal Plasmid-Based DHCR24/DHCR7 Expression Vector Vector Y2pH-DHCR7-DHCR24 using two micro yeast episomal plasmids (FIG. 4G) was constructed by inserting DHCR24-DHCR7 obtained from pT-NTS-DHCR24-DHCR7-86TRP1 into vector Y2pH at a BamHI/XhoI site, transformed into recombinant strain erg6::D24/erg5::D7 (#S1) by a LiAc/PEG method, and then selected from a SC-LEU-URA-HIS medium, thereby obtaining recombinant strain 2u D24D7/#S1 (FIG. 2, Step 3, left panel).

Example 5: Preparation of ERG27-ERG2 Fusion Gene and ERG3-Overexpressing Strain For ERG2 and ERG3 expression, vector Y2pH-ERG3-ERG2 (FIG. 4F) was constructed by amplifying each of 714-bp ScTDH3 promoter using TDH3p fw and TDH3p ry primers, 1098-bp ScERG3 gene using ERG3 fw and ERG3 ry primers, and 367-bp ScTEF1 terminator using TEF1t fw and TEF1t ry primers, making the amplified products a single fragment through fusion PCR, and amplifying each of 836-bp ScTEF2 promoter using TEF2p fw and TEF2p ry primers, 666-bp ScERG2 gene using ERG2 fw and REF2 ry primers, and 484-bp ScTDH3 terminator using TDH3t fw and TDH3t ry primers, making the amplified products a single fragment through fusion PCR, and inserting the resulting PCR fragments into a conventional Y2pH vector at a BamHI/XhoI site.

Y2pH-ERG3-ERG27-2 fusion vector (FIG. 4G) was constructed by inserting the ERG27 and ERG2, that obtained through fusion PCR using PCR product 1 using ERG27-2 fw1and ERG27-2 rv1 and PCR product 2 using ERG27-2 fw2 and ERG27-2 rv2, into Y2pH-ERG3-ERG2 vector at an SphI site instead of ERG2. The constructed Y2pH-ERG3-ERG2 and Y2pH-ERG3-ERG27-2 fusion vectors were transformed into NTS D24D7/#19 strain, and selected from a SC-LEU-URA-TRP-HIS medium, thereby preparing recombinant strains E3E2/$_{NTS}$D24D7/#19 and E3E27-2/$_{NTS}$D24D7/#19, respectively.

Example 6: Preparation of UPC2-1-Introduced Strain

YCpH-np-UPC2 constructed by the inventors using 480-bp UPC2 promoter and yeast centromere plasmids (YCp) was transformed into $_{2u}$D24D7/#19 strain, and selected from a SC-LEU-URA-TRP-HIS medium, thereby preparing recombinant strain UPC2-1/NTS D24D7/#19 (FIG. 2, Step 4, left panel).

Example 7: Preparation of erg6::D7/UPC2-1/ $_{NTS}$D24D7 Strain

Recombinant strain $_{NTS}$D24D7/WT was obtained by transforming the previously constructed NTS-DHCR24-DHCR7-86TRP1 cassette into a wild-type CEN.PK strain, and selecting the transformant from a SC-TRP medium. Afterward, the constructed Y2pH-ERG3-ERG2, Y2pH-ERG3-ERG27-2 and YCpH-np-UPC2 were introduced, thereby preparing E3E2/$_{NTS}$D24D7/WT, E3E27-2/$_{NTS}$D24D7/WT and UPC2-1/$_{NTS}$D24D7/WT strains, respectively. Among these strains, the UPC2-1/$_{NTS}$D24D7/WT strain was selected, and ERG6 gene was deleted using an erg6::DHCR7-URA3 cassette, thereby preparing erg6::D7/UPC2-1/$_{NTS}$D24D7 strain (FIG. 3).

Example 8: Preparation of Strain from which ARE2, which is the Main Gene for Sterol Esterification, is Deleted For ARE2 deletion using homologous recombination, N- and C-fragments were obtained using ARE2 dN fw, ARE2 dN fw, ARE2 dC fw, and ARE2 dC fw primers through PCR, and then subjected to fusion PCR, thereby obtaining pT-ARE2dNC. Afterward, a final vector pT-ARE2dNC-HIS was obtained by inserting ScHIS3 at an XhoI/EcoRV site between the two fragments, an ARE2dNC-HIS cassette was obtained by SphI/MluI treatment, transformed into $_{NTS}$D24D7/#19 strain by a LiAc/PEG method, and selected from a SC-LEU-URA-TRP-HIS medium, thereby preparing a recombinant strain are2Δ/$_{NTS}$D24D7/#19.

Example 9: Construction of ERG5/ERG6 Deletion and Co-Insertion of DHCR24/DHCR7 Using Codon-Optimized ccDHCR24 and ccDHCR7 by Codon Context Method and Selection of Recombinant Yeast The previously-constructed vectors pT-ERG5dNC-DrDHCR7, pT-ERG5dNC-DrDHCR24, pT-ERG6dNC-DrDHCR7 and pT-ERG6dNC-DrDHCR7 were treated with PstI/SalI to be prepared as backbones, and inserts obtained by treating ccDHCR24 and ccDHCR7 fragments obtained by PCR using primers ccD7 fw, ccD7 rv, ccD24 fw and ccD24 ry with KpnI/SalI were ligated to vectors pMKRQ-sDrDHCR7(cc) and pMKRQ-sDrDHCR24(cc) in which ccDHCR24 and ccDHCR7 genes were synthesized by a codon context method, thereby obtaining vectors pT-ERG5dNC-ccDHCR7, pT-ERG5dNC-ccDHCR24, pT-ERG6dNC-ccDHCR7 and pT-ERG6dNC-ccDHCR24. Subsequently, final vectors pT-erg5::ccDHCR24-LEU2, pT-erg6::ccDHCR7-URA3, pT-erg6::ccDHCR24-LEU2 and pT-erg5::ccDHCR7-URA3 were obtained by inserting K1URA3 and K1LEU2 derived from pUG73 and pUG72 vectors into NotI sites (FIG. 13A to 13D). The final vectors were treated with SphI/MluI to recover erg5::ccDHCR24-LEU2, erg6::ccDHCR7-URA3, erg6::ccDHCR24-LEU2 and erg5::ccDHCR7-URA3 cassettes, transformed into CEN.PK strain by a LiAc/PEG method, and selected from SC-LEU, SC-URA and SC-LEU-URA media, thereby preparing recombinant strains erg5::ccD24, erg6::ccD7, erg6::ccD24, erg5::ccD7, erg5::ccD24/erg6::ccD7 (=#cc19, Accession No. KCTC 13886BP), and erg6::ccD24/erg5::ccD7 (=#ccS1, Accession No. KCTC 13882BP) (Table 3).

Example 10: Improvement in Cholesterol Production Amount of Recombinant Strains #cc19 and #ccS1 by Multiple tHMG1 Integration Vector pT-NTS-86TRP1-tHMG1 enabling multiple integration was constructed by inserting HMG1 gene from which 552 N-terminal amino acids were deleted and amplified using primers tHMG1-fw and tHMG1-ry shown in Table 1 into an EcoRI/SalI site of pT-NTS-86TRP1 (FIG. 14A). An NTS-86TRP1-tHMG1 cassette was obtained by treating the constructed pT-NTS-86TRP1-tHMG1 vector with SpeI/NsiI, transformed into erg5::ccD24/erg6::ccD7 (=#cc19) and erg6::ccD24/erg5::ccD7 (=#ccS1) strains by a LiAc/PEG method, and selected from a SC-TRP medium, thereby constructing recombinant strains tHMG1/erg5::ccD24/erg6::ccD7 (=tHMG1/#cc19, Accession No. KCTC 13887BP) and tHMG1/erg6::ccD24/erg5::ccD7 (=tHMG1/#ccS1, Accession No. KCTC 13883BP) (Table 3). To confirm the number of cassettes introduced onto the chromosomes of the constructed strains tHMG1/#cc19 and tHMG1/#ccS1, the corresponding strains were analyzed to determine the number of introduced copies through qPCR, confirming that approximately 3 to 4 cassettes were introduced (FIG. 14B).

EXPERIMENTAL EXAMPLES

Analysis of Insert Copy Number Using qPCR

To confirm the copy number of target gene expression cassettes inserted into the prepared recombinant strain, chromosomal DNA was recovered and used as a template to perform qPCR.

Analysis of Metabolic By-Products and Residual Carbon Sources

After final culture, the residual amounts of metabolic by-products (e.g., ethanol or acetate) accumulated in a supernatant and glucose, which is a carbon source added in culture, were measured. A sample used in analysis was the final culture solution of the main culture, which was centrifuged (12,000 rpm, 10 min), followed by analyzing a supernatant. The analysis was performed using a kit (Roche/COWIE) for ethanol, acetate or glucose measurement of a bio process analyzer.

HPLC-UV/Vis-Based Analysis for Cholesterol and Precursor Thereof

For a HPLC assay, a Synthetic Complete medium [SC medium (0.67% yeast nitrogen base without amino acids, 2% glucose, 0.77 g/L drop-out amino acid mixture supplemented with all required amino acids)] was inoculated with 1 or 2 colonies of the strain to perform seed culture, and then the cells were grown in a SC or YPD medium to reach OD600 of 0.3 to 0.5 after initial inoculation. To extract total sterols, 10 mL of the sample obtained after 3- to 6-day culture (28° C., 220 rpm) was recovered, and then a 0.05 g/wet weight of pellet was suspended in 1 mL KOH/EtOH (3:2) (KOH final concentration: 4.5 M) mixed solution, cultured at 85° C. for 1 hour, and mixed with 0.5 mL heptane (Sigma) using a bead beater (6,000 rpm, 15 sec, repeat three times). The mixed sample was centrifuged (12,000 rpm, 10 min, 25° C.) to recover 0.5 mL of a heptane layer from a supernatant (12,000 rpm, 10 min, 25° C.) and dried, and then HPCL analysis was performed on a sample dissolved by adding 200 μL of acetone. To extract free sterols, 0.5 mL of a chloroform:MeOH (2:1) mixture was added to a pellet, and mixed using a bead beater (6,000 rpm, 15 sec, repeat three times). The mixed sample was centrifuged (12,000 rpm, 10 min, 25° C.), an organic solvent layer was recovered and dried, 250 μL hexane was added to the dry pellet to dissolve, followed by drying again. After complete drying, a HPLC assay was performed on the sample dissolved by adding 200 μL acetone. In the HPLC assay, a column was Cosmosil C18-PAQ (4.6 mm*250 mm), a flow rate was 1 mL/min, an analysis solvent was 90% acetonitrile, and an analysis time was 50 min. Peaks corresponding to cholesterol and precursors thereof were analyzed at 203 nm using a UV/Vis detector.

Analysis of Productivity of HPLC-CAD-Based Cholesterol and Precursor Thereof

Cell culture for HPLC-CAD analysis to confirm the productivity of cholesterol and precursors thereof in the prepared strain was the same as described above in the HPLC-based analysis. For extraction of cholesterol and precursors thereof, 50 mL of a sample cultured for 3 to 6 days (28° C., 220 rpm) and resuspended in 20 mL of a resuspension solution (15% KOH (w/v), 0.125% pyrogallol (w/v), 71% MeOH (v/v)). The resulting product was reacted at 85° C. for 2 hours, cooled at room temperature, and mixed with 5 mL of petroleum ether by vortexing for 5 minutes. The mixed sample was centrifuged (3,000 g, 5 min), and a supernatant was recovered. The extraction process by adding petroleum ether was repeated twice, and by using 3 mL of petroleum ether, all of a supernatant was recovered. The recovered supernatant was dried using a rotational vacuum concentrator, and then HPLC-CAD analysis was performed on a sample dissolved by adding 1 mL of methanol to the dry sample. In HPLC-CAD analysis, a column was Capcellpak (C18, 4.6 mm×250 mm, 5 μm), a mobile phase was methanol, and a flow rate and conditions are as shown in Table below. Analysis time was 45 min.

| Time (min) | Flow (mL/min) | % A (50% methanol) | % B (100% methanol) |
|---|---|---|---|
| 0.0 | 0.5 | 10 | 90 |
| 10.0 | 0.5 | 0 | 100 |
| 40.0 | 0.5 | 0 | 100 |
| 40.1 | 0.5 | 10 | 90 |
| 45.0 | 0.5 | 10 | 90 |

As a result of analyzing 7 types of reference standards (zymosterol, ergosterol, lathosterol, 7-dehydrocholesterol, 7-dehydrodesmosterol, desmosterol and cholesterol) by the analysis method described above (see FIG. 9), the HPLC peak retention time of ergosterol and desmosterol overlapped with 30.7 min and 30.4 min, respectively, but only ergosterol was produced in a wild-type yeast strain, and in a recombinant yeast strain prepared to produce cholesterol and precursors thereof, only desmosterol was produced. Therefore, final productivity analysis was performed through a corresponding analysis method.

Figure 5:
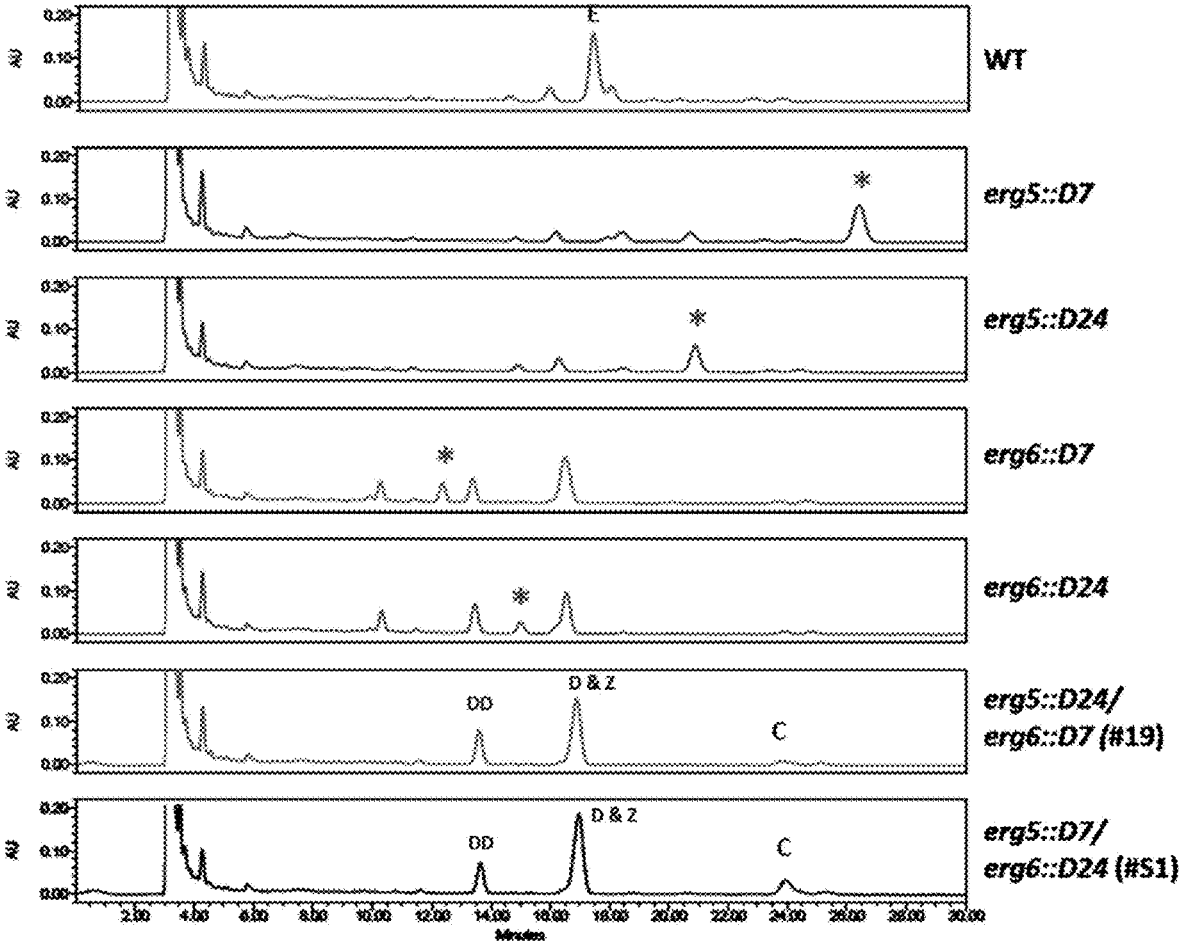
FIG. 5 shows the result of analyzing the production amounts of cholesterol and precursors thereof of recombinant yeast strains #19 (erg5::D24/erg6::D7) and #S1 (erg6::D24/erg5::D7) according to one embodiment of the present invention using HPLC-UV/Vis chromatograms (*: unknown peak, DD: dehydrodesmosterol), D: desmosterol, Z: zymosterol, C: cholesterol).

Experimental Example 1: HPLC Assay on Sterol-Producing Strain Prepared by erg5, erg6 Deletion and DHCR24, DHCR7 Expression As a result of HPLC-UV/Vis analysis, a cholesterol peak was able to be found in the erg5::D24/erg6::D7 or, erg6::D24/erg5::D7 strain, the cholesterol productivity of the erg5::D24/erg6::D7 (#19) strain was 3.1 ppm, and the cholesterol production amount of the erg6::D24/erg5::D7 (#S1) strain was 7.5 ppm (Table 4). However, the content of a cholesterol precursor, such as zymosterol, dehydrodesmosterol or desmosterol was very high (FIG. 5).

Figure 6:
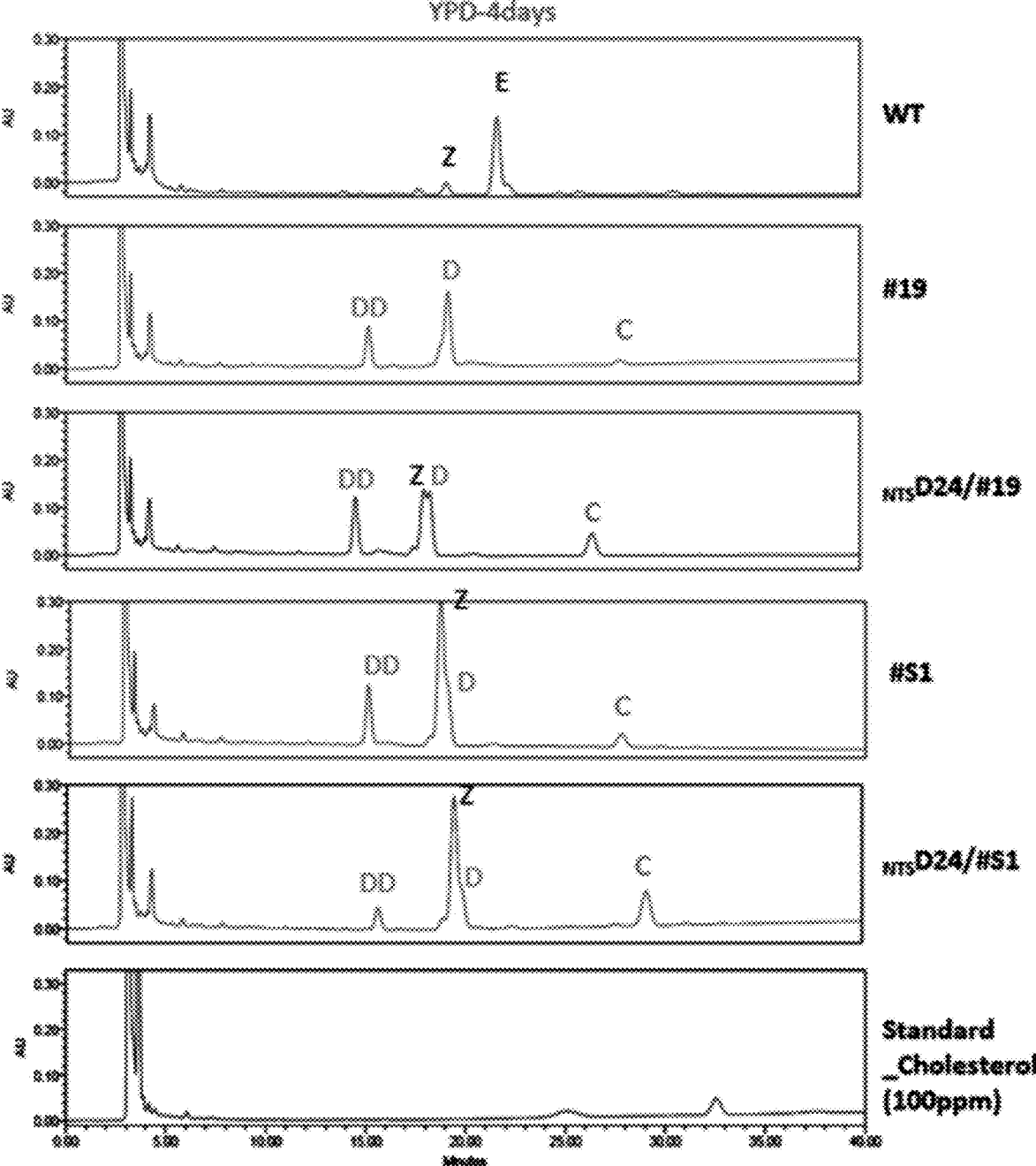
FIG. 6 shows the result of analyzing the production amounts of cholesterol and precursors thereof of recombinant yeast strains $_{NTS}$D24/#19 (NTS D24/erg5::D24/erg6::D7) and $_{NTS}$D24/#S1 ($_{NTS}$D24/erg6::D24/erg5::D7) according to one embodiment of the present invention using HPLC-UV/Vis chromatograms (DD: dehydrodesmosterol, D: desmosterol, Z: zymosterol, C: cholesterol).

Experimental Example 2: HLPC Assay on Sterol-Producing Strain Prepared by Multiple DHCR24 Integration As a result of the HPLC assay on a strain into which an NTS-DHCR24-86TRP1 cassette was additionally introduced using a rDNA-NTS-based multiple integration cassette system developed by the inventors to increase the production amount of cholesterol (a $_{NTS}$D24/#19 recombinant strain), a peak of 7.4 ppm cholesterol production was found, which is approximately 2.4-fold higher than a #19 strain (FIG. 6, Table 4). In addition, in a $_{NTS}$D24/#S1 recombinant strain, a peak of 11.5 ppm cholesterol production was found, which is approximately 1.5-fold higher than a #S1 strain (FIG. 6, Table 4).

23

Figure 7A:
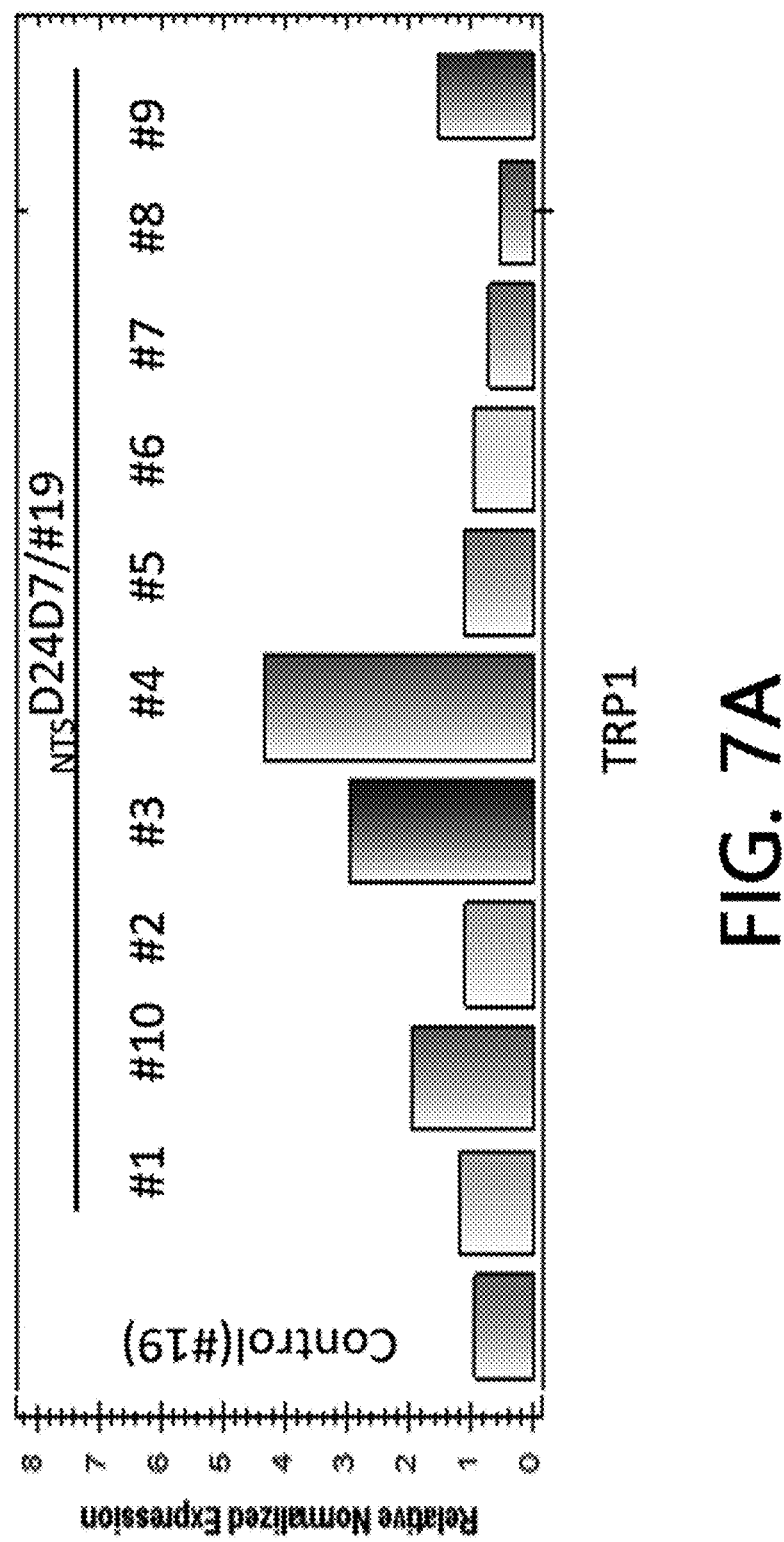
FIGS. 7A to 7C shows the results of comparative analysis of characteristics of recombinant yeast strains according to one embodiment of the present invention.
Figure 7B:
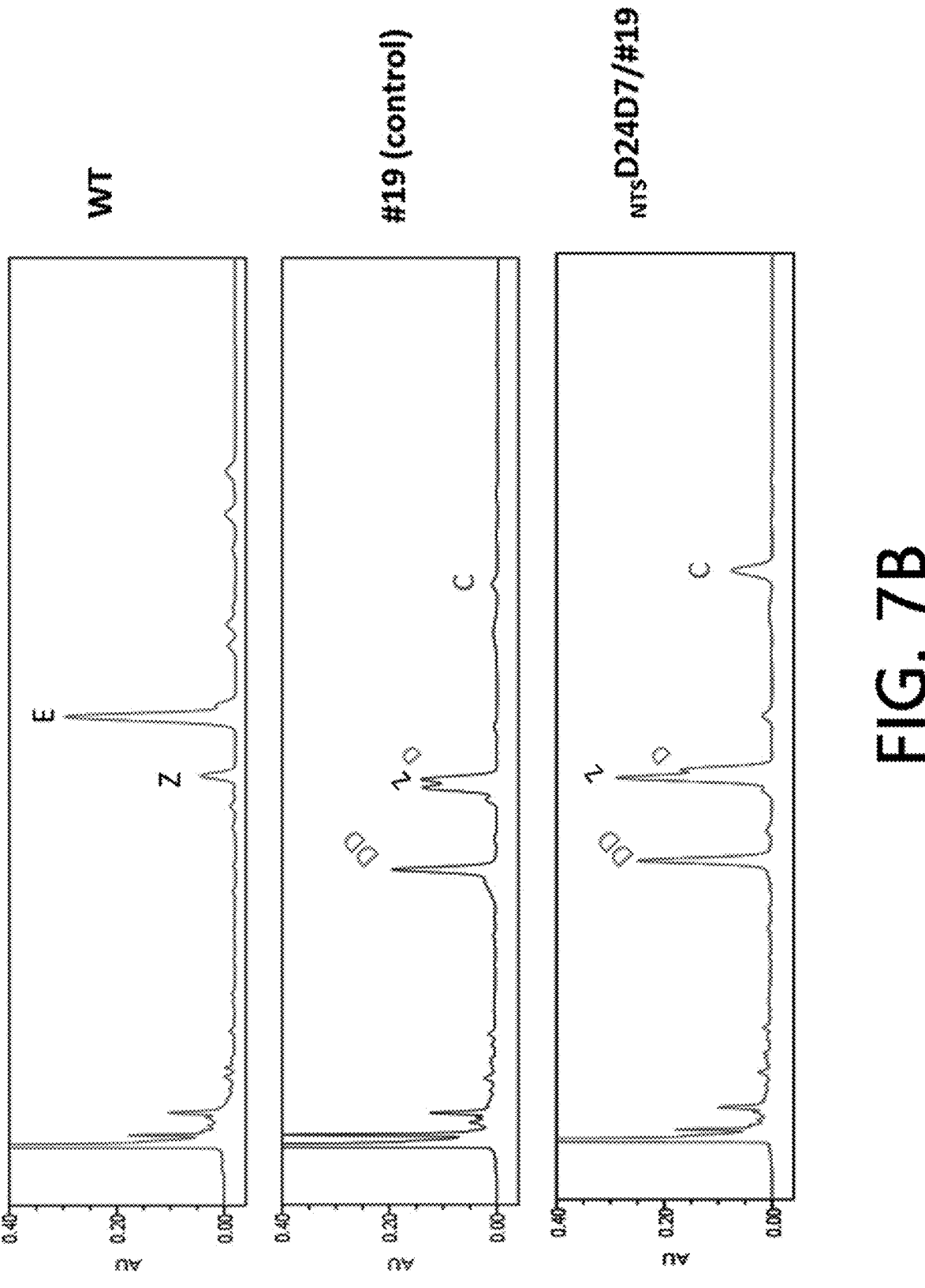

Experimental Example 3: qPCR and HPLC Assay
for Recombinant Strain Prepared by DHCR24,
DHCR7 Multiple Integration As a qPCR result of analyzing the number of cassettes in a $_{NTS}$D24D7/#19 recombinant strain obtained by multiple integration of an NTS-DHCR24-DHCR7-86TRP1 cassette having both cassettes expressing DHCR24 and DHCR7 genes, it was confirmed that strains having 3 or 4 cassettes were able to be obtained (FIG. 7A). As a result of HPLC analysis, in the $_{NTS}$D24D7/erg5::D24/erg6::D7 ($_{NTS}$D24D7/#19) recombinant strain, a peak of 9.0 ppm cholesterol production was able to be found, which is approximately 2.9-fold higher than an erg5::D24/erg6::D7(#19) strain (FIG. 7B). In addition, as a result of a HPLC assay, in a $_{2\mu}$D24D7/#S1 recombinant strain, a peak of 11.1 ppm cholesterol production was also able to be found, which is

24

Figure 8:
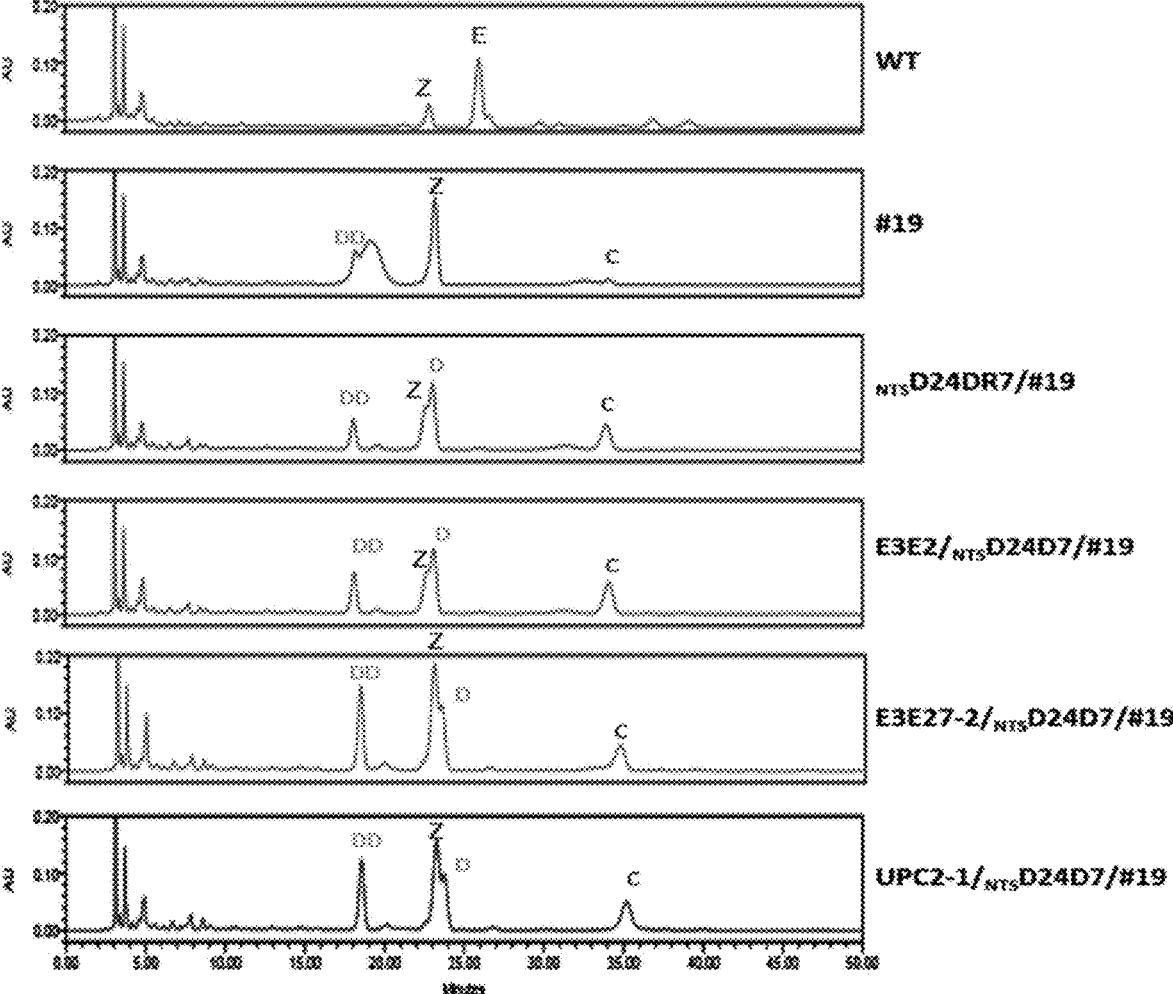
FIG. 8 shows the result of analyzing the production amounts of cholesterol and precursors thereof of recombinant yeast strains E3E2/$_{NTS}$D24D7/#19, E3E27-2/$_{NTS}$D24D7/#19 and UPC2-1/$_{NTS}$D24D7/#19 according to one embodiment of the present invention using HPLC-UV/Vis chromatograms (DD: dehydrodesmosterol, D: desmosterol, Z: zymosterol, C: cholesterol).

19, and UPC2-1/$_{NTS}$D24D7/#19 recombinant strains (Table 4, FIG. 8). However, ERG3, ERG27-2 or UPC2-1-introduced recombinant strains showed significantly increased cholesterol precursor productivity.

Experimental Example 5: Analysis of Production
Amounts of Cholesterol and Precursor Thereof in
HPLC-CAD-Based Recombinant Strains The productivity of cholesterol and precursors thereof was analyzed by a HPLC-CAD-based analysis method, and a result thereof is shown in FIG. 9. Compared to a wild-type strain, it was confirmed that the recombinant strain #19 (erg5::D24/erg6::D7) produced 7-dehydrodesmosterol, zymosterol, desmosterol, 7-dehydrocholesterol and cholesterol in high yields.

The production amounts of cholesterol and precursors thereof in the recombinant strain prepared by the method described above are summarized in Table 4.

TABLE 4

Figure 7C:
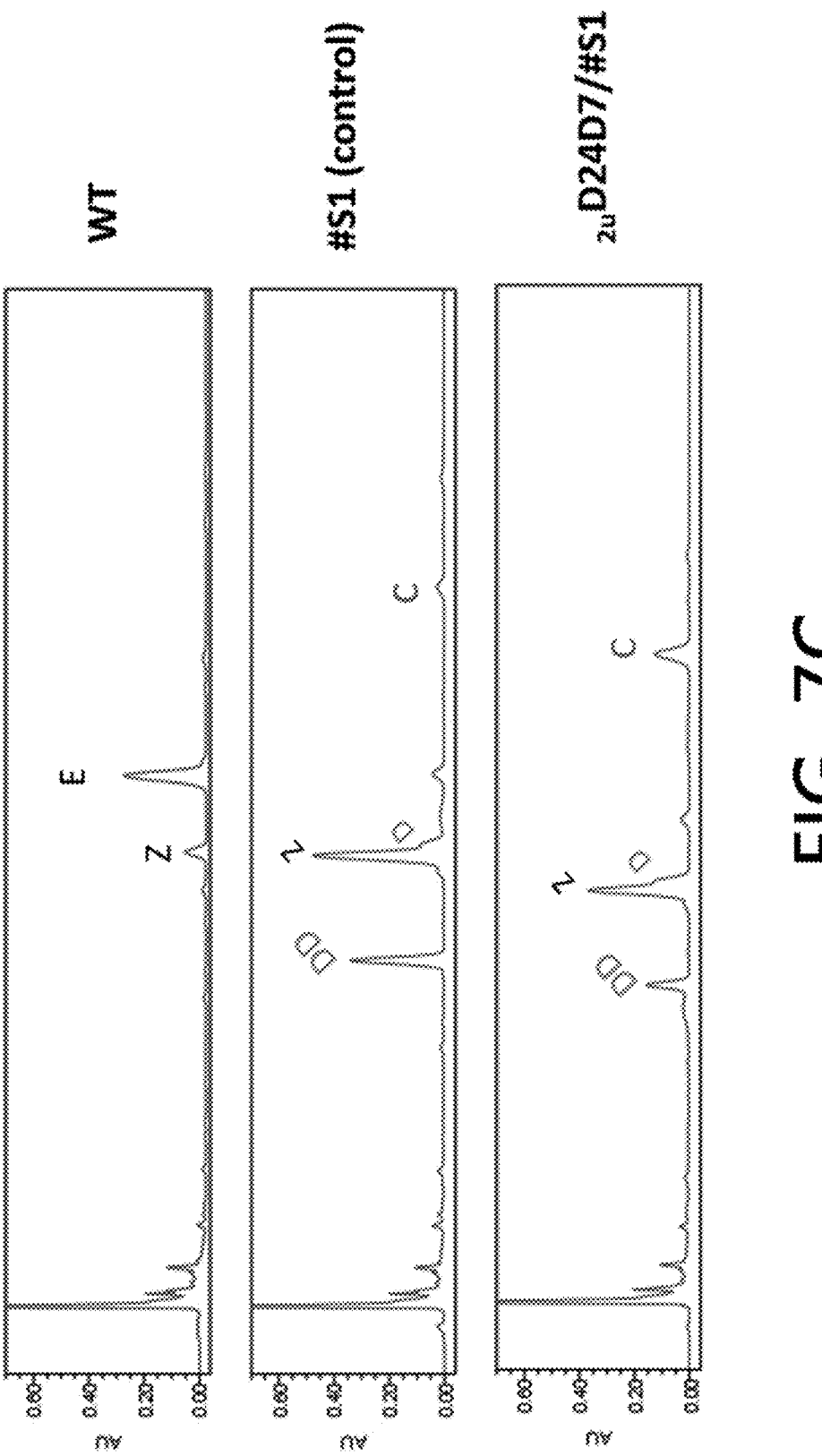

| HPLC-CAD-based comparative analysis of production amounts of cholesterol and precursor thereof in recombinant strains | | | | | | | | | | |
|---|---|---|---|---|---|---|---|---|---|---|
| | introduced | culture | Concentration (ppm) | | | | | | | |
| Strains | gene (copy #) | medium | E | Z | L | 7-dc | 7-dm | D | C | OD$_{600\ nm}$ |
| CEN.PK(WT) | — | SC | 5.5 | 6.7 | 2.2 | 0 | 0 | 0 | 0 | 12.7 |
| #19 (erg5::D24/erg6::D7) | DHCR7(1), DHCR24(1) | | 0 | 10.5 | 0 | 1.9 | 23.4 | 4.5 | 3.1 | 8.3 |
| #S1 (erg6::D24/erg5::D7) | | | 0 | 25.0 | 0 | 3.4 | 19.8 | 5.2 | 7.5 | 16.8 |
| $_{NTS}$D7/#19 | DHCR7(5), DHCR24(1) | | 0 | 7.3 | 0 | 0.5 | 17.6 | 10.6 | 3.8 | 7.9 |
| $_{NTS}$D7/#S1 | DHCR7(4), DHCR24(1) | | 0 | 21.9 | 0 | 1.9 | 19.9 | 15.0 | 9.0 | 20.7 |
| $_{NTS}$D24/#19 | DHCR7(1), DHCR24(4) | | 0 | 16.4 | 0 | 4.3 | 15.0 | 2.6 | 7.4 | 9.1 |
| $_{NTS}$D24/#S1 | DHCR7(1), DHCR24(4) | | 0 | 22.2 | 0 | 2.5 | 13.2 | 6.3 | 11.5 | 19.1 |
| $_{NTS}$D24D7/#19 | DHCR7(4), DHCR24(4) | | 0 | 14.1 | 0 | 1.9 | 16.4 | 6.3 | 9.0 | 9.3 |
| $_{2\mu}$D24D7/#S1 | DHCR7(~10), DHCR24(~10) | | 0 | 17.8 | 0 | 2.1 | 11.2 | 5.8 | 11.1 | 9.5 |
| E3E2/$_{NTS}$D24D7/#19 | DHCR7(4), DHCR24(4), ERG3(~10), ERG2(~10) | | 0 | 8.4 | 0 | 1.9 | 17.0 | 7.0 | 11.5 | 7.2 |
| E3E27-2/$_{NTS}$D24D7/#19 | DHCR7(4), DHCR24(4), ERG3(~10), ERG27-ERG2 fusion(~10) | | 0 | 17.0 | 0 | 2.6 | 28.1 | 6.2 | 9.0 | 6.2 |
| UPC2-1/$_{NTS}$D24D7/#19 | DHCR7(4), DHCR24(4), UPC2-1(1~2) | | 0 | 12.2 | 0 | 2.0 | 17.2 | 5.3 | 7.9 | 7.2 | approximately 1.5-fold higher than the #S1 strain (FIG. 7C, Table 4).

Experimental Example 4: HPLC Assay for
Recombinant Strain Prepared through
ERG27-ERG2 Fusion Gene, ERG3 and UPC2-1
Overexpression As a result of a HPLC assay for strains further expressing ERG27, ERG2 and ERG3 genes involved in cholesterol production from zymosterol to further increase cholesterol production efficiency of the prepared $_{NTS}$D24D7/#19 recombinant strain, compared to the $_{NTS}$D24D7/#19, it was confirmed that the difference in cholesterol production amount was not large in E3E2/$_{NTS}$D24D7/#19, E3E27-2/$_{NTS}$D24D7/

(E: Ergosterol, Z: Zymosterol, 7-dc: 7-dehydrocholesterol, 7-dm: 7-dehydrodesmosterol, D: Desmosterol, C: Cholesterol)

(Strains: CEN.PK (WT), #19, #S1, $_{NTS}$D7/#19, $_{NTS}$D7/#S1, $_{NTS}$D24/#19, $_{NTS}$D24/#S1, $_{NTS}$D24D7/#19, $_{2\mu}$D24D7/#S1, E3E2/$_{NTS}$D24D7/#19, E3E27-2/$_{NTS}$D24D7/#19, UPC2-1/$_{NTS}$D24D7/#19)

Experimental Example 6: HPLC-UV/Vis Assay for
Recombinant Strain from which ARE2, which is a
Main Gene for Sterol Esterification, was Deleted Among ARE1 and ARE2 genes (Hohmann H-P et. al. 2017) involved in esterification and lipid droplet storage to store surplus intracellular sterols in yeast cells, it was tried to delete ARE2, which plays a major role in aerobic growth, in the $_{NTS}$D24D7/#19 strain using a gene disruption technique by homologous recombination (FIG. 10A). In the case of a sample prepared by an extraction method in which a free cholesterol form was maintained, it was observed that there was not significant change in cholesterol amount in the wild-type strain background, but a dehydrodesmosterol amount among the precursors was greatly reduced (FIG. 10B). This shows that, in the case of dehydrodesmosterol, it is mostly present in an esterified form, but cholesterol is mostly present in a free form. As a result of a HPLC assay for the prepared are2Δ/NTS D24D7/#19 strain, there was no significant difference in cholesterol amount, and the amount of dehydrodesmosterol which was accumulated in a large quantity was slightly reduced. These results suggest that the most of the cholesterol produced in the $_{NTS}$D24D7/#19 strain is in a free sterol form.

Experimental Example 7: Analysis of Sterol-Producing Recombinant Yeast *S. Cerevisiae* for Wild-Type Strain Among the previously attempted strategies, in a strategy in which a wild-type strain was first subjected to the multiple integration of NTS-DHCR24-DHCR7-86TRP1 cassettes and then ERG6 deletion as a method of increasing the number of inserted NTS-DHCR24-DHCR7-86TRP1 cassettes on the chromosome using a multiple integration cassette system, as a first step, the number of inserted cassettes in the prepared $_{NTS}$D24D7/WT recombinant strain was analyzed by qPCR, thereby obtaining several candidate strains in which 4 to 10 cassettes were inserted (FIG. 11A). Afterward, in a HPLC-UV/Vis assay, an ergosterol peak was greatly reduced in a candidate group ($_{NTS}$D24D7/WT #8) in which 7 cassettes were inserted, but the peak estimated as campesterol showed the highest value (FIG. 11B). Accordingly, in a subsequent experiment, E3E2/$_{NTS}$D24D7/WT and E3E27-2/$_{NTS}$D24D7/WT strains were prepared using the 7 cassette-inserted candidate group ($_{NTS}$D24D7/WT #8), and as a result of HPLC-UV/Vis assay, there was no significant difference from the $_{NTS}$D24D7/WT strain. Meanwhile, in the case of a UPC2-1/NTS D24D7/WT recombinant strain, due to overall activation of an ergosterol biosynthesis pathway, rather, ergosterol production increased (FIG. 11C). Subsequently, as a result of a HPLC-UV/Vis assay for the prepared erg6::D7/UPC2-1/$_{NTS}$D24D7 strain, a cholesterol production amount was not better, compared to the $_{NTS}$D24D7/erg5::D24/erg6::D7 ($_{NTS}$D24D7/#19) recombinant strain, which showed the highest cholesterol production amount (FIG. 11D).

Experimental Example 8: Analysis of Amounts of Growth and by-Product Accumulation of Sterol-Producing Recombinant Strains #S1 and #19

As a result of confirming the amount of metabolic by-product accumulation of the prepared strain, by-products such as ethanol and acetate were accumulated after the final culture in the #19 (erg5::D24/erg6::D7) strain, whereas there were a small quantity of acetate accumulation but no accumulation of a major metabolic by-product, ethanol, in the #S1 (erg6::D24/erg5::D7) strain, and therefore, the same pattern as the wild type was able to be confirmed. In addition, as a result of analysis of a cell growth amount, since the OD600 of the #19 (erg5::D24/erg6::D7) strain was approximately 14.8, it was confirmed that growth was inhibited compared to the OD600 of each of the wild-type strain (WT) and the #S1 (erg6::D24/erg5::D7) strain, which were approximately 46.5 and 57.3 (Table 5).

TABLE 5

Comparative analysis of amounts of growth and by-product accumulation in recombinant strains #S1 and #19

| Strains | culture medium | By-product & Residual C-source(mg/L) | | | Cell growth |
| | | Acetate | Ethanol | Glucose | OD$_{600\,nm}$ |
| --- | --- | --- | --- | --- | --- |
| CEN.PK(WT) | YPD | 0 | 0 | 0 | 46.5 |
| #19 (erg5::D24/erg6::D7) | | 385 | 7501 | 0 | 14.8 |
| #S1 (erg6::D24/erg5::D7) | | 8 | 0 | 0 | 57.3 |

Experimental Example 9: Analysis of Production Amounts of Cholesterol and Precursor Thereof in #S1-Derived Strain and DHCR Gene Codon-Optimized Strains in SC or YPD Medium As a result of the analysis of a cell production amount and a by-product accumulation amount, it is suggested that, compared to the #19 (erg5::D24/erg6::D7) strain, the #S1 (erg6::D24/erg5::D7) strain with high growth and less by-product accumulation is more suitable as an industrial strain. Accordingly, the cholesterol and precursor production amounts of the #S1-derived recombinant strains cultured in a SC or YPD medium were measured, and detailed comparative analysis was performed using a HPLC-CAD-based LC chromatogram (Table 6). In the culture in the YPD medium, compared to the culture in the SC medium, cell growth was high and a total cholesterol production amount was large. On the other hand, in the culture in the SC medium, it was able to be confirmed that the cholesterol production amount per cell was high.

TABLE 6

Analysis of production amount of cholesterol and precursor thereof in #S1 (erg6::D24/erg5::D7)-derived recombinant strains in SC or YPD medium using HPLC-CAD-based HPLC chromatogram

| Strains | culture medium | E | Z | L | 7-dc | 7-dm | D | C | $OD_{600\ nm}$ |
|---|---|---|---|---|---|---|---|---|---|
| CEN.PK(WT) | SC | 5.1 | 10.2 | 1.8 | 1.8 | 0.0 | 0.0 | 0.0 | 17.0 |
| #S1(erg6::D24/erg5::D7) | | 0 | 25.0 | 0 | 3.4 | 19.8 | 5.2 | 7.5 | 16.8 |
| $_{NTS}$D7/#S1 | | 0 | 21.9 | 0 | 1.9 | 19.9 | 15.0 | 9.0 | 20.7 |
| $_{NTS}$D24/#S1 | | 0 | 22.2 | 0 | 2.5 | 13.2 | 6.3 | 11.5 | 19.1 |
| $_{2\mu}$D24D7/#S1 | | 0 | 17.8 | 0 | 2.1 | 11.2 | 5.8 | 11.1 | 9.5 |
| CEN.PK(WT) | VPD | 5.8 | 11.6 | 2.8 | 4.2 | 1.7 | 0 | 0 | 42.2 |
| #S1(erg6::D24/erg5::D7) | | 0 | 30.7 | 1.6 | 1.5 | 19.7 | 13.3 | 9.4 | 59.0 |
| $_{NTS}$D7/#S1 | | 0 | 26.7 | 1.2 | 0.8 | 19.5 | 22.4 | 9.0 | 62.1 |
| $_{NTS}$D24/#S1 | | 0 | 33.0 | 2.5 | 3.4 | 15.0 | 8.4 | 15.0 | 64.5 |
| $_{2\mu}$D24D7/#S1 | | 0 | 29.3 | 0 | 2.5 | 22.3 | 15.3 | 12.9 | 18.7 |

(E: Ergosterol, Z: Zymosterol, 7-dc: 7-dehydrocholesterol, 7-dm: 7-dehydrodesmosterol, D: Desmosterol, C: Cholesterol)

(Strains: CEN.PK (WT), #S1, $_{NTS}$D7/#S1, $_{NTS}$D24/#S1, $_{2\mu}$D24D7/#S1)

In addition, as a result of a HPLC assay for the $_{NTS}$D7/$_{NTS}$D24/#S1 recombinant strain, it was able to be confirmed that a 9.3 ppm cholesterol production peak was found, which is approximately 1.7-fold higher than the #S1 strain (FIG. 12C, Table 7). In addition, as a result of a HPLC assay for erg5::ccD24/erg6::ccD7(=#cc19) and erg6::ccD24/erg5::ccD7(=#ccS1), it was confirmed that 30.1 and 29.4 ppm of cholesterol and 6.1 and 6.0 ppm of zymosterol were produced, which shows that the cholesterol production amounts are approximately 5-fold or more increased, compared to the #S1 strain (FIG. 13E, Table 7).

TABLE 7

Analysis of production amounts of cholesterol and precursor thereof in recombinant strains using HPLC-CAD-based HPLC chromatogram

| Strains | Culture condition | E | Z | L | 7-dc | 7-dm | D | C |
|---|---|---|---|---|---|---|---|---|
| CEN.PK | YPD, | 21.4 | 7.0 | 2.0 | 0 | 0 | 0 | 0 |
| #19 | 5 days | 0 | 3.5 | 0 | 0 | 3.3 | 5.3 | 2.4 |
| #S1 | | 0 | 0 | 0.5 | 0.9 | 6.2 | 5.9 | 5.2 |
| D7/D24/S1 | | 0 | 27.2 | 0 | 0 | 1.9 | 11.4 | 9.3 |
| #cc19 | | 0 | 6.1 | 0 | 0 | 0 | 0 | 30.1 |
| #ccS1 | | 0 | 6.0 | 0 | 0 | 0 | 0 | 29.4 |

(7-dm: 7-dehydrodesmosterol, 7-dc: 7-dehydrocholesterol, Z: Zymosterol, D: Desmosterol, E: Ergosterol, L: Lathosterol, C: Cholesterol, D7/D24/S1: $_{NTS}$D7/NTS D24/#S1)

In addition, the result of the HPLC assay, compared to #cc19 and #ccS1 strains, tHMG1/#cc19, tHMG1/#ccS1 strains showed a pattern in which all of squalene, oxidosqualene, lanosterol and zymosterol are accumulated, and approximately 1.3 to 1.5-fold higher cholesterol production amounts when comparing HPLC chromatogram peak areas (FIG. 14C).

The invention claimed is:

1. A recombinant yeast strain having sterol productivity, into which ERG5 and ERG6 genes are deleted and codon-optimized DHCR24 and DHCR7 synthetic genes are introduced, wherein the codon-optimized DHCR24 synthetic gene consists of SEQ ID NO: 17 and is introduced into an ERG6 gene site and the codon-optimized DHCR7 synthetic gene consists of SEQ ID NO: 18 and is introduced into an ERG5 gene site; or the codon-optimized DHCR24 synthetic gene consists of SEQ ID NO: 17 and is introduced into an ERG5 gene site and the codon-optimized DHCR7 synthetic gene consists of SEQ ID NO: 18 and is introduced into an ERG6 gene site, wherein the sterol comprises one or more of a cholesterol precursor or cholesterol, and wherein the cholesterol precursor comprises one or more
selected from the group consisting of squalene, oxi-
dosqualene, zymosterol, and lathosterol.

2. The recombinant yeast strain of claim 1, wherein a
tHMGJ gene is further introduced onto a host chromosome.

* * * * *

SEQUENCE LISTING

```
<160> NUMBER OF SEQ ID NOS: 69

<210> SEQ ID NO 1
<211> LENGTH: 47
<212> TYPE: DNA
<213> ORGANISM: Saccharomyces cerevisiae

<400> SEQUENCE: 1
cacaagaggt aggtcgaaac agaacatgaa agttggtcgg taggtgc          47

<210> SEQ ID NO 2
<211> LENGTH: 49
<212> TYPE: DNA
<213> ORGANISM: Saccharomyces cerevisiae

<400> SEQUENCE: 2
ggttttgcac catatcttca taacctgtca ccttgaaact acctctggc         49

<210> SEQ ID NO 3
<211> LENGTH: 16
<212> TYPE: DNA
<213> ORGANISM: Saccharomyces cerevisiae
```

-continued

```
<400> SEQUENCE: 3
gaaacgaaga taaatc                                                    16

<210> SEQ ID NO 4
<211> LENGTH: 21
<212> TYPE: DNA
<213> ORGANISM: Saccharomyces cerevisiae

<400> SEQUENCE: 4 ttaccttttta catttcagca a                                             21

<210> SEQ ID NO 5
<211> LENGTH: 50
<212> TYPE: DNA
<213> ORGANISM: Saccharomyces cerevisiae

<400> SEQUENCE: 5
cttcgaagaa tatactaaaa aatgagcagg caagataaac gaaggcaaag              50

<210> SEQ ID NO 6
<211> LENGTH: 50
<212> TYPE: DNA
<213> ORGANISM: Saccharomyces cerevisiae

<400> SEQUENCE: 6
tattgagcac gtgagtatac gtgattaagc acacaaaggc agcttggagt              50

<210> SEQ ID NO 7
<211> LENGTH: 1617
<212> TYPE: DNA
<213> ORGANISM: Saccharomyces cerevisiae

<400> SEQUENCE: 7
atgagttctg tcgcagaaaa tataatacaa catgccactc ataattctac gctacaccaa    60
ttggctaaag accagccctc tgtaggcgtc actactgcct tcagtatcct ggatacactt   120
aagtctatgt catatttgaa aatatttgct actttaatct gtattctttt ggtttgggac   180
caagttgcat atcaaatcaa gaaaggttcc atcgcaggtc caaagtttaa gttctggccc   240
atcatcggtc cattttttgga atccttagat ccaaagtttg aagaatataa ggctaagtgg   300
gcatccggtc cactttcatg tgtttctatt ttccataaat ttgttgttat cgcatctact   360
agagacttgg caagaaagat cttgcaatct tccaaattcg tcaaaccttg cgttgtcgat   420
gttgctgtga agatcttaag accttgcaat tgggtttttt tggacggtaa agctcatact   480
gattacagaa aatcattaaa cggtcttttc actaaacaag ctttggctca atacttacct   540
tcattggaac aaatcatgga taagtacatg gataagtttg ttcgtttatc taaggagaat   600
aactacgagc cccaggtctt tttccatgaa atgagagaaa ttctttgcgc cttatcattg   660
aactctttct gtggtaacta tattaccgaa gatcaagtca gaaagattgc tgatgattac   720
tatttggtta cagcagcatt ggaattagtc aacttcccaa ttattatccc ttacactaaa   780
acatggtatg gtaagaaaac tgcagacatg gccatgaaga ttttcgaaaa ctgtgctcaa   840
atggctaagg atcatattgc tgcaggtggt aagccagttt gtgttatgga tgcttggtgt   900
aagttgatgc acgatgcaaa gaatagtaac gatgatgatt ctagaatcta ccacagagag   960
tttactaaca aggaaatctc cgaagctgtt ttcactttct tatttgcttc tcaagatgcc  1020
tcttcttctt tagcttgttg gttgttccaa attgttgctg accgtccaga tgtcttagct  1080
```

-continued

```
aagatcagag aagaacaatt ggctgttcgt aacaatgaca tgtctaccga attgaacttg      1140
gatttgattg agaaaatgaa gtacaccaat atggtcataa aagaaacttt gcgttacaga      1200
cctcctgtct tgatggttcc atatgttgtt aagaagaatt tcccagtttc ccctaactat      1260
accgcaccaa agggcgctat gttaattcca accttatacc cagctttaca tgatcctgaa      1320
gtttacgaaa atcctgatga gttcatccct gaaagatggg tagaaggctc taaggctagt      1380
gaagcaaaga agaattggtt ggttttggt tgtggtccac acgtttgctt aggtcaaaca      1440
tatgtcatga ttaccttcgc cgctttgttg ggtaaatttg cactatatac tgatttccat      1500
catacagtga ctccattaag tgaaaaaatc aaggttttcg ctacaatttt cccaaaagat      1560
gatttgttac tgactttcaa aaagagagac ccaattactg gagaagtctt cgaataa        1617
```

```
<210> SEQ ID NO 8
<211> LENGTH: 1152
<212> TYPE: DNA
<213> ORGANISM: Saccharomyces cerevisiae

<400> SEQUENCE: 8
atgagtgaaa cagaattgag aaaaagacag gcccaattca ctagggagtt acatggtgat       60
gatattggta aaaagacagg tttgagtgca ttgatgtcga agaacaactc tgcccaaaag      120
gaagccgttc agaagtactt gagaaattgg gatggtagaa ccgataaaga tgccgaagaa      180
cgtcgtcttg aggattataa tgaagccaca cattcctact ataacgtcgt tacagatttc      240
tatgaatatg gttggggttc ctctttccat ttcagcagat tttataaagg tgagagtttc      300
gctgcctcga tagcaagaca tgaacattat ttagcttaca aggctggtat tcaaagaggc      360
gatttagttc tcgacgttgg ttgtggtgtt ggggccccag caagagagat tgcaagattt      420
accggttgta acgtcatcgg tctaaacaat aacgattacc aaattgccaa ggcaaaatat      480
tacgctaaaa aatacaattt gagtgaccaa atggactttg taaagggtga tttcatgaaa      540
atggatttcg aagaaacac tttcgacaaa gtttatgcaa ttgaggccac atgtcacgct      600
ccaaaattag aaggtgtata cagcgaaatc tacaaggttt tgaaaccggg tggtacctttt      660 gctgtttacg aatgggtaat gactgataaa tatgacgaaa acaatcctga acatagaaag      720
atcgcttatg aaattgaact aggtgatggt atcccaaaga tgttccatgt cgacgtggct      780
aggaaagcat tgaagaactg tggtttcgaa gtcctcgtta gcgaagacct ggcggacaat      840
gatgatgaaa tcccttggta ttacccatta actggtgagt ggaagtacgt tcaaaactta      900
gctaatttgg ccacattttt cagaacttct tacttgggta gacaatttac tacagcaatg      960
gttactgtaa tggaaaaatt aggtctagcc ccagaaggtt ccaaggaagt tactgctgct     1020
ctagaaaatg ctgcggttgg tttagttgcc ggtggtaagt ccaagttatt cactccaatg     1080 atgctttttcg tcgctaggaa gccagaaaac gccgaaaccc ctcccaaac ttcccaagaa      1140 gcaactcaat aa                                                           1152
```

```
<210> SEQ ID NO 9
<211> LENGTH: 1437
<212> TYPE: DNA
<213> ORGANISM: Artificial Sequence
<220> FEATURE:
<223> OTHER INFORMATION: DHCR7 DNA sequences

<400> SEQUENCE: 9
atgatggcct ccgatagagt tagaaagaga cataaggggt ctgctaatgg tgctcaaacc       60
gttgaaaaag aaccatctaa agaaccagct caatggggta gagcttggga agttgattgg      120
```

-continued

```
ttttctttgt ccggtgttat cttgttgttg tgttttgctc cattcttggt ttctttcttc      180
attatggctt gcgaccaata ccaatgctct atttctcatc cattattgga cttgtacaac      240
ggtgatgcta ctttgttcac tatttggaat agagccccat cttttacttg ggctgctgct      300
aaaatctatg ctatttgggt tactttccaa gtcgtcttgt atatgtgtgt tccagatttc      360
ttgcacaaga ttttgccagg ttatgttggt ggtgttcaag atggtgctag aactccagct      420
ggtttgatta acaagtacga agtcaacggt ttacaatgct ggttgattac tcatgttttg      480
tgggttttga acgcccaaca ttttcattgg ttttccccaa ccattatcat cgataactgg      540
attccattat tgtggtgcac caacattttg ggttatgctg tttctacttt cgccttcatt      600
aaggcttact tgtttccaac taatccagaa gattgcaagt tcaccggtaa catgtttttac     660 aactacatga tgggtatcga attcaaccca agaatcggta agtggttcga tttcaagttg      720
ttctttaatg gtagaccagg tatcgttgct tggaccttga ttaacttgtc ttacgctgct      780
aagcaacaag aattatacgg ttacgttacc aactccatga tcttggttaa cgttttacaa      840
gccgtttacg tcgttgattt cttttggaat gaagcctggt acttgaaaac catcgatatc      900
tgccatgatc atttcggttg gtatttgggt tggggtgatt gtgtttggtt gccattcttg      960
tataccttac aaggcttgta cttggtctac aacccaatcc aattgtctac tccacatgct     1020
gctggtgttt tgattttggg tttggttggt tactacatct tcagagttac caaccaccaa     1080
aaggacttgt tcagaagaac tgaaggtaac tgttctatct ggggtaagaa gccaactttc     1140
attgaatgct cttaccaatc tgctgatggt gccattcata agtctaagtt gatggacttct    1200 ggtttctggg gtgttgctag acatatgaat tataccggtg atttgatggg ttctttggct     1260
tactgtttgg cttgtggtgg taatcatttg ttgccatact tctacatcat ctacatgacc     1320
atcttgttgg tccacagatg tatcagagat gaacatagat gctctaacaa gtacggtaag     1380
gattgggaaa gatatactgc tgctgtctcc tatagattat tgccaaacat cttttaa        1437
```

<210> SEQ ID NO 10
<211> LENGTH: 1551
<212> TYPE: DNA
<213> ORGANISM: Artificial Sequence
<220> FEATURE:
<223> OTHER INFORMATION: DHCR24 DNA sequences

<400> SEQUENCE: 10

```
atggacccctt tgttgtattt gggtggtttg gctgttttgt tcttgatttg gattaaggtc       60
aagggtttgg aatacgtcat catccatcaa agatggatct cgtttgctt gttcttgttg       120 ccattgtccg ttgttttcga tgtttactac catttgagag cctggatcat tttcaagatg       180
tgttctgctc caaagcaaca cgatcaaaga gttagagata tccaaagaca agttagagaa       240
tggcgtaagg acggtggtaa aaagtatatg tgtactggta gaccaggttg gttgactgtt       300
tctttgagag tcggtaagta caaaaagacc cacaagaaca ttatgatcaa catgatggac       360
atcttggaag ttgacaccaa gagaaaggtt gttagagttg aaccattggc taacatgggt       420
caagttactg ctttgttgaa ttctattggt tggaccttgc cagttttgcc agaattggat       480
gatttgactg ttggtggttt ggttatgggt actggtattg aatcttcctc tcatatctac       540
ggtttgttcc aacatatttg cgttgccttc gaattggttt tggctgatgg ttctttggtt       600
agatgcaccg aaaaagaaaa ctccgatttg ttttatgccg ttccatggtc ttgtggtact       660
ttgggttttt tggttgctgc cgaaattaga attattccag cacaaaagtg ggtcaagttg       720
```

-continued

```
cattatgaac cagttagagg tttggatgct atctgtaaga agttcgctga agaatccgcc      780
aacaaagaaa atcaattcgt tgaaggttta caatactcca gagatgaagc cgttattatg      840
actggtgtta tgactgatca tgccgaacca gataagacta actgtattgg ttactactac      900
aagccatggt tcttcagaca tgtcgaatct ttcttgaagc aaaacagagt tgccgtcgag      960
tatatcccat tgagacatta ttaccacaga cacaccagat ccattttctg ggaattgcaa     1020
gatattatcc cattcggtaa caaccctttg ttcagatatg ttttcggttg gatggttcca     1080
ccaaagatca gtttgttgaa attgactcaa ggtgaaacca tcagaaagtt gtacgaacaa     1140
catcacgttg tccaagatat gttggttcca atgaaggata ttaaggccgc cattcaaaga     1200
ttccatgaag atattcatgt ctacccattg tggttgtgtc cattcttgtt accaaatcaa     1260
ccaggtatgg ttcatccaaa gggtgacgaa gatgaattat acgttgatat tggtgcttac     1320
ggtgaaccta aggttaagca ctttgaagct acatcttcta ccagacaatt ggaaaagttc     1380
gttagagatg ttcacggttt ccaaatgttg tacgctgatg tttacatgga aagaaaagaa     1440
ttctgggaaa tgttcgacgg tacattatac cacaagttga gagaagaatt gggttgcaaa     1500
gatgctttcc cagaagtttt cgacaaaatc tgtaaatccg ccagacacta a             1551
```

<210> SEQ ID NO 11
<211> LENGTH: 1098
<212> TYPE: DNA
<213> ORGANISM: Saccharomyces cerevisiae

<400> SEQUENCE: 11

```
atggatttgg tcttagaagt cgctgaccat tatgtcttag acgacttgta cgctaaagtt      60
ctgcccgctt cgttggcagc taatattcct gtcaagtggc agaaattgct agggttgaac     120
agtgggttca gcaattctac gattttgcag gagactttga actccaagaa tgccgtcaaa     180
gaatgtagaa ggttctacgg gcaggtgcca ttcctgtttg atatgtcgac gacgtctttt     240
gcatcgctat tgcctcgttc cagcatcttg agagaattcc tctcactatg ggttattgtt     300
acgatctttg gtttactact ttacttattc acggctagtc tcagctacgt gtttgtgttt     360
gacaagtcga tttttcaacca tcctcgttac ttgaaaaacc aaatggcaat ggaaatcaag     420
ttggcagtca gtgctatccc atggatgtcg atgttgaccg ttccatggtt tgttatggaa     480
ttgaacggcc attctaaact atacatgaag attgattatg aaaaccacgg tgtaaggaag     540
ctcattatcg agtacttcac tttcatcttt ttcactgatt gcggtgtgta tttagcgcac     600
agatggttgc attggccaag ggtctaccgt gctctgcaca agcctcatca caagtggctg     660
gtctgcacac ctttcgcatc tcattctttc catcctgtag acgggttttt gcaatccatc     720
tcgtaccaca tctacccatt gattctgcca ttacacaagg tttcttattt gattctgttc     780
acttttgtta acttttggac tgttatgatt catgacggtc aatacctatc aaacaatcct     840
gccgtcaacg gtactgcctg ccacacggtt caccatctat atttcaacta caactacggt     900
caattcacca ctctgtggga cagactaggg ggttcttacc gtagaccaga tgactcattg     960
tttgatccta agttaagaga tgctaaggag acctgggacg ctcaagttaa ggaagttgaa     1020
catttcatca aggaggtcga aggtgatgat aatgatagaa tctatgaaaa cgacccaaat     1080
accaagaaga acaactga                                                    1098
```

<210> SEQ ID NO 12
<211> LENGTH: 669
<212> TYPE: DNA
<213> ORGANISM: Saccharomyces cerevisiae -continued

```
<400> SEQUENCE: 12
atgaagtttt tcccactcct tttgttgatt ggtgttgtag ctacattat gaacgtattg        60 ttcactacct ggttgccaac caattacatg ttcgatccaa aaactttgaa cgaaatatgt       120
aactcggtga ttagcaaaca caacgcagca gaaggtttat ccactgaaga cctgttacag       180
gatgtcagag acgcacttgc ctctcattac ggggacgaat acatcaacag gtacgtcaaa       240
gaagaatggg tcttcaacaa tgctggtggt gcgatgggcc aaatgatcat cctacacgct       300
tccgtatccg agtacttaat tctattcgga accgctgttg gtactgaagg cacacaggt        360 gttcactttg ctgacgacta ttttaccatc ttacatggta cgcaaatcgc agcattgcca       420
tatgccactg aagccgaagt ttacactcct ggtatgactc atcacttgaa gaagggatac       480
gccaagcaat acagcatgcc aggtggttcc tttgcccttg aattggctca aggctggatt       540
ccatgtatgt tgccattcgg gttttttggac actttctcca gtactcttga tttatacact       600
ctatatagaa ctgtctacct gactgccagg gacatgggta agaacttgtt gcaaaacaaa       660
aagttctaa                                                                669
```

```
<210> SEQ ID NO 13
<211> LENGTH: 1044
<212> TYPE: DNA
<213> ORGANISM: Saccharomyces cerevisiae

<400> SEQUENCE: 13
atgaacagga aagtagctat cgtaacgggt actaatagta atcttggtct gaacattgtg        60
ttccgtctga ttgaaactga ggacaccaat gtcagattga ccattgtggt gacttctaga       120
acgcttcctc gagtgcagga ggtgattaac cagattaaag attttacaa caaatcaggc        180 cgtgtagagg atttggaaat agactttgat tatctgttgg tggacttcac caacatggtg       240
agtgtcttga acgcatatta cgacatcaac aaaaagtaca gggcgataaa ctacctttc        300 gtgaatgctg cgcaaggtat ctttgacggt atagattgga tcggagcggt caaggaggtt       360
ttcaccaatc cattggaggc agtgacaaat ccgacataca agatacaact ggtgggcgtc       420
aagtctaaag atgacatggg gcttattttc caggccaatg tgtttggtcc gtactacttt       480
atcagtaaaa ttctgcctca attgaccagg ggaaaggctt atattgtttg gatttcgagt       540
attatgtccg atcctaagta tctttcgttg aacgatattg aactactaaa gacaaatgcc       600
tcttatgagg gctccaagcg tttagttgat ttactgcatt tggccaccta caaagacttg       660
aaaaagctgg gcataaatca gtatgtagtt caaccgggca tatttacaag ccattccttc       720
tccgaatatt tgaatttttt cacctatttc ggcatgctat gcttgttcta tttggccagg       780
ctgttggggt ctccatggca caatattgat ggttataaag ctgccaatgc cccagtatac       840
gtaactagat tggccaatcc aaactttgag aaacaagacg taaaatacgg ttctgctacc       900
tctagggatg gtatgccata tatcaagacg caggaaatag accctactgg aatgtctgat       960
gtcttcgctt atatacagaa gaagaaactg gaatgggacg agaaactgaa agatcaaatt      1020
gttgaaacta gaaccccat ttaa                                              1044
```

```
<210> SEQ ID NO 14
<211> LENGTH: 1929
<212> TYPE: DNA
<213> ORGANISM: Saccharomyces cerevisiae

<400> SEQUENCE: 14
```

```
atggacaaga agaaggatct actggagaac gaacaatttc tccgcatcca aaagctcaac      60
gctgccgatg cgggcaaaag acaatctata acagtggacg acgagggcga actatatggg     120
ttagacacct ccggcaactc accagccaat gaacacacag ctaccacaat tacacagaat     180
cacagcgtgg tggcctcaaa cggagacgtc gcattcatcc caggaactgc taccgaaggc     240
aatacagaga ttgtaactga agaagtgatt gagaccgatg ataacatgtt caagacccat     300
gtgaagactt taagctccaa agagaaggca cggtataggc aagggtcctc taactttata     360
tcgtatttcg atgatatgtc atttgaacac aggcccagta tattagatgg gtcagttaac     420
gagcccttca agaccaaatt cgtgggacct actttagaaa aggagatcag aagaagggag     480
aaagagctaa tggccatgcg caaaaattta caccaccgca agtcctcccc agatgctgtc     540
gactcagtag ggaaaaatga tggcgccgcc ccaactactg ttccaactgc cgccacctca     600
gaaacggtgg tcaccgttga aaccaccata atttcatcca atttctccgg gttgtacgtg     660 gcgtttttgga tggctattgc atttggtgct gtcaaggctt aaatagacta ttattaccag     720
cataatggta gcttcaagga ttcggagatc ttgaaattta tgactacgaa tttgttcact     780
gtggcatccg tagatctttt gatgtatttg agcacttatt ttgtcgttgg aatacaatac     840
ttatgcaagt gggggtctt gaaatggggc actaccggct ggatcttcac ctcaatttac     900 gagttttgt tgttatctt ctacatgtat ttaacagaaa acatcctaaa actacactgg     960
ctgtccaaga tcttcctttt tttgcattct ttagtttat tgatgaaaat gcattctttc    1020
gccttctaca atggctatct atggggtata aaggaagaac tacaatttc caaaagcgct    1080 cttgccaaat acaaggattc tataaatgat ccaaaagtta ttggtgctct tgagaaaagc    1140
tgtgagtttt gtagtttga attgagctct cagtctttaa gcgaccaaac tcaaaaattc    1200
cccaacaata tcagtgcaaa aagctttttt tggttcacca tgtttccaac cctaatttac    1260
caaattgaat atccaagaac taaggaaatc agatggagct acgtattaga aaagatctgc    1320
gccatcttcg gtaccatttt cttaatgatg atagatgctc aaatcttgat gtatcctgta    1380
gcaatgagag cattggctgt gcgcaattct gaatggactg gtatattgga tagattattg    1440
aaatgggttg gattgctcgt tgatatcgtc ccagggttta tcgtgatgta catcttggac    1500
ttctatttga tttgggatgc catttttgaac tgtgtggctg aattgacaag atttggcgac    1560
agatatttct acggtgactg gtggaattgt gttagttggg cagacttcag tagaatttgg    1620
aacatcccag tgcataagtt tttgttaaga catgtttacc atagttcaat gagttcattc    1680
aaattgaaca agagtcaagc aactttgatg accttttct taagttccgt cgttcatgaa    1740
ttagcaatgt acgttatctt caagaaattg aggtttact tgttcttctt ccaaatgctg    1800
caaatgccat tagtagcttt aacaaatact aaattcatga ggaacagaac cataatcgga    1860
aatgttattt tctggctcgg tatctgcatg ggaccaagtg tcatgtgtac gttgtacttg    1920
acattctaa                                                          1929
```

```
<210> SEQ ID NO 15
<211> LENGTH: 1635
<212> TYPE: DNA
<213> ORGANISM: Saccharomyces cerevisiae

<400> SEQUENCE: 15
atgaacagga aagtagctat cgtaacgggt actaatagta atcttggtct gaacattgtg      60
ttccgtctga ttgaaactga ggacaccaat gtcagattga ccattgtggt gacttctaga     120
acgcttcctc gagtgcagga ggtgattaac cagattaaag attttttacaa caaatcaggc     180
```

-continued

```
cgtgtagagg atttggaaat agactttgat tatctgttgg tggacttcac caacatggtg      240
agtgtcttga acgcatatta cgacatcaac aaaaagtaca gggcgataaa ctacctttc      300 gtgaatgctg cgcaaggtat ctttgacggt atagattgga tcggagcggt caaggaggtt      360
ttcaccaatc cattggaggc agtgacaaat ccgacataca agatacaact ggtgggcgtc      420
aagtctaaag atgacatggg gcttattttc caggccaatg tgtttggtcc gtactacttt      480
atcagtaaaa ttctgcctca attgaccagg ggaaaggctt atattgtttg gatttcgagt      540
attatgtccg atcctaagta tctttcgttg aacgatattg aactactaaa gacaaatgcc      600
tcttatgagg gctccaagcg tttagttgat ttactgcatt tggccaccta caaagacttg      660
aaaaagctgg gcataaatca gtatgtagtt caaccgggca tatttacaag ccattccttc      720
tccgaatatt tgaatttttt cacctatttc ggcatgctat gcttgttcta tttggccagg      780
ctgttggggt ctccatggca caatattgat ggttataaag ctgccaatgc cccagtatac      840
gtaactagat tggccaatcc aaactttgag aaacaagacg taaaatacgg ttctgctacc      900
tctagggatg gtatgccata tatcaagacg caggaaatag accctactgg aatgtctgat      960
gtcttcgctt atatacagaa gaagaaactg gaatgggacg agaaactgaa agatcaaatt     1020
gttgaaacta gaaccccccat tccaaccaat tacatgttcg atccaaaaac tttgaacgaa     1080
atatgtaact cggtgattag caaacacaac gcagcagaag gtttatccac tgaagacctg     1140
ttacaggatg tcagagacgc acttgcctct cattacgggg acgaatacat caacaggtac     1200
gtcaaagaag aatgggtctt caacaatgct ggtggtgcga tgggccaaat gatcatccta     1260
cacgcttccg tatccgagta cttaattcta ttcggaaccg ctgttggtac tgaagggcac     1320
acaggtgttc actttgctga cgactatttt accatcttac atggtacgca aatcgcagca     1380
ttgccatatg ccactgaagc cgaagtttac actcctggta tgactcatca cttgaagaag     1440
ggatacgcca agcaatacag catgccaggt ggttcctttg cccttgaatt ggctcaaggc     1500
tggattccat gtatgttgcc attcgggttt ttggacactt tctccagtac tcttgattta     1560
tacactctat atagaactgt ctacctgact gccagggaca tgggtaagaa cttgttgcaa     1620
aacaaaaagt tctaa                                                       1635
```

<210> SEQ ID NO 16
<211> LENGTH: 2739
<212> TYPE: DNA
<213> ORGANISM: Saccharomyces cerevisiae

<400> SEQUENCE: 16

```
atgagcgaag tcggtataca gaatcacaag aaagcggtga caaaacccag aagaagagaa       60
aaagtcatcg agctaattga agtggacggc aaaaaggtgt gtacgacttc aaccggtaaa      120
cgtaaattcc ataacaaatc aaagaatggg tgcgataact gtaaaagaag aagagttaag      180
tgtgatgaag ggaagccagc ctgtaggaag tgcacaaata tgaagttgga atgtcagtat      240
acaccaatcc atttaaggaa aggtagagga gcaacagtag tgaagtatgt cacgagaaag      300
gcagacggta gcgtggagtc tgattcatcg gtagatttac ctcctacgat caagaaggag      360
cagacaccgt tcaatgatat ccaatcagcg gtaaaagctt caggctcatc caatgattcc      420
tttccatcaa gcgcctctac aactaagagt gagagcgagg aaaagtcatc ggcccctata      480
gaggacaaaa acaatatgac tcctctaagt atgggcctcc agggtaccat caataagaaa      540
gatatgatga ataactttt ctctcaaaat ggcactattg gttttggttc tcctgaaaga      600
```

-continued

```
ttgaattcag gtatcgatgg cttactatta ccgccattgc cttctggaaa tatgggtgcg      660
ttccaacttc agcaacagca gcaagtgcag cagcaatctc aaccacagac ccaagcgcag      720
caagcaagtg gaactccaaa cgagagatat ggttcattcg atcttgcggg tagtcctgca      780
ttgcaatcca cgggaatgag cttatcaaat agtctaagcg ggatgttact atgtaacagg      840
attccttccg gccaaaacta cactcaacaa caattacaat atcaattaca ccagcagctg      900
caattgcaac agcatcagca agttcagctg cagcagtatc aacaattacg tcaggaacaa      960
caccaacaag ttcagcaaca acaacaggaa caactccagc aataccaaca acattttttg     1020
caacagcagc aacaagtact gcttcagcaa gagcaacaac ctaacgatga ggaaggtggc     1080
gttcaggaag aaaacagcaa aaaggtaaag gaagggcctt acaatcaca aacaagcgaa      1140 actactttaa acagcgatgc tgctacatta caagctgatg cattatctca gttaagtaag     1200
atggggctaa gcctaaagtc gttaagtacc tttccaacag ctggtattgg tggtgtttcc     1260
tatgactttc aggaactgtt aggtattaag tttccaataa ataacggcaa ttcaagagct     1320
actaaggcca gcaacgcaga ggaagctttg gccaatatgc aagagcatca tgaacgtgca     1380
gctgcttctg taaaggagaa tgatggtcag ctctctgata cgaagagtcc agcgccatcg     1440
aataacgccc aaggggggaag tgctagtatt atggaacctc aggcggctga tgcggtttcg     1500
acaatggcgc ctatatcaat gattgaaaga aacatgaaca gaaacagcaa catttctcca     1560
tcaacgccct ctgcagtgtt gaatgatagg caagagatgc aagattctat aagttctcta     1620
ggaaatctga caaaagcagc cttggagaac aacgaaccaa cgataagttt acaaacatca     1680
cagacagaga atgaagacga tgcatcgcgg caagacatga cctcaaaaat taataacgaa     1740
gctgaccgaa gttctgtttc tgctggtacc agtaacatcg ctaagctttt agatctttct     1800
accaaaggca atctgaacct gatagacatg aaactgtttc atcattattg cacaaaggtc     1860
tggcctacga ttacagcggc caaagtttct gggcctgaaa tatggaggga ctacataccg     1920
gagttagcat ttgactatcc attttttaatg cacgctttgt tggcattcag tgccaccccat    1980 ctttcgagga ctgaaactgg actggagcaa tacgtttcat ctcaccgcct agacgctctg     2040
agattattaa gagaagctgt tttagaaata tctgagaata acaccgatgc gctagttgcc     2100
agcgccctga tactaatcat ggactcgtta gcaaatgcta gtggtaacgg cactgtagga     2160
aaccaaagtt tgaatagcat gtcaccaagc gcttggatct ttcatgtcaa aggtgctgca     2220
acaattttaa ccgctgtgtg gccttttgagt gaaagatcta aatttcataa cattatatct     2280
gttgatctta gcgatttagg cgatgtcatt aaccctgatg ttggaacaat tactgaattg     2340
gtatgttttg atgaaagtat tgccgatttg tatcctgtcg gcttagattc gccatatttg     2400
ataacactag cttatttaga taaattgcac cgtgaaaaaa accagggtga ttttattctg     2460
cgggtattta catttccagc attgctagac aagacattcc tggcattact gatgacaggt     2520 gattaggtg caatgagaat tatgagatca tattataaac tacttcgagg atttgccaca     2580
gaggtcaagg ataaagtctg gtttctcgaa ggagtcacgc aggtgctgcc tcaagatgtt     2640
gacgaataca gtggaggtgg tgatatgcat atgatgctag atttcctcgg tggcggatta     2700
ccatcgatga caacaacaaa tttctctgat ttttcgtta                           2739
```

```
<210> SEQ ID NO 17
<211> LENGTH: 1437
<212> TYPE: DNA
<213> ORGANISM: Artificial Sequence
<220> FEATURE:
<223> OTHER INFORMATION: ccDHCR7
```

-continued

<400> SEQUENCE: 17

```
atgatggcct ctgacagagt cagaaagaga cataagggtt ccgctaacgg tgctcaaact      60
gttgaaaagg aaccatccaa agaacctgct caatggggca gagcttggga agttgactgg     120
ttctccttat ctggtgttat tctattgtta tgtttcgctc cattttttagt ttctttttc     180 attatggctt gtgaccaata ccaatgttct atttctcatc cattattgga tttatacaac     240
ggcgatgcta ctttatttac catctggaac agagccccat ctttcacttg ggctgccgct     300
aaaatttatg ctatttgggt tactttccaa gttgtcttat atatgtgtgt tccagatttt     360
ttgcacaaga ttttgcctgg ttatgttggt ggtgttcaag atggtgctag aaccccagct     420
ggtttaatca acaagtacga agtcaacggt ttgcaatgtt ggttgattac tcacgtttta     480 tgggtttttga acgcccaaca tttccactgg ttctctccaa ctatcatcat tgacaactgg     540
attccattgc tatggtgtac caacatctta ggttacgccg tttccacttt tgctttcatc     600
aaggcttatt tattcccaac caatccagaa gattgtaaat ttactggtaa tatgttttac     660
aattacatga tgggtatcga attcaaccca agaattggta aatggtttga tttcaagttg     720
ttcttcaatg gtagaccagg tattgttgca tggactttga ttaacttgtc ctacgctgct     780
aagcaacaag aattgtacgg ttatgtcact aactctatga ttttggttaa cgttttacaa     840
gctgtttacg ttgttgattt cttttggaat gaagcttggt atttgaagac cattgatatt     900
tgtcacgatc attttggttg gtacttgggc tggggtgact gtgtttggtt accattcttg     960
tatactctac aaggtctata cttagtctac aacccaattc aattgtctac tccacatgcc    1020
gccggtgtct tgatcttggg tttggtcggt tactacatct tcagagttac aaaccaccaa    1080
aaggacttgt ttagaagaac tgaaggtaac tgttccattt ggggtaagaa gccaacattt    1140
attgaatgtt cttatcaatc tgctgacggt gccattcata aatctaaatt aatgacctcc    1200
ggtttctggg gtgttgccag acacatgaac tacaccggtg atttgatggg ttctttggct    1260
tactgtttgg cctgtggtgg taaccatttg ttgccatact ctacattat ttacatgact    1320 attttattag ttcatcgttg tattagagat gaacacagat gttccaacaa atatggtaag    1380
gattgggaaa gatacactgc tgctgtctct tacagattgc taccaaacat tttctaa      1437
```

<210> SEQ ID NO 18
<211> LENGTH: 1551
<212> TYPE: DNA
<213> ORGANISM: Artificial Sequence
<220> FEATURE:
<223> OTHER INFORMATION: ccDHCR24

<400> SEQUENCE: 18

```
atggacccat tgctatactt aggtggtttg gccgtcttat ttttgatttg gatcaaggtc      60
aagggtttag aatacgttat cattcaccaa agatggattt ttgtttgttt gttttttacta     120 ccattgtctg tcgtcttcga tgtctactac catttgagag cttggattat cttcaagatg     180
tgttccgctc caaagcaaca cgatcaaaga gtcagagata tccaacgtca agttagagaa     240
tggagaaagg atggtggtaa gaagtacatg tgtaccggta gaccaggctg gttgaccgtt     300
tctttgcgtg tcggtaaata caaaaagact cacaagaaca ttatgattaa tatgatggat     360
attttggaag ttgacaccaa gagaaaagtt gtccgtgttg aacctttggc gaacatgggt     420
caagtcactg ctttgttgaa ctccatcggt tggactttgc ctgttttgcc agagttagat     480
gatttaactg ttggtggctt ggtcatgggt actggtattg aatcctcctc tcacatttat     540
```

-continued

```
ggtctatttc aacatatttg tgttgcattt gaattagtct tggctgacgg ttctctagtc      600
agatgtactg aaaaagaaaa ctctgatttg ttctacgctg tcccatggtc ttgtggtacc      660
ttggggttct tggttgctgc cgaaattaga atcatcccag ctcaaaagtg ggttaaattg      720
cattatgaac cagttagagg tttggatgcc atctgtaaga aatttgctga agaatctgct      780
aacaaggaaa atcaatttgt cgaaggttta caatactcca gagacgaagc tgttattatg      840
acaggtgtta tgactgatca tgctgaacca gataagacca actgtattgg ttactattac      900
aagccatggt tcttccgtca tgtcgagtct ttcttgaaac aaaacagagt tgccgttgaa      960
tatattcctt taagacacta ctaccacaga cacactagat ccattttctg ggaattgcaa     1020
gacattattc catttggtaa caacccatta ttcagatatg ttttcggttg gatggttcca     1080
ccaaaaattt ctttattgaa gttgactcaa ggtgaaacta tcagaaagtt atacgaacaa     1140
catcacgttg ttcaagatat gttagttcca atgaaggaca ttaaggctgc tattcaaaga     1200
ttccacgaag acatccatgt ttacccatta tggttatgtc cattcttatt accaaaccaa     1260
ccaggtatgg tccatccaaa aggtgatgaa gatgaattgt acgtcgatat tggtgcttac     1320
ggtgagccaa aggttaagca tttcgaagcc acttcttcta ccagacaatt ggaaaagttc     1380
gttcgtgacg ttcacggttt ccaaatgttg tatgctgatg tttatatgga aagaaaggaa     1440
ttttgggaaa tgtttgatgg tactttatat cataaattac gtgaagagtt gggttgtaaa     1500
gatgctttcc cagaagtctt tgacaagatt tgcaaatctg ccagacatta g              1551
```

<210> SEQ ID NO 19
<211> LENGTH: 1512
<212> TYPE: DNA
<213> ORGANISM: Artificial Sequence
<220> FEATURE:
<223> OTHER INFORMATION: tHMG1

<400> SEQUENCE: 19

```
atgccagttt taaccaataa aacagtcatt tctggatcga aagtcaaaag tttatcatct       60
gcgcaatcga gctcatcagg accttcatca tctagtgagg aagatgattc ccgcgatatt      120
gaaagcttgg ataagaaaat acgtccttta gaagaattag aagcattatt aagtagtgga      180
aatacaaaac aattgaagaa caaagaggtc gctgccttgg ttattcacgg taagttacct      240
ttgtacgctt tggagaaaaa attaggtgat actacgagag cggttgcggt acgtaggaag      300
gctctttcaa tttttggcaga agctcctgta ttagcatctg atcgtttacc atataaaaat      360
tatgactacg accgcgtatt tggcgcttgt tgtgaaaatg ttataggtta catgcctttg      420
cccgttggtg ttataggccc cttggttatc gatggtacat cttatcatat accaatggca      480
actacagagg gttgtttggt agcttctgcc atgcgtggct gtaaggcaat caatgctggc      540
ggtggtgcaa caactgtttt aactaaggat ggtatgacaa gaggcccagt agtccgtttc      600
ccaactttga aagatctggg tgcctgtaag atatggttag actcagaaga gggacaaaac      660
gcaattaaaa aagcttttaa ctctacatca agatttgcac gtctgcaaca tattcaaact      720
tgtctagcag gagatttact cttcatgaga tttagaacaa ctactggtga cgcaatgggt      780
atgaatatga tttctaaagg tgtcgaatac tcattaaagc aaatggtaga agagtatggc      840
tgggaagata tggaggttgt ctccgtttct ggtaactact gtaccgacaa aaaaccagct      900
gccatcaact ggatcgaagg tcgtggtaag agtgtcgtcg cagaagctac tattcctggt      960
gatgttgtca gaaaagtgtt aaaaagtgat gtttccgcat tggttgagtt gaacattgct     1020
aagaatttgg ttggatctgc aatggctggg tctgttggtg gatttaacgc acatgcagct     1080
```

-continued

```
aatttagtga cagctgtttt cttggcatta ggacaagatc ctgcacaaaa tgttgaaagt     1140
tccaactgta taacattgat gaaagaagtg gacggtgatt tgagaatttc cgtatccatg     1200
ccatccatcg aagtaggtac catcggtggt ggtactgttc tagaaccaca aggtgccatg     1260
ttggacttat taggtgtaag aggcccgcat gctaccgctc ctggtaccaa cgcacgtcaa     1320
ttagcaagaa tagttgcctg tgccgtcttg gcaggtgaat tatccttatg tgctgcccta     1380
gcagccggcc atttggttca aagtcatatg acccacaaca ggaaacctgc tgaaccaaca     1440
aaacctaaca atttggacgc cactgatata aatcgtttga aagatgggtc cgtcacctgc     1500
attaaatcct aa                                                         1512
```

<210> SEQ ID NO 20
<211> LENGTH: 31
<212> TYPE: DNA
<213> ORGANISM: Artificial Sequence
<220> FEATURE:
<223> OTHER INFORMATION: erg5 dN fw

<400> SEQUENCE: 20

```
acatgcatgc cgctattgaa gagagctcat g                                      31
```

<210> SEQ ID NO 21
<211> LENGTH: 47
<212> TYPE: DNA
<213> ORGANISM: Artificial Sequence
<220> FEATURE:
<223> OTHER INFORMATION: erg5 dN rv

<400> SEQUENCE: 21

```
gcggccgcgg gtctagaggg ggatccccag gatactgaag gcagtag                     47
```

<210> SEQ ID NO 22
<211> LENGTH: 48
<212> TYPE: DNA
<213> ORGANISM: Artificial Sequence
<220> FEATURE:
<223> OTHER INFORMATION: erg5 dC fw

<400> SEQUENCE: 22

```
ggatccccct ctagacccgc ggccgccatg attaccttcg ccgctttg                    48
```

<210> SEQ ID NO 23
<211> LENGTH: 28
<212> TYPE: DNA
<213> ORGANISM: Artificial Sequence
<220> FEATURE:
<223> OTHER INFORMATION: erg5 dC rv

<400> SEQUENCE: 23

```
cgacgcgtgc tggcagggtg agtatttg                                          28
```

<210> SEQ ID NO 24
<211> LENGTH: 31
<212> TYPE: DNA
<213> ORGANISM: Artificial Sequence
<220> FEATURE:
<223> OTHER INFORMATION: erg6 dN fw

<400> SEQUENCE: 24

```
acgtgcatgc gctgttgccg ataacttctt c                                      31
```

<210> SEQ ID NO 25

-continued

```
<211> LENGTH: 56
<212> TYPE: DNA
<213> ORGANISM: Artificial Sequence
<220> FEATURE:
<223> OTHER INFORMATION: erg6 dN rv

<400> SEQUENCE: 25
gcggccgcgg gtctagaggg ctcgaggggg gatccctcaa ttctgtttca ctcatc          56

<210> SEQ ID NO 26
<211> LENGTH: 53
<212> TYPE: DNA
<213> ORGANISM: Artificial Sequence
<220> FEATURE:
<223> OTHER INFORMATION: erg6 dC fw

<400> SEQUENCE: 26
ggatcccccc tcgagccctc tagacccgcg gccgccctcc caaacttccc aag             53

<210> SEQ ID NO 27
<211> LENGTH: 28
<212> TYPE: DNA
<213> ORGANISM: Artificial Sequence
<220> FEATURE:
<223> OTHER INFORMATION: erg6 dC rv

<400> SEQUENCE: 27
cgacgcgtct tgccgctgta gacaatag                                         28

<210> SEQ ID NO 28
<211> LENGTH: 31
<212> TYPE: DNA
<213> ORGANISM: Artificial Sequence
<220> FEATURE:
<223> OTHER INFORMATION: DHCR7 fw

<400> SEQUENCE: 28
aactgcagat gatggcctcc gatagagtta g                                     31

<210> SEQ ID NO 29
<211> LENGTH: 61
<212> TYPE: DNA
<213> ORGANISM: Artificial Sequence
<220> FEATURE:
<223> OTHER INFORMATION: DHCR7 rv

<400> SEQUENCE: 29
gcgtcgactt acttgtcgtc atcgtctttg tagtcaaaga tgtttggcaa taatctatag      60
g                                                                      61

<210> SEQ ID NO 30
<211> LENGTH: 31
<212> TYPE: DNA
<213> ORGANISM: Artificial Sequence
<220> FEATURE:
<223> OTHER INFORMATION: DHCR24 fw

<400> SEQUENCE: 30
aactgcagat ggaccctttg ttgtatttgg g                                     31

<210> SEQ ID NO 31
<211> LENGTH: 57
<212> TYPE: DNA
<213> ORGANISM: Artificial Sequence
<220> FEATURE:
<223> OTHER INFORMATION: DHCR24 rv
```

<400> SEQUENCE: 31
gcgtcgactt acgcatagtc aggaacatcg tatgggtagt gtctggcgga tttacag        57

<210> SEQ ID NO 32
<211> LENGTH: 32
<212> TYPE: DNA
<213> ORGANISM: Artificial Sequence
<220> FEATURE:
<223> OTHER INFORMATION: TEF1p fw

<400> SEQUENCE: 32
ccgctcgaga gctcatagct tcaaaatgtt tc        32

<210> SEQ ID NO 33
<211> LENGTH: 28
<212> TYPE: DNA
<213> ORGANISM: Artificial Sequence
<220> FEATURE:
<223> OTHER INFORMATION: TEF1p rv

<400> SEQUENCE: 33
gctctagagg ggaaacttaa agaaattc        28

<210> SEQ ID NO 34
<211> LENGTH: 31
<212> TYPE: DNA
<213> ORGANISM: Artificial Sequence
<220> FEATURE:
<223> OTHER INFORMATION: GAL7t fw

<400> SEQUENCE: 34
acgcgtcgac ttgaacgaaa cttgaacgga g        31

<210> SEQ ID NO 35
<211> LENGTH: 28
<212> TYPE: DNA
<213> ORGANISM: Artificial Sequence
<220> FEATURE:
<223> OTHER INFORMATION: GAL7t rv

<400> SEQUENCE: 35
gctctagagg ggaaacttaa agaaattc        28

<210> SEQ ID NO 36
<211> LENGTH: 40
<212> TYPE: DNA
<213> ORGANISM: Artificial Sequence
<220> FEATURE:
<223> OTHER INFORMATION: ACT1p fw

<400> SEQUENCE: 36
cgaagttatt agggcggccg ctttggactc caccaacgtc        40

<210> SEQ ID NO 37
<211> LENGTH: 44
<212> TYPE: DNA
<213> ORGANISM: Artificial Sequence
<220> FEATURE:
<223> OTHER INFORMATION: ACT1p rv

<400> SEQUENCE: 37
atcggaggcc atcattgtta attcagtaaa ttttcgatct tggg        44

<210> SEQ ID NO 38

-continued

```
<211> LENGTH: 33
<212> TYPE: DNA
<213> ORGANISM: Artificial Sequence
<220> FEATURE:
<223> OTHER INFORMATION: DHCR7 fw2

<400> SEQUENCE: 38
tgaattaaca atgatggcct ccgatagagt tag                             33

<210> SEQ ID NO 39
<211> LENGTH: 37
<212> TYPE: DNA
<213> ORGANISM: Artificial Sequence
<220> FEATURE:
<223> OTHER INFORMATION: DHCR7 rv2

<400> SEQUENCE: 39
ctttaatttg cggccttact tgtcgtcatc gtctttg                         37

<210> SEQ ID NO 40
<211> LENGTH: 35
<212> TYPE: DNA
<213> ORGANISM: Artificial Sequence
<220> FEATURE:
<223> OTHER INFORMATION: CYC1t fw

<400> SEQUENCE: 40
gatgacgaca agtaaggccg caaattaaag ccttc                           35

<210> SEQ ID NO 41
<211> LENGTH: 38
<212> TYPE: DNA
<213> ORGANISM: Artificial Sequence
<220> FEATURE:
<223> OTHER INFORMATION: CYC1t rv

<400> SEQUENCE: 41
acctctggcg cggcctcatg taattagtta tgtcacgc                        38

<210> SEQ ID NO 42
<211> LENGTH: 37
<212> TYPE: DNA
<213> ORGANISM: Artificial Sequence
<220> FEATURE:
<223> OTHER INFORMATION: TDH3p fw

<400> SEQUENCE: 42
cgcggatccg tagaatcatt ttgaataaaa aacacgc                         37

<210> SEQ ID NO 43
<211> LENGTH: 50
<212> TYPE: DNA
<213> ORGANISM: Artificial Sequence
<220> FEATURE:
<223> OTHER INFORMATION: TDH3p rv

<400> SEQUENCE: 43
acttctaaga ccaaatccat gaattctgtt tatgtgtgtt tattcgaaac           50

<210> SEQ ID NO 44
<211> LENGTH: 50
<212> TYPE: DNA
<213> ORGANISM: Artificial Sequence
<220> FEATURE:
<223> OTHER INFORMATION: ERG3 fw

<400> SEQUENCE: 44
```
acttctaaga ccaaatccat gaattctgtt tatgtgtgtt tattcgaaac                50

<210> SEQ ID NO 45
<211> LENGTH: 50
<212> TYPE: DNA
<213> ORGANISM: Artificial Sequence
<220> FEATURE:
<223> OTHER INFORMATION: ERG3 rv

<400> SEQUENCE: 45
agaaaagtct tatcaatctc cgtcgactca gttgttcttc ttggtatttg                50

<210> SEQ ID NO 46
<211> LENGTH: 50
<212> TYPE: DNA
<213> ORGANISM: Artificial Sequence
<220> FEATURE:
<223> OTHER INFORMATION: TEF1t fw

<400> SEQUENCE: 46
caaataccaa gaagaacaac tgagtcgacg gagattgata agacttttct             50

<210> SEQ ID NO 47
<211> LENGTH: 33
<212> TYPE: DNA
<213> ORGANISM: Artificial Sequence
<220> FEATURE:
<223> OTHER INFORMATION: TEF1t rv

<400> SEQUENCE: 47
ccgctcgagg taaaaaatac gcccgtaacg atg                                 33

<210> SEQ ID NO 48
<211> LENGTH: 31
<212> TYPE: DNA
<213> ORGANISM: Artificial Sequence
<220> FEATURE:
<223> OTHER INFORMATION: TEF2p fw

<400> SEQUENCE: 48
ccgctcgagt gccattaaag gcgaattttt g                                   31

<210> SEQ ID NO 49
<211> LENGTH: 50
<212> TYPE: DNA
<213> ORGANISM: Artificial Sequence
<220> FEATURE:
<223> OTHER INFORMATION: TEF2p rv

<400> SEQUENCE: 49
aaggagtggg aaaaacttca tgcatgcgtt tagttaatta tagttcgttg                50

<210> SEQ ID NO 50
<211> LENGTH: 50
<212> TYPE: DNA
<213> ORGANISM: Artificial Sequence
<220> FEATURE:
<223> OTHER INFORMATION: ERG2 fw

<400> SEQUENCE: 50
caacgaacta taattaacta aacgcatgca tgaagttttt cccactcctt                50

<210> SEQ ID NO 51
<211> LENGTH: 50
<212> TYPE: DNA

<213> ORGANISM: Artificial Sequence
<220> FEATURE:
<223> OTHER INFORMATION: ERG2 rv

<400> SEQUENCE: 51
agatttaaag taaattcacg catgcttaga acttttttgtt ttgcaacaag                50

<210> SEQ ID NO 52
<211> LENGTH: 50
<212> TYPE: DNA
<213> ORGANISM: Artificial Sequence
<220> FEATURE:
<223> OTHER INFORMATION: TDH3t fw

<400> SEQUENCE: 52
cttgttgcaa aacaaaaagt tctaagcatg cgtgaattta ctttaaatct                50

<210> SEQ ID NO 53
<211> LENGTH: 35
<212> TYPE: DNA
<213> ORGANISM: Artificial Sequence
<220> FEATURE:
<223> OTHER INFORMATION: TDH3t rv

<400> SEQUENCE: 53
ccgctcgagt ctagatatat gttatcttat cttgg                                35

<210> SEQ ID NO 54
<211> LENGTH: 46
<212> TYPE: DNA
<213> ORGANISM: Artificial Sequence
<220> FEATURE:
<223> OTHER INFORMATION: ERG27-2 fw1

<400> SEQUENCE: 54
cgaacatgta attggttgga atgggggttc tagtttcaac aatttg                    46

<210> SEQ ID NO 55
<211> LENGTH: 48
<212> TYPE: DNA
<213> ORGANISM: Artificial Sequence
<220> FEATURE:
<223> OTHER INFORMATION: ERG27-2 rv1

<400> SEQUENCE: 55
ctataattaa ctaaacgcat gcatgaacag gaaagtagct atcgtaac                  48

<210> SEQ ID NO 56
<211> LENGTH: 54
<212> TYPE: DNA
<213> ORGANISM: Artificial Sequence
<220> FEATURE:
<223> OTHER INFORMATION: ERG27-2 fw2

<400> SEQUENCE: 56
aagatttaaa gtaaattcac gcatgcttag aacttttttgt tttgcaacaa gttc          54

<210> SEQ ID NO 57
<211> LENGTH: 44
<212> TYPE: DNA
<213> ORGANISM: Artificial Sequence
<220> FEATURE:
<223> OTHER INFORMATION: ERG27-2 rv2

<400> SEQUENCE: 57
gttgaaacta gaaccccccat tccaaccaat tacatgttcg atcc                     44

-continued

```
<210> SEQ ID NO 58
<211> LENGTH: 30
<212> TYPE: DNA
<213> ORGANISM: Artificial Sequence
<220> FEATURE:
<223> OTHER INFORMATION: ARE2 dN fw1

<400> SEQUENCE: 58
acatgcatgc caagtcgtaa acctcgtcgg                                    30

<210> SEQ ID NO 59
<211> LENGTH: 37
<212> TYPE: DNA
<213> ORGANISM: Artificial Sequence
<220> FEATURE:
<223> OTHER INFORMATION: ARE2 dN rv1

<400> SEQUENCE: 59
gatatcgcgc tcgaggttct ccagtagatc cttcttc                            37

<210> SEQ ID NO 60
<211> LENGTH: 36
<212> TYPE: DNA
<213> ORGANISM: Artificial Sequence
<220> FEATURE:
<223> OTHER INFORMATION: ARE2 dN fw2

<400> SEQUENCE: 60
ctcgagcgcg atatcggacc aagtgtcatg tgtacg                             36

<210> SEQ ID NO 61
<211> LENGTH: 35
<212> TYPE: DNA
<213> ORGANISM: Artificial Sequence
<220> FEATURE:
<223> OTHER INFORMATION: ARE2 dN rv2

<400> SEQUENCE: 61
ccgacgcgtg gcaaatagat tggttaaatc tgaag                              35

<210> SEQ ID NO 62
<211> LENGTH: 54
<212> TYPE: DNA
<213> ORGANISM: Artificial Sequence
<220> FEATURE:
<223> OTHER INFORMATION: 101HIS fw

<400> SEQUENCE: 62
gctatacgaa gttattaggc ccggggattg gcattatcac ataatgaatt atac         54

<210> SEQ ID NO 63
<211> LENGTH: 65
<212> TYPE: DNA
<213> ORGANISM: Artificial Sequence
<220> FEATURE:
<223> OTHER INFORMATION: 101HIS rv

<400> SEQUENCE: 63
caccttgaaa ctacctctgg cgcggccgct cgagttcaag agaaaaaaaa agaaaaagca   60
aaaag                                                               65

<210> SEQ ID NO 64
<211> LENGTH: 45
<212> TYPE: DNA
```

-continued

```
<213> ORGANISM: Artificial Sequence
<220> FEATURE:
<223> OTHER INFORMATION: ccD7 fw

<400> SEQUENCE: 64
ctaatctaag ttttctagct gcagatgatg gcctctgaca gagtc                      45

<210> SEQ ID NO 65
<211> LENGTH: 49
<212> TYPE: DNA
<213> ORGANISM: Artificial Sequence
<220> FEATURE:
<223> OTHER INFORMATION: ccD7 rv

<400> SEQUENCE: 65
gtcactccgt tcaagtcgac ttagaaaatg tttggtagca atctgtaag                   49

<210> SEQ ID NO 66
<211> LENGTH: 44
<212> TYPE: DNA
<213> ORGANISM: Artificial Sequence
<220> FEATURE:
<223> OTHER INFORMATION: ccD24 fw

<400> SEQUENCE: 66
ctaagttttc taactgcaga tggacccatt gctatactta ggtg                        44

<210> SEQ ID NO 67
<211> LENGTH: 48
<212> TYPE: DNA
<213> ORGANISM: Artificial Sequence
<220> FEATURE:
<223> OTHER INFORMATION: ccD24 rv

<400> SEQUENCE: 67
caagtttcgt tcaagtcgac ctaatgtctg gcagatttgc aaatcttg                    48

<210> SEQ ID NO 68
<211> LENGTH: 27
<212> TYPE: DNA
<213> ORGANISM: Artificial Sequence
<220> FEATURE:
<223> OTHER INFORMATION: tHMG1-fw

<400> SEQUENCE: 68
ggaattcatg ccagttttaa ccaataa                                           27

<210> SEQ ID NO 69
<211> LENGTH: 58
<212> TYPE: DNA
<213> ORGANISM: Artificial Sequence
<220> FEATURE:
<223> OTHER INFORMATION: tHMG1-rv

<400> SEQUENCE: 69
gcgtcgactt acgcatagtc aggaacatcg tatgggtagg atttaatgca ggtgacgg         58
```